(12) United States Patent
Mehta et al.

(10) Patent No.: US 10,086,087 B2
(45) Date of Patent: *Oct. 2, 2018

(54) MODIFIED RELEASE FORMULATIONS CONTAINING DRUG-ION EXCHANGE RESIN COMPLEXES

(71) Applicant: Tris Pharma, Inc., Monmouth Junction, NJ (US)

(72) Inventors: Ketan Mehta, Miami, FL (US); Yu-Hsing Tu, West Windsor, NJ (US)

(73) Assignee: Tris Pharma, Inc., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,637

(22) Filed: Jun. 12, 2017

(65) Prior Publication Data

US 2017/0274088 A1  Sep. 28, 2017

Related U.S. Application Data

(63) Continuation of application No. 15/200,786, filed on Jul. 1, 2016, now Pat. No. 9,675,704, which is a continuation of application No. 15/047,388, filed on Feb. 18, 2016, now Pat. No. 9,549,989, which is a continuation of application No. 14/508,613, filed on Oct. 7, 2014, now Pat. No. 9,522,191, which is a continuation of application No. 14/155,410, filed on Jan. 15, 2014, now Pat. No. 8,883,217, which is a continuation of application No. 14/065,842, filed on Oct. 29, 2013, now Pat. No. 8,747,902, which is a continuation of application No. 14/044,105, filed on Oct. 2, 2013, now Pat. No. 8,790,700, which is a continuation of application No. 13/746,654, filed on Jan. 22, 2013, now Pat. No. 8,597,684, which is a
(Continued)

(51) Int. Cl.
| | |
|---|---|
| A61K 47/32 | (2006.01) |
| A61K 31/135 | (2006.01) |
| A61K 31/137 | (2006.01) |
| A61K 31/155 | (2006.01) |
| A61K 31/192 | (2006.01) |
| A61K 31/216 | (2006.01) |
| A61K 31/24 | (2006.01) |
| A61K 31/4402 | (2006.01) |
| A61K 31/4458 | (2006.01) |
| A61K 31/485 | (2006.01) |
| A61K 45/06 | (2006.01) |
| A61K 47/14 | (2017.01) |
| A61K 9/00 | (2006.01) |
| A61K 9/10 | (2006.01) |
| A61K 9/14 | (2006.01) |
| A61K 9/16 | (2006.01) |
| A61K 9/20 | (2006.01) |
| A61K 9/48 | (2006.01) |
| A61K 9/50 | (2006.01) |
| A61K 47/58 | (2017.01) |
| A61K 47/69 | (2017.01) |

(52) U.S. Cl.
CPC .......... *A61K 47/585* (2017.08); *A61K 9/0053* (2013.01); *A61K 9/0056* (2013.01); *A61K 9/0095* (2013.01); *A61K 9/10* (2013.01); *A61K 9/14* (2013.01); *A61K 9/167* (2013.01); *A61K 9/1635* (2013.01); *A61K 9/1664* (2013.01); *A61K 9/2013* (2013.01); *A61K 9/2027* (2013.01); *A61K 9/2031* (2013.01); *A61K 9/2077* (2013.01); *A61K 9/2081* (2013.01); *A61K 9/4866* (2013.01); *A61K 9/5021* (2013.01); *A61K 9/5026* (2013.01); *A61K 31/135* (2013.01); *A61K 31/137* (2013.01); *A61K 31/155* (2013.01); *A61K 31/192* (2013.01); *A61K 31/216* (2013.01); *A61K 31/24* (2013.01); *A61K 31/4402* (2013.01); *A61K 31/4458* (2013.01); *A61K 31/485* (2013.01); *A61K 45/06* (2013.01); *A61K 47/14* (2013.01); *A61K 47/32* (2013.01); *A61K 47/6921* (2017.08); *A61K 47/6927* (2017.08); *A61K 47/6933* (2017.08)

(58) Field of Classification Search
None
See application file for complete search history.

(56) References Cited

U.S. PATENT DOCUMENTS

| | | |
|---|---|---|
| 2,099,402 A | 11/1937 | Keller |
| 2,507,631 A | 5/1950 | Hartmann |

(Continued)

FOREIGN PATENT DOCUMENTS

| | | |
|---|---|---|
| BE | 729827 | 9/1969 |
| CA | 2758556 A1 | 5/2013 |

(Continued)

OTHER PUBLICATIONS

US 7,431,994, 10/2008, Mehta (withdrawn)
(Continued)

*Primary Examiner* — Susan T Tran
*Assistant Examiner* — William Craigo
(74) *Attorney, Agent, or Firm* — Howson and Howson LLP; Cathy A. Kodroff; Egon Berg

(57) ABSTRACT

A particulate, modified release barrier coated drug-cation exchange resin complex comprising a core composed of a drug complexed with a pharmaceutically acceptable ion-exchange resin is provided. Methods of making and products containing this coated complex are described.

22 Claims, No Drawings

Related U.S. Application Data continuation of application No. 13/666,424, filed on Nov. 1, 2012, now Pat. No. 8,491,935, which is a continuation of application No. 12/722,857, filed on Mar. 12, 2010, now Pat. No. 8,337,890, which is a continuation of application No. 11/724,966, filed on Mar. 15, 2007, now Pat. No. 8,062,667.

(60) Provisional application No. 60/783,181, filed on Mar. 16, 2006.

(56) References Cited

U.S. PATENT DOCUMENTS

| | | |
|---|---|---|
| 2,809,918 A | 10/1957 | Hermelin |
| 2,830,933 A | 4/1958 | Bouchard |
| 2,957,880 A | 10/1960 | Rudolf |
| 2,990,332 A | 6/1961 | Keating |
| 3,048,526 A | 8/1962 | Boswell |
| 3,138,525 A | 6/1964 | Koff |
| 3,365,365 A | 1/1968 | Butler |
| 3,499,960 A | 3/1970 | Macek |
| 3,594,470 A | 7/1971 | Borodkin |
| 3,979,349 A | 9/1976 | Fink |
| 4,221,778 A | 9/1980 | Raghunathan |
| 4,459,278 A | 7/1984 | Porter |
| 4,510,128 A | 4/1985 | Khanna |
| 4,600,645 A | 7/1986 | Ghebre-Sallasie |
| 4,619,934 A | 10/1986 | Sunshine |
| 4,752,470 A | 6/1988 | Mehta et al. |
| 4,762,709 A | 8/1988 | Sheumaker |
| 4,765,989 A | 8/1988 | Wong |
| 4,775,536 A | 10/1988 | Patell |
| 4,794,001 A | 12/1988 | Mehta |
| 4,808,411 A | 2/1989 | Fu |
| 4,847,077 A | 7/1989 | Raghunathan |
| 4,859,461 A | 8/1989 | Chow |
| 4,871,549 A | 10/1989 | Veda |
| 4,876,094 A | 10/1989 | Benton |
| 4,891,549 A | 1/1990 | Geoghegan |
| 4,894,239 A | 1/1990 | Nonomura |
| 4,910,214 A | 3/1990 | Katjalainen |
| 4,952,402 A | 8/1990 | Sparks |
| 4,910,932 A | 10/1990 | Theeuwes |
| 4,996,047 A | 2/1991 | Kelleher |
| 4,996,058 A | 2/1991 | Sinnreich |
| 4,999,189 A | 3/1991 | Kogan |
| 5,032,393 A | 7/1991 | Douglas |
| 5,071,646 A | 12/1991 | Malkowska |
| 5,093,200 A | 3/1992 | Watanabe |
| 5,156,850 A | 10/1992 | Wong et al. |
| 5,158,777 A | 10/1992 | Abramowitz |
| 5,186,930 A | 2/1993 | Kogan et al. |
| 5,219,563 A | 6/1993 | Douglas |
| 5,260,068 A | 11/1993 | Chen |
| 5,273,760 A | 12/1993 | Oshlack |
| 5,275,819 A | 1/1994 | Amer |
| 5,275,820 A | 1/1994 | Chang |
| 5,286,493 A | 2/1994 | Oshlack |
| 5,296,236 A | 3/1994 | Santus |
| 5,368,852 A | 11/1994 | Umemoto |
| 5,374,659 A | 12/1994 | Gowan, Jr. |
| 5,409,907 A | 4/1995 | Blase |
| 5,411,745 A | 5/1995 | Oshlack |
| 5,422,121 A | 6/1995 | Lehmann |
| 5,496,561 A | 3/1996 | Okada |
| 5,580,578 A | 12/1996 | Oshlack |
| 5,837,284 A | 11/1998 | Mehta |
| 5,874,090 A | 2/1999 | Baker |
| 5,908,850 A | 6/1999 | Zeitlin |
| 5,968,551 A | 10/1999 | Oshlack |
| 5,980,088 A | 11/1999 | Iwasaki |
| 5,980,882 A | 11/1999 | Eichman |
| 6,001,392 A | 12/1999 | Wen |
| 6,046,277 A | 4/2000 | Kolter |
| 6,066,334 A | 5/2000 | Kolter |
| 6,217,904 B1 | 4/2001 | Midha |
| 6,228,398 B1 | 5/2001 | Devane |
| 6,228,863 B1 | 5/2001 | Palermo |
| 6,231,936 B1 | 5/2001 | Kozimor |
| 6,322,011 B1 | 11/2001 | Burnside |
| 6,322,819 B1 | 11/2001 | Burnside |
| 6,326,027 B1 | 12/2001 | Miller |
| 6,344,215 B1 | 2/2002 | Bettman |
| 6,355,656 B1 | 3/2002 | Zeitlin |
| 6,384,020 B1 | 5/2002 | Flanner |
| 6,419,954 B1 | 7/2002 | Chu |
| 6,419,960 B1 | 7/2002 | Krishnamurthy |
| 6,432,440 B1 | 8/2002 | Watts |
| 6,436,430 B1 | 8/2002 | Mulye |
| 6,528,530 B2 | 3/2003 | Zeitlin |
| 6,551,617 B1 | 4/2003 | Corbo |
| 6,551,620 B2 | 4/2003 | Otterbeck |
| 6,555,127 B2 | 4/2003 | Steiner |
| 6,555,136 B2 | 4/2003 | Midha |
| 6,569,463 B2 | 5/2003 | Patel |
| 6,605,300 B1 | 8/2003 | Burnside |
| 6,627,635 B2 | 9/2003 | Palermo |
| 6,635,284 B2 | 10/2003 | Mehta |
| 6,667,058 B1 | 12/2003 | Goede |
| 6,670,058 B2 | 12/2003 | Murador |
| 6,673,367 B1 | 1/2004 | Goldenheim |
| 6,696,088 B2 | 2/2004 | Oshlack |
| 6,730,325 B2 | 5/2004 | Devane |
| 6,913,768 B2 | 7/2005 | Couch |
| 6,919,373 B1 | 7/2005 | Lam |
| 6,923,988 B2 | 8/2005 | Patel |
| 6,939,029 B1 | 9/2005 | Stahel |
| 6,974,591 B2 | 12/2005 | Kendrup |
| 7,067,116 B2 | 6/2006 | Bess |
| 7,070,806 B2 | 7/2006 | Oshlack |
| 7,083,808 B2 | 8/2006 | Goldenheim |
| 7,115,631 B2 | 10/2006 | Zeitlin |
| 7,125,563 B2 | 10/2006 | Kumbhani |
| 7,144,587 B2 | 12/2006 | Oshlack |
| 7,153,497 B2 | 12/2006 | Hughes |
| 7,510,729 B2 | 3/2009 | Kolter |
| 7,611,730 B2 | 11/2009 | Bartholomaus |
| RE41,148 E | 2/2010 | Burnside |
| 7,691,880 B2 | 4/2010 | Herman |
| 7,776,917 B2 | 8/2010 | Mickle |
| RE42,096 E | 2/2011 | Burnside |
| 7,906,145 B2 | 3/2011 | Castan |
| 8,062,667 B2 | 11/2011 | Mehta |
| 8,202,537 B2 | 6/2012 | Mehta |
| 8,202,542 B1 | 6/2012 | Mehta |
| 8,287,848 B2 | 10/2012 | Mehta |
| 8,287,903 B2 | 10/2012 | Mehta |
| 8,337,890 B2 | 12/2012 | Mehta |
| 8,343,546 B2 | 1/2013 | Hall |
| 8,465,765 B2 | 6/2013 | Mehta |
| 8,470,375 B1 | 6/2013 | McMahen |
| 8,491,935 B2 | 7/2013 | Mehta |
| 8,512,688 B2 | 8/2013 | Mehta |
| 8,563,033 B1 | 10/2013 | Mehta et al. |
| 8,597,684 B2 | 12/2013 | Mehta |
| 8,709,491 B2 | 4/2014 | Tengler |
| 8,747,902 B2 | 6/2014 | Mehta et al. |
| 8,778,390 B2 | 7/2014 | Mehta |
| 8,790,700 B2 | 7/2014 | Mehta et al. |
| 8,840,924 B2 | 9/2014 | Tengler |
| 8,883,217 B2 | 11/2014 | Mehta et al. |
| 8,956,649 B2 | 2/2015 | Mehta |
| 8,999,386 B2 | 4/2015 | Tu |
| 9,017,731 B2 | 4/2015 | Tengler |
| 9,040,083 B2 | 5/2015 | Mehta |
| 9,057,675 B2 | 6/2015 | Tengler |
| 9,072,680 B2 | 7/2015 | Tengler |
| 9,089,496 B2 | 7/2015 | Tengler |
| 9,180,100 B2 | 11/2015 | Tu |
| 9,180,104 B2 | 11/2015 | Nelson et al. |
| 9,198,864 B2 | 12/2015 | Mehta |
| 9,265,737 B2 | 2/2016 | Tengler |
| 9,295,642 B2 | 3/2016 | Tu |
| 2001/0038852 A1 | 11/2001 | Kolter |

(56) References Cited

U.S. PATENT DOCUMENTS

| | | |
|---|---|---|
| 2001/0038853 A1 | 11/2001 | Kolter |
| 2001/0046472 A1 | 11/2001 | Steiner |
| 2002/0058061 A1 | 5/2002 | Midha et al. |
| 2002/0156133 A1 | 10/2002 | Bartholomaeus |
| 2003/0004177 A1 | 1/2003 | Kao |
| 2003/0099711 A1* | 5/2003 | Meadows ............ A61K 9/1641 424/474 |
| 2003/0185873 A1 | 10/2003 | Chasin |
| 2004/0052849 A1 | 3/2004 | O'hare |
| 2004/0059002 A1 | 3/2004 | Couch |
| 2004/0096501 A1 | 5/2004 | Vaya |
| 2004/0126428 A1 | 7/2004 | Hughes |
| 2004/0131680 A1 | 7/2004 | Goldenheim et al. |
| 2004/0220277 A1 | 11/2004 | Couch |
| 2004/0228830 A1 | 11/2004 | Hirsh |
| 2005/0003005 A1 | 1/2005 | Shimizu |
| 2005/0013792 A1 | 1/2005 | Hollenbeck |
| 2005/0013857 A1 | 1/2005 | Fu |
| 2005/0019393 A1 | 1/2005 | Augsburger |
| 2005/0036977 A1 | 2/2005 | Gole |
| 2005/0106246 A1 | 5/2005 | Byrd |
| 2005/0142097 A1 | 6/2005 | Deepak |
| 2005/0181050 A1* | 8/2005 | Hirsh ................... A61K 9/5026 424/469 |
| 2005/0232986 A1 | 10/2005 | Brown |
| 2005/0232987 A1 | 10/2005 | Brown |
| 2005/0265955 A1 | 12/2005 | Raman |
| 2005/0266032 A1 | 12/2005 | Srinivasan |
| 2006/0018933 A1 | 1/2006 | Vaya |
| 2006/0018934 A1 | 1/2006 | Vaya |
| 2006/0029664 A1 | 2/2006 | Srinivasan |
| 2006/0057205 A1 | 3/2006 | Srinivasan |
| 2006/0115529 A1 | 6/2006 | Jeong |
| 2006/0134148 A1 | 6/2006 | Hollenbeck |
| 2006/0134207 A1 | 6/2006 | Srinivasan |
| 2006/0135777 A1 | 6/2006 | Trafelet |
| 2006/0193877 A1 | 8/2006 | Tengler |
| 2006/0204587 A1 | 9/2006 | Kolter |
| 2006/0240105 A1 | 10/2006 | Devane |
| 2006/0240128 A1 | 10/2006 | Schlagheck |
| 2006/0263431 A1 | 11/2006 | Maloney |
| 2006/0286174 A1 | 12/2006 | Raman |
| 2007/0042955 A1 | 2/2007 | Mickle |
| 2007/0059270 A1 | 3/2007 | Hall |
| 2007/0092553 A1 | 4/2007 | Tengler |
| 2007/0140983 A1 | 6/2007 | Hall |
| 2007/0148239 A1 | 6/2007 | Hall |
| 2007/0160675 A1 | 7/2007 | Devane |
| 2007/0215511 A1 | 9/2007 | Mehta |
| 2007/0218140 A1 | 9/2007 | Tanabe |
| 2007/0264323 A1 | 11/2007 | Shojaei |
| 2008/0064694 A1 | 3/2008 | Heil |
| 2008/0075769 A1 | 3/2008 | Poestges |
| 2008/0118570 A1 | 5/2008 | Liu |
| 2008/0118571 A1 | 5/2008 | Lee |
| 2008/0260845 A1 | 10/2008 | Thassu |
| 2009/0011027 A1 | 1/2009 | Pathak |
| 2009/0176884 A1 | 7/2009 | Dickerson |
| 2009/0220611 A1 | 9/2009 | Dargelas |
| 2009/0221552 A1 | 9/2009 | Teicher |
| 2010/0104621 A1 | 4/2010 | Waldo |
| 2010/0166858 A1 | 7/2010 | Mehta |
| 2010/0260844 A1 | 10/2010 | Scicinski |
| 2010/0278901 A1 | 11/2010 | Tengler et al. |
| 2011/0117205 A1 | 5/2011 | Castan et al. |
| 2011/0262539 A1 | 10/2011 | Bosse |
| 2012/0015030 A1 | 1/2012 | Mehta |
| 2012/0135077 A1 | 5/2012 | Mehta |
| 2012/0148672 A1 | 6/2012 | Mehta |
| 2013/0004452 A1 | 1/2013 | Mehta |
| 2013/0004571 A1 | 1/2013 | Mehta |
| 2013/0079415 A1 | 3/2013 | Vergnault |
| 2013/0136797 A1 | 5/2013 | Mehta |
| 2013/0236554 A1 | 9/2013 | Tengler |
| 2013/0243689 A1 | 9/2013 | Tengler |
| 2013/0243869 A1 | 9/2013 | Tengler |
| 2013/0243871 A1 | 9/2013 | Tengler |
| 2014/0023705 A1 | 1/2014 | Tengler |
| 2014/0030348 A1 | 1/2014 | Tengler |
| 2014/0033806 A1 | 2/2014 | McMahen |
| 2014/0037728 A1 | 2/2014 | Tengler |
| 2014/0050796 A1 | 2/2014 | Tengler |
| 2014/0093578 A1 | 4/2014 | Mehta |
| 2014/0127306 A1 | 5/2014 | Mehta |
| 2014/0212493 A1 | 7/2014 | Mehta et al. |
| 2014/0287038 A1 | 9/2014 | Mehta |
| 2014/0287041 A1 | 9/2014 | Tu |
| 2015/0024059 A1 | 1/2015 | Mehta et al. |
| 2015/0157574 A1 | 6/2015 | Tu |
| 2015/0182469 A1 | 7/2015 | Mehta et al. |
| 2016/0008312 A1 | 1/2016 | Nelson et al. |
| 2016/0143846 A1 | 5/2016 | Tu |
| 2016/0143854 A1 | 5/2016 | Tu et al. |
| 2016/0158373 A1 | 6/2016 | Mehta |

FOREIGN PATENT DOCUMENTS

| | | |
|---|---|---|
| CN | 1179450 | 4/1998 |
| DE | 2246037 | 4/1974 |
| EP | 0294103 | 12/1988 |
| EP | 0367746 | 5/1990 |
| EP | 0565301 | 10/1993 |
| EP | 0943341 | 9/1999 |
| EP | 1186293 | 3/2002 |
| EP | 1240897 | 9/2002 |
| EP | 1429728 | 6/2004 |
| GB | 1358001 | 6/1974 |
| JP | 01-287270 | 7/1990 |
| JP | H02-17912 | 7/1990 |
| JP | 05-279246 | 10/1993 |
| JP | H05-279247 | 10/1993 |
| JP | 2003-528910 | 9/2003 |
| JP | 2005-528910 | 9/2005 |
| JP | 2005-306778 | 11/2005 |
| WO | WO87/00044 | 1/1987 |
| WO | WO-1998-014168 | 4/1988 |
| WO | WO1998/014168 | 4/1988 |
| WO | WO90/09168 | 8/1990 |
| WO | WO1992/011871 | 7/1992 |
| WO | WO1998/027961 | 7/1998 |
| WO | WO2000/040224 | 7/2000 |
| WO | WO2001/070194 | 9/2001 |
| WO | WO2001/74336 | 10/2001 |
| WO | WO2003/020242 | 3/2003 |
| WO | WO2004/028267 | 4/2004 |
| WO | WO2004/060357 | 7/2004 |
| WO | WO2004/067039 | 8/2004 |
| WO | WO2004/071501 | 8/2004 |
| WO | WO2005/102269 | 11/2005 |
| WO | WO2005/117843 | 12/2005 |
| WO | WO2006/022996 | 3/2006 |
| WO | WO2006/061700 | 6/2006 |
| WO | WO2006/093938 | 9/2006 |
| WO | WO2006/101536 | 9/2006 |
| WO | WO2006/135362 | 12/2006 |
| WO | WO2007/000779 | 1/2007 |
| WO | WO2007/001300 | 1/2007 |
| WO | WO2007/109104 | 9/2007 |
| WO | WO2008/064163 | 5/2008 |
| WO | WO2010/080787 | 7/2010 |
| WO | WO2012/112140 A1 | 8/2012 |
| WO | WO2013/006322 | 1/2013 |

OTHER PUBLICATIONS

Dashevsky, International Journal of Pharmaceutics, 279, 2004.*
Shao, AAPS PharmSciTech, 2002.*
MeshMicronSizes, 2015.*
L. Allen et al., Ansel's Pharmaceutical Dosage Forms and Drug Delivery Systems, 8th ed., 2005, Section II, Drug Dosage Form and Drug Delivery System Design, Chapter 4, pp. 92-141, Chapter 9, "Solid Oral Modified-Release Dosage Forms and Drug Delivery Systems", pp. 260-275, Lippincott Williams & Wilkins.

(56) References Cited

OTHER PUBLICATIONS

T. Aoyama, "Kinetic analysis of enantiomers of threo-methylphenidate and its metabolite in two healthy subjects after oral administration as determined by a gas chromatographic-mass spectrometric method", J. of Pharmaceutical Sciences, 79(6):465-469 (Jun. 1990).

J. Biederan, "New Generation Long-Acting Stimulants for the Treatment of Attention-Deficit/Hyperactivity Disorder", Medscape Psychiatry, 8(2) (Nov. 2003).

*FDA Accepts Tris Pharma, Inc 's ANDA with Paragraph IV Certification for a Generic Equivalent to Delsym*, BioSpace (Press Release, Jul. 16, 2009, 8:24AM), http://www.biospace.com/News/fda-accepts-U-is-phaima-inc-s-anda-withparagraph/150247.

B. Birmaher, et al., Sustained Release Methylphenidate: Pharmacokinetic Studies in ADDH Males, J. Am. Acad. Child Adolesc. Psychiatry, 28(5):768-772 (1989).

R. Bodmeier, et al., Compaction of Controlled-Release Pellets, BASF ExAct, 4: Apr. 1-4, 2000.

S. Borodkin, et al., Interaction of Amine Drugs with a Polycarboxylic Acid Iona-Exchange Resin, Journal of Pharmaceutical Sciences, 59(4):481-486 (1970).

S. Borodkin, Ion Exchange Resins and Sustained Release, Encyclopedia of Pharmaceutical Technology 8:203-216 (1993).

Chilukuri, et al., Pharmaceutical Product Development: In Vitro-In Vivo Correlation, vol. 165: 110-115 (2007).

Clinical Pharmacology and Biopharmaceutics Review(s), App. No. 21-121 Pharmacology (CONCERTA®), Center for Drug Evaluation and Research, pp. 1-112, Approval Date: Apr. 1, 2000; Date created: Jun. 18, 2001; https://www.accessdata.fda.gov/drugsatfda_docs/nda/2000/21-121_Concerta_biopharmr.pdf.

CONCERTA®, Drug Approval Package, Drugs@FDA, App. No. 21-121, Approval Date: Aug. 1, 2000; Date created: Jun. 18, 2001; https://www.accessdata.fda.gov/-drugsatfda_docs/nda/2000/21-121_Concerta.cfm, pp. 1-5.

D. F. Connor, et al., New Formulations of Stimulants for ADAH, CNS Drugs, 18(14) :1011-1030 (2004).

K. A. Connors et al., Chemical Stability of Pharmaceuticals: A Handbook for Pharmacists, John Wiley & Sons, 2nd ed., 586-591 (1986).

J. Daruwala, Chewable Tablets, in Pharmaceutical Dosage Forms: Tablets, edited by H. Lieberman and L. Lachman, Marcel Dekker, Inc., New York (1980).

N. G. Das and S.K. Das, Controlled-Release of Oral Dosage Forms, Formulation, Fill & Finish (2003).

C. Davis, "Effects of Liquid Methylphenidate on Academic Achievement in ADHD Elementary School Children," Kalamazoo College Thesis (Fall 2009).

K. Dorfner, Ion Exchangers: Properties and Applications, edited by A. F. Coers, Ann Arbor Science Publishers Inc., 1972.

NextWave Pharmaceuticals and Tris Pharma Enter into CNS: focused Development and Commercialization Agreement, FierceBiotech (Aug. 18, 2010) http ://www.fiercebiotech.com/biotech/nextwave-pharmaceuticals-and-tris-pharma-enter-into-cns-focused-development-and.

Guidance for Industry: Extended Release Oral Dosage Forms: Development, Evaluation, and Application of In Vitro/In Vivo Correlations, FDA, 1-24 (1997).

Gibaldi & Penier, Pharmacokinetics, Appx. 4, 15th ed., (1975).

Goodman & Gillman's, The Pharmacological Basis of Therapeutics, 11th ed., edited by L. Brunton et al. (2006).

G. Green et al., Pharmacopeial Standards for the Subdivision Characteristics of Scored Tablets, Pharmacopeial Forum, 35(6):1598-1612[Nov.-Dec. 2009].

X. Guo et al., Ion-Exchange Resins as Drug Delivery Carriers, J. Pharm. Sci. 98(11):3886-3902 (2009).

N. H. G. Holford et al., Understanding the Dose-Effect Relationship: Clinical Application of Pharmacokinetic-Pharmacodynamic Models, Clinical Pharmacokinetics, 6:429-453 (1981).

S. H. Jeong, et al., Drug loading and release properties in ion-exchange resin complexes as a drug delivery matrix, International Journal of Pharmaceutics, 361:26-32 (2008).

L. Lachman et al, "Kinetic Principles and Stability Testing," in The Theory and Practice of Industrial Pharmacy, 3rd ed., Ch. 26 (1986).

FDA accepts Tris Pharma 's two NDAs for OralXR platform -based drugs, Clinical Pharmacology and Biopharmaceutics Review(s), App. No. 21-259 (METADATE CD®), Center for Drug Evaluation and Research.

RONDEC® Syrup, Last Reviewed Apr. 9, 2009, http://www.rxlist.com/rondec-drug.htmm accessed May 31, 2017.

Metadate CD, Center for Drug Evaluation and Research, Application No. 21-259, Drug Approval Package, Drugs@FDA, Approval date: Apr. 30, 2001, Date Created: Apr. 4, 2002, https://www.accessdata.fda.gov/-drugsatfda docs/nda/2001/21-259 Metadate.cfm.

Approval letter, App. No. 21-259 (METADATE CD®), Center for Drug Evaluation and Research, Drugs@FDA. Approval date: Apr. 30, 2001, Date Created: Apr. 4, 2002, https://www.accessdata.fda.gov/-drugsatfda_docs/nda/2001/21-259_Metadate.cfm.

Medical Review(s), App. No. 21-259 (METADATE CD®), Center for Drug Evaluation and Research, Drugs @FDA, Approval date: Apr. 30, 2001, Date Created: Apr. 4, 2002, https://www.accessdata.fda.gov/-drugsatfda_docs/nda/2001/21-259_Metadate.cfm.

Approval Letter, App. No. 21475 (Methylin® Chewable Tablets), Center for Drug Evaluation and Research, Drugs@FDA, Approval Date: Apr. 15, 2003, Date created: Jul. 25, 2006, https://www.accessdata.fda.gov/-drugsatfda_docs/nda/2003/021475s000_MethylinTOC.cfm.

Methylin® Chewable Tablets Label, marketed by Mallinckrodt Inc. (rev. Apr. 2003), https://www.accessdata.fda.gov/drugsatfda_docs/label/2003/21475_methylin_Ibl.pdf, Approval Date: Apr. 15, 2004; date created Jul. 25, 2006.

METHYLIN® Oral Solution label, marketed by Mallinckrodt Inc. (rev. May 2006), https://www.accessdata.fda.gov/drugsatfda_docs/label/2006/021475s002,021419s0031b1.pdf.

Focalin XR Drug Approval Package, Drugs@FDA, Approval Date: May 26, 2005; date created: Jul. 2, 2007, https://www.accessdata.fda.gov/drugsatfda docs/-nda/2005/021802s000TOC.cfm.

Methylin Oral Solution Drug Approval Package, Drugs@FDA, Application No. 021419, Approval date: Dec. 19, 2002; Date Created: Oct. 26, 2004; https://www.accessdata.fda.gov/drugsatfda_docs/nda/2002/21-419_Methylin.cfm.

Press Release, Alliant Pharmaceuticals , Inc., Making ADHD Meds Easier to Swallow (Sep. 7, 2004).

K. S. Patrick et al., New Methylphenidate Formulations for the Treatment of Attention Deficit/Hyperactivity Disorder, Exp. Opin. Drug. Deliv., 2:121-143 (2005).

The Physicians' Desk Reference, (61st ed. 2007) RITALIN® LA, 2271-74.

The Physicians' Desk Reference, (61st ed. 2007) RITALIN® SR, 2269-71.

The Physicians' Desk Reference, (65th ed. 2011) CONCERTA®, 2678-84.

The Physicians' Desk Reference, (65th ed. 2011) FOCALIN® XR, 2530-36.

The Physicians' Desk Reference, (65th ed. 2011) METADATE CD®, 3260-64.

The Physicians' Desk Reference, (64th ed. 2010) TUSSIONEX®, 3443-3444.

Tris Pharma Announces Approval of First-Ever Generic of Tussionex Extended Release Suspension, Pipeline Review (Oct. 7, 2010) http://www.pipelinereview.com/-index.php/2010100737478/Mo re-News/Tris-Pharma-Announces-Approval-of-First-Ever-Generic-of-Tussionex-Extended-Release-Suspension.html.

PR Newswire: Tris Pharma Announced Acceptance of Its First Two NDAs (2009).

Clinical Pharmacology and Biopharmaceutics Review(s), App. No. 202100 (QUILLIVANT® XR), Center for Drug Evaluation and Research, Approval date: Sep. 27, 2012; Date created: Jul. 8, 2013, https://www.accessdata.fda.gov/drugsatfda_docs/-nda/2012/202100Orig1s000ClinPharmR.pdf.

(56) References Cited

OTHER PUBLICATIONS

QUILLIVANT® XR label, marketed by NextWave Pharmaceuticals, Inc. (rev. Sep. 2012), https://www.accessdata.fda.gov/drugsatfda_docs/label/2012/202100lb1.pdf.
Medical Review(s), App. No. 202100 (QUILLIVANT® XR) Center for Drug Evaluation and Research, Approval date: Sep. 27, 2012; Date created: Jul. 8, 2013, https://www.accessdata.fda.gov/drugsatfda_docs/-nda/2012/202100Orig1s000MedR.pdf.
Ritalin LA Drug Approval Package, Drugs@FDA, Application No. 21-284, Approval Date: Jun. 5, 2002, Date created: May 13, 2005; https://www.accessdata.fda.gov/-drugsatfda_docs/nda/2002/21-284_Ritalin.cfm.
Approval Letter, App. No. 21-284 (RITALIN LA®), Center for Drug Evaluation and Research, Application No. 21-284, Approval Date: Jun. 5, 2002, Date created: May 13, 2005; https://www.accessdata.fda.gov/drugsatfda_docs/nda/2002/21-284_Ritalin%20LA_Approv.pdf.
RITALIN-SR® label, marketed by Novartis (rev. Apr. 2007), https://www.accessdata.fda.gov/-drugsatfda_docs/label/2007/010187s069,018029s040,021284s0111b1.pdf.
Ritalin-SR Drug Approval Package, Drugs@FDA. NDA 018029, rev Apr. 2007, http://www.accessdata.-fda.gov/scripts/cder/drugsatfda/index.cfm?fuseaction=Search.Label_ . . . , accessed May 3, 2016, pp. 1-48.
M. Rochdi et al., Dose-Proportional Pharmacokinetics of a Methylphenidate Extended-Release Capsule, Int. J.Clin. Phrumacol. and Therapeutics, 42(5):285-292 (2004).
R. Schachar, et al., Cognitive and behavioral effects of multilayer-release methylphenidate in the treatment of children with attention-deficit/hyperactivity disorder, J. Child Adoles. Psychopharmacol., 18:11-24 (2008).
I. Singh, et al, Ion-Exchange Resin Complexation: Masking the Bitter Taste of Cefuroxime Axetil, Revista Cubana de Fannacia, 45(2):171-180 (2011).
N. R. Srinivas, et al., Enantioselective pharmacokinetics and pharmacodynamics of dl-threo-methylphenidate in children with attention deficit hyperactivity disorder, Clin Pha1macol Ther, 52:561-568 (1992).
N. R. Srinivas, et al., Enantiomeric Drug Development: Issues, Considerations, and Regulatory Requirements, Journal of Pharmaceutical Sciences, 9: 1205-12 15 (2001).
J. Swanson, et al., Acute tolerance to methylphenidate in the treatment of attention deficit hyperactivity disorder in children, Clin. Pharm. & Therapeutics, 66(3):295-305 (1999).
Polymers for Controlled Drug Delivery (Peter J. Tarcha, ed., 1991), pp. 223.
The Pharmacopeia of the United States Twenty-fifth Revision {1151} Pharmaceutical Dosage Forms, 2213-25 (2002).
United States Pharmacopeia 32; The National Formulation 27, vol. 1:1-12 (May 1, 2009).
United States Pharmacopeia 32; The National Formulation 27, vol. 3:2949-2950 (May 1, 2009).
FDA approves first 24-hour liquid sustained-release drug, VerusMed (Dec. 7, 2009).
M. Vimala Devi & P. S. S. Krishna Babu, Ion-Exchange Resinates As Controlled Release Drug Delivery Systems, in Advances in Controlled and Novel Drug Delivery, edited by N. K. Jain, CBS Publishers & Distributors, New Delhi (2001).
Handbook of Pharmaceutical Excipients, 2nd ed., edited by A. Wade and P. J. Weller, American Pharmaceutical Association (1994), pp. 84-87, 123-125, 143-148, 215-216, 280-282, 294-298, 519-521, 562-563.
Y. Wang et al., In Vitro Dissolution and In Vivo Oral Absorption of Methylphenidate from a Bimodal Release Formulation in Healthy Volunteers, Biopharm. Drug Dispos. 25:91-98 (2004).
WHO Drug Information, 25(2):139-147 (Jun. 2011), pp. 99, 138-147.
T. Agnese, et al, Comparing Various plasticisers regarding their effect on methacrylic acid/ethyl acrylate copolymer, BASF, $9^{th}$ Central European Symposium on Pharmaceutical Technology, Sep. 20-23, 2012, Dubrovnik, Croatia.
T. A. Khan et al, Mechanical, Bioadhesive Strength and Biological Evaluations of Chitosan films for Wound Dressing, J Pharm Pharmaceut Sci, 3(3); 202-311 (2000).
ExAct, Excipients & Actives for Pharma, No. 12, Jun. 2004, pp. 1-12, published by BASF Aktiengesellschaft, multiple authors.
Quillichew, Center for Drug Evaluation and Research, Approval Package for Application No. 207960Orig1s000, approval date Dec. 4, 2015, Date created: Jul. 19, 2016; pp. 1-8, https://www.accessdata.fda.gov/drugsatfda_docs/-nda/2015/207960Orig1s000Approv.pdf.
Quillichew, Center for Drug Evaluation and Research, Chemistry Review(s) for Application No. 207960Orig1s000, pp. 1-54, approval date Dec. 4, 2015, Date created: Jul. 19, 2016; https://www.accessdata.fda.gov/drugsatfda_ docs/nda/2015/207960Orig1s000ChemR.pdf.
Quillichew, Center for Drug Evaluation and Research, Labeling for Application No. 207960Orig1s000, pp. 1-19, approval date Dec. 4, 2015, Date created: Jul. 19, 2016; https://www.accessdata.fda.gov/drugsatfda_docs/nda/2015/207960Orig1s0001b1.pdf.
Quillichew, NDA Approval, NDA 207960, pp. 1-5, approval date Dec. 4, 2015, Date created: Jul. 19, 2016; https://www.accessdata.fda.gov/drugsatfda_docs/nda/2015/207960Orig1s000TOC.cfm.
Quillichew, Center for Drug Evaluation and Research, Medical Review for Application No. 207960Orig1s000, pp. 1-78, approval date Dec. 4, 2015, Date created: Jul. 19, 2016; https://www.accessdata.fda.gov/-drugsatfda_docs/nda/2015/207960Orig1s000MedR.pdf.
Quillichew, Center for Drug Evaluation and Research, Summary Review for Application No. 207960Orig1s000, pp. 1-6, approval date Dec. 4, 2015, Date created: Jul. 19, 2016; https://www.accessdata.fda.gov/-drugsatfda_docs/nda/2015/207960Orig1s000SumR.pdf.
Quillichew, Label, pp. 1-14, approval date Dec. 4, 2015, Date created: Jul. 19, 2016; https://www.accessdata.fda.gov/-drugsatfda_docs/nda/2015/207960Orig1s000TOC.cfm.
Quillichew, Center for Drug Evaluation and Research, Medical Review for Application Number, approval date Dec. 4, 2015, Date created: Jul. 19, 2016; pp. 1-10, https://www.accessdata.fda.gov/drugsatfda_docs/nda/2015/207960Orig1s000PharmR.pdf.
ASTM & ISO Test Methods for Measuring Properties, DuPontT™ Tyvek®, Dupont USA, http://www.dupont.com/product-and-services/packaging-materials-solutions.pharmaceutical-packaging/branks/tyvek-steril-packaging/articles/measuring~pro . . . , pp. 1-4, accessed May 31, 2017.
T. Agnese et al, Benefiting from the additional Sustained Release Functionality of Polyvinyl Acetate Dispersion applied as Binder in Wet Granulation, $2^{nd}$ Conference in Innovation in Drug Delivery, Oct. 3-6, 2010; Aiz-enProvence, France; T-GEMP/MD307.
Mehta, K, U.S. Appl. No. 60/783,181—Modified Release Formulations Containing Drug-Ion Exchange Resin Complexes, Mar. 16, 2006.
Defendant Actavis Elizabeth LLC's Initial Invalidity Contentions, Tris Pharma, Inc., v. Actavis Elizabeth LLC, C.A. No. 16-603 (GMS) In the United States District Court for the District of Delaware, pp. 1-111, May 17, 2017.
TRIS Answer to Defendants Actavis and Actavis Elizabeth LLC's Counterclaims, Tris Pharma, Inc., v. Actavis Elizabeth LLC, C.A. No. 16-603 (GMS) in the United States District Court for the District of Delaware, Document 13, Filed Sep. 26, 2016, pp. 1-15.
First Amended Complaint, Tris Pharma, Inc., v. Actavis Elizabeth LLC, C.A. No. 16-603 (GMS) In the United States District Court for the District of Delaware, Document 32, Filed Apr. 25, 2017, pp. 1-11.
Defendants Actavis and Actavis Elizabeth LLC's Answer and Defenses, and Actavis Elizabeth LLC's Counterclaims to Plaintiff's First Amended Complaint, Tris Pharma, Inc., v. Actavis Elizabeth LLC, C.A. No. 16-603 (GMS) In the United States District Court for the District of Delaware, Document 35, Filed Apr. 25, 2017, pp. 1-15.
TRIS' Answer to Defendant Actavis Elizabeth's Counterclaims, Tris Pharma, Inc., v. Actavis Elizabeth LLC, C.A. No. 16-603 (GMS) In the United States District Court for the District of Delaware, Document 39, Filed May 9, 2017, pp. 1-8.
Office Action issued on related Israeli Patent Application No. 227734, dated Nov. 1, 2016.

(56) References Cited

OTHER PUBLICATIONS

Final Office Action, dated Aug. 21, 2017, issued on U.S. Appl. No. 15/200,617.
Non-Final Office Action, dated Jul. 14, 2017, issued on U.S. Appl. No. 15/383,474.
*Tris Pharma, Inc.* v. *Actavis Laboratories FL, Inc.*, Memorandum and Opinion, C.A. No. 14-1309-GMS, Document 161, pp. 1-45, Sep. 5, 2017.
Active Ingredients, Ion Exchange Resins-Healthcare, Rohm Haas, pp. 1, www.F:/Heathcare_Website/deliquescence.htm (Feb. 9, 2006).
Amberlite IRP and Duolite AP143 Applications Reference List, Rohm Haas Ion Exchange Resins-Healthcare, www.rohmhaas.com (Dec. 1, 2004).
Amberlite IRP and Duolite AP143 Ion Exchange Resins Bulk Pharmaceutical Chemicals for Finished Dosage Forms, pp. 1-2, Healthcare Website/release_refl.htm (Feb. 2, 2006).
Amberlite IRP and Duolite AP Ion Exchange Resins, Ion Exchange Resins—Healthcare, Rohm Haas, pp. 1, www.F:/Healthcare_Website/formulations_products.htm (Feb. 9, 2006).
Amberlite IRP64 Pharmaceutical Grade Cation Exchange Resin, Product Data Sheet, pp. 1-3 (Sep. 2004).
Amberlite IRP69 Pharmaceutical Grade, 54OES (Feb. 2006).
Amberlite IRP69 Phamaceutical Grade Cation Exchange Resin, Product Data Sheet, pp. 1-4 (Nov. 2004).
Amberlite IRP88 Pharmaceutical Grade Cation Exchange Resin, Product Data Sheet, pp. 1-4 (Nov. 2004).
Quadir, Release Characteristics . . . of selected drugs with a newly developed polyvinyl acetate dispersion, ExAct, 13:4 (Dec. 2004).
Andrist, Comparative Psychotomimetic Effects of Stereoisomers of Amphetamine, Nature, 234:152-153 (Nov. 19, 1971).
Arnold, Levoamphetamine and Dextroamphetamine: Comparative Efficacy in the Hyperkinetic Syndrome, Archives of General Psychiatry, 27:816-822 (Dec. 1972).
Aoyama, Pharmacodynamic Modeling for Change of Locomotor Activity by Methylphenidate in Rats, Pharmaceutical Research, 14(11):1601-1606 (Nov. 1997).
BASF Aktiengesellschaft, Contents, Introduction, pp. 1-13, 2004.
BASF, A New Sustained Release Excipient, ExAct, 3: 2 (Nov. 1999).
BASF Pharma Solutions: Excipients by Trademark, Kollicoat®, BASF website, www.pharma-solutions.basf.com, pp. 1-3 (Dec. 2, 2004).
BASF, Pharmasolutions, Men/PD 130, Correlation of Drug Prevention Through Isolated Films and Coated Dosage forms Based on Kollicoat 30SR, 1999.
BASF, Development of High Functionality Excipients for Immunity and Sustained Release Dos Forms (Sep. 20, 2004).
BASF, Product Catalog (2008).
BASF-Expertise in Health and Nutrition, Sustained Release Excipients, p. 1-13, Kollicoat® SR 30 D, Tackiness of Films as a Function of Type and Concentration of Plasticizer (2007).
Bordawekar, Evaluation of Polyvinyl Acetate Dispersion as a Sustained Release Polymer for Tablets, Drug Delivery, 13(2):121-131 (Mar. and Apr. 2006).
Bordawekar, Evaluation of Kollicoat® SR 30D as a Sustained Release Polymer Dispersion, BASF Corporation, University of Rhode Island, p. 25, AAPS Poster (2002).
Borodkin, Polycarboxylic Avid Ion-Exchange Resin Adsorbates for Taste Coverage in Chewable Tablets, Journal of Pharmaceutical Science 60(10):1523-1527 (Oct. 1971).
Childress, The Single-Dose Pharmacokinetics of NWP06, a Novel Extended- Release Methylphenidate Oral Suspension, Postgraduate Medicine, 122(5):35-41 (Sep. 2010).
Dashevsky, Compression of Pellets Coated with Various Aqueous Polymer Dispersions, International Journal of Pharmaceutics, 279(1-2):19-26 (Jul. 26, 2004).
Dashevsky, Physicochemical and Release Properties of Pellets Coated with Kollicoat SR 30 D, a New Aqueous Polyvinyl Acetate Dispersion for Extended Release, International Journal of Pharmaceutics, 290(1-2):15-23 (Feb. 16, 2005; E-publication: Jan. 6, 2005).
Degussa, Creating Essentials, Specifications and Test Methods for EUDRAGIT® NE 30 D, p. 1-4 (Sep. 2004).
Deliquescent Drugs, Ion Exchange Resins-Healthcare, Rohm Haas, pp. 1, www.F:/Healthcare_Website/deliquescence.htm (Feb. 9, 2006).
Dissolution Enhancement of Poorly Soluble Drugs, Rohm Haas Ion Exchange Resins-Healthcare, pp. 1, www.rohmhaas.com (Dec. 1, 2004).
Draganoiu, Evaluation of the New Polyvinylacetate/Povidone Excipient for Matrix Sustained Release Dosage Forms, Pharm. Ind., 63:624-629 (2001).
Duolite AP143/1093 Pharmaceutical Grade Anion Exchange Resin, Product Data Sheet, pp. 1-3 (Nov. 2004).
Eliminating Polymorphism, Ion Exchange Resins-Healthcare, Rohm Haas, www.F:/Heathcare_Website/polymorph.htm (Feb. 9, 2006).
El-Samaligy, Formulation and Evaluation of Sustained-Release Dextromethorphan Resinate Syrup, Egyptian Journal of Pharmaceutical Sciences, 37(1-6):509-519 (1996).
Erdmann, Coating of Different Drugs with Optimized Kollicoat EMM 30 D Coatings, BASF Aktiengesellschaft, Proceedings of the $26^{th}$ CRS symposium (Jun. 1999), 6313.
Extended Release, RohmHaas Ion Exchange Resins-Healthcare, p. 1, Rohm and Haas website, www.rohmhaas.com (Feb. 9, 2005).
Generic Drug Formulations with Kollicoat® SR 30 D and Kollidon® SR, pp. 1-51, BASF (1999).
Generic Drug Formulations, MEF/EP076 (2007).
Guide-Choosing the Right Functional Polymer, pp. 1, www.F:/HeathcareWebsite/guide.htm (Feb. 9, 2006).
Haddish-Berhane, Modeling Film-Coat Non-Uniformity in Polymer Coated Pellets: A Stochastic Approach, International Journal of Pharmaceutics, 12; 323(1-2):64-71 (Oct. 2006; E-publication Jun. 6, 2006).
Hossel, Cosmetics and Toiletries, 111(8):73 (1976).
Hughes, New Uses of Ion Exchange Resins in Pharmaceutical Formulation, Rohm Haas (2004).
Ichikawa, Use of Ion-Exchange Resins to Prepare 100 µm-Sized Microcapsules with Prolonged Drug-Release by the Wurster Process, International Journal of Pharmaceutics 216:67-76 (Mar. 2001).
Ion Exchange Resins, GB/US (Jan. 2004).
Ion Exchange Resins-Healthcare, Rohm Haas, Frequently Asked Questions, pp. 1-3, www.F:/Heathcare_Website/gaq_print.htm (Feb. 9, 2006).
Improved Dissolution of Poorly Soluble Drugs References, pp. 1, www.F:/Healthcare_Website/Poor_Solubility_refl.htm (Feb. 9, 2006).
Kollicoat SR30D, Technical Information (Jan. 2004, Supercedes Jun. 1999) BASF, MEF/EP 073.
Kollicoat SR30D, Technical Information, Bulletin, MEV96 (Jun. 1999).
Kollicoat SR30D, Technical Information, ME36(e), pp. 1-14 (Jun. 1999).
Kollicoat SR30D, Technical Information, MEMP30(e)-01, pp. 1-13 (Jan. 2004).
Kollicoat®—Film-Coating Technology by BASF, www.pharma-solutions.basf.com, BASF-Expertise in Health and Nutrition, pp. 13 (Dec. 2, 2004).
Kollicoat® SR 30 D, Polyvinyl Acetate Dispersion for Sustained-Release Pharmaceutical Formulations, Technical Information, BASF (Jun. 1999).
Kollicoat® SR 30 D, Tackiness of Films as a Function of Type and concentration of Plasticizer, BASF-Expertise in Health and Nutrition (Dec. 2007).
Kolter, BASF, ExAct, 5:1-5 (Oct. 2000).
Kolter, Coated Drug Delivery Systems Based on Kollicoat® SR 30D, BASF, MEF/EP073 (Spring/Summer 2004).
Kolter, Influence of Additives on the Properties of Films and coated Dosage Forms, BASF ExAct, 5:4 (Oct. 2000).
Kolter, Influence of plasticizers on the Physico-Chemical Properties of Kollicoat® SR 30 D-Films, BASF Aktiengesellschaft (Spring/Summer 2004).
Kolter, Kollicoat® SR 30 D A New Sustained Release Excipient, BASF AG, p. 1 (Nov. 1999).
Kolter, Kollicoat® SR 30 D, Coated Drug Delivery Systems, ExAct, 11:3 (Oct. 2003).

(56) References Cited

OTHER PUBLICATIONS

Markowitz, Advances in the Pharmacotherapy of Attention-Deficit-Hyperactivity Disorder: Focus on Methylphenidate Formulations, Pharmacotherapy, 23(10):1281-99 (posted Oct. 23, 2003).

Mies, BASF, Pharmasolutions, MEMPD 130, Correlation of Drug Permeation Through Isolated Films and Coated Dosage Forms Based on Kollicoat 30SR D/IR, 2004 AAPS Annual Meeting and Exposition (Nov. 7-11, 2004).

Nisar-Ur-Rahman, Differential Scanning Calorimetry and Surface Morphology Studies on Coated Pellets using Aqueous Dispersions, Pakistan Journal of Pharmaceutical Sciences, 18(2):19-23 (Apr. 2005).

Novartis Consumer Health in Canada, DELSYM, www.Novartisconsumerhealth.ca/en/products/delsym.shtml (2003).

Nicotine, Ion Exchange Resins-Healthcare, Rohm Haas, www.F:/HeathcareWebsite/nicotin.htm (Feb. 9, 2006).

Pearnchob, Coating with Extended Release, ExAct, 12:2-5 (Jun. 2004).

Product Literature, Concerta®, (methylphenidate HC1) Extended-release Tablets, (revised Nov. 2010).

Product Literature, Daytrana™ (methylphenidate transdermal system) (revised Dec. 2009).

Product Literature, Focalin™ XR (dexmethylphenidate hydrochloride) extended-release capsules, Novartis Consumer Health, 2004.

Product Literature, Once Daily Metadate CD™ (methylphenidate HC1, USP) Extended-Release Capsules (Feb. 2007).

Product Literature, Ritalin® hydrochloride methylphenidate hydrochloride tablets USP and Ritalin-SR® methylphenidate hydrochloride USP sustained-release tablets (revised Dec. 2010).

Polymorphism References, pp. 1, www.F:/Heathcare_Website/polymorph_references.htm (Feb. 9, 2006).

Publications-Ion Exchange Resins-Healthcare, Rohm Haas, www.F:/Heathcare_Website/publications.htm (Feb. 9, 2006).

Quadir, FDA Excipient Workshop, Development of High Functionality Excipients for Immediate and Sustained Release Dosage Forms (Sep. 20, 2004).

Raghunathan, Sustained-release Drug Delivery System 1: Coated ion-exchange Resin System for Phenylpropanolamine and Other Drugs, Journal of Pharmaceutical Science, 70:379-384 (Apr. 1981).

Reduced Abuse Formulations, Ion Exchange Resins-Healthcare, Rohm Haas, www.F:/Heathcare_Website/reduced_Abuse.htm (Feb. 9, 2006).

Robinson, Sustained and Controlled Release Drug Delivery Systems, Drugs and the Pharmaceutical Sciences, A Series of Textbooks and Monographs, vols. 1-6, pp. 130-210, by Marcel Dekker, Inc., New York and Basel (1978).

Rowe, Materials Used in the Film Coating of Oral Dosage Forms, Critical Reports in Applied Chemistry, 6:1-16 (1984).

Sawicki, Compressibility of Floating Pellets with Verapamil Hydrochloride Coated with Dispersion Kollicoat SR 30 D, European Journal of Pharmaceutics and Biopharmaceutics, 60(1):153-8 (May 2005; E-publication: Jan. 8, 2005).

Jeong, Drug Release Properties of Polymer Coated Ion-Exchange Resin Complexes: Experimental and Theoretical Evaluation, Journal of Pharmaceutical Sciences, pp. 1-15 (Apr. 2006).

Jeong, Development of Sustained Release Fast-melting Tablets Using Ion Exchange Resin Complexes (accepted Nov. 29, 2005), Dissertations Submitted to Purdue University, W. Lafayette, Indiana, UMI #3210729.

Jeong, Evaluation of Drug Release Properties from Polymer Coated Drug/Ion-Exchange Resin Complexes Using Mathematical Simulation and Their Application into Sustained Oral Drug Delivery, Department of Pharmaceutical Chemistry, University of Kansas, Abstract (Jun. 16-18, 2005), pp. 92-105, 114, 141, 169 (Dec. 2005).

Shao, Drug Release Form Kollicoat SR 30D-Coated Nonpareil Beads: Evaluation of Coating Level, Plasticizer Type, and Curing Condition, pp. 1-9, PharmSci Tech, 3(2):article 15 (Jun. 2002).

Shao, Effects of Formulation Variables and Post-Compression Curing on Drug Release from a New Sustained-Release Matrix Material: Polyvinylacetate-Povidone, Pharmaceutical Development and Technology, 6(2):247-254 (2001).

Strübing, Mechanistic Analysis of Drug Release From Tablets with Membrane Controlled Drug Delivery, European Journal of Pharmaceutics and Biopharmaceutics, 66(1):113-9 (Apr. 2007; E-publication: Sep. 28, 2006).

Swarbrick, Suspensions in Remington: The Science and Practice of Pharmacy, 20$^{th}$ Edition, ed. Gennaro, Lippincott, 2000, pp. 316-323.

Tablet Disintegrate, Ion Exchange Resins-Healthcare, Rohm Haas, pp. 1, www.F:/Heathcare_Website/deliquescence.htm (Feb. 9, 2006).

Taste Masking, Ion Exchange Resins-Healthcare, Rohm Haas, pp. 1, www.F:/Heathcare_Website/tastemasking.htm (Feb. 9, 2006).

Taste Masking References, www.F:/Heathcare_Website/taste_refl.htm (Feb. 9, 2006).

Voskoboinikova, Drug Synthesis Methods and Manufacturing Technology, Modern Auxiliary Substances in Tablet Production: Use of High-Molecular-Weight Compounds for the Development of New Medicinal Forms and Optimization of Technological Processes, Pharmaceutical Chemistry Journal, 39(1):22-28 (Jan. 2005).

Ahmann, Placebo-Controlled Evaluation of Amphetamine Mixture-Dextroamphetamine Salts and Amphetamine Salts (Adderall): Efficacy Rate and Side Effects, Pediatrics, 1:1-11 (Jan. 2001).

Prabhu, Comparison of Dissolution Profiles for Sustained Release Resinates of BCS Class 1 Drugs Using USP Apparatus 2 and 4: A Technical Note, AAPS PharmSciTech, 9(3):769-773 (Sep. 2008).

ADDERALL® Product Insert, revised Mar. 2007 and ADDERALL XR® Product Insert (revised Dec. 2013.).

Hinsvark, The oral bioavailability and pharmacokinetics of soluble and resin-bound forms of amphetamine and phentermine in man, Journal of Pharma and BioPharma, 1(4):319-328 (Aug. 1973).

Hadzija, Determination of Hydrocodone in Tussion® Extended-Release Suspension by High-Performance Liquid Chromatography (HPLC), Journal of Forensic Science, 41(5):878-880 (Sep. 1996).

Physician's Desk Reference: Adderall, 51st Ed. (1997).

Lehmann, Coating of Multiparticulates Using Polymeric Solutions, Formulations and Process Considerations, Multiparticulate Oral Drug Delivery, Ghebre-Sellassie, Ed., Marcel Dekker, Inc., NY, 1994.

Remington: The Science and Practice of Pharmacy, 19th Ed., vol. II, pp. 1653-1658 (1995).

Lin, Bioavailability of d-pseudoephedrine and azatadine from a repeat action tablet formulation, Journal of International Medical Research, 10(2):122-125 (1982).

Lin, Comparative bioavailability of d-pseudoephedrine from a conventional d-pseudoephedrine sulfate tablet and from a repeat action tablet, Journal of International Medical Research 10(2):126-128 (1982).

Lasser, Comparative Efficacy and Safety of Lisdexamfetamine Dimesylate and Mixed Amphetamine Salts Extended Release in Adults with Attention Deficit/Hyperactivity Disorder, Primary Psychiatry, 17(9):44-54 (2010).

FDA Guidance for Industry, SUPAC-MR: Modified Release Solid Oral Dosage Forms. Scale-Up and Postapproval Changes: Chemistry, Manufacturing, and Controls; In Vitro Dissolution Testing and In Vitro Bioequivalence Documentation, pp. 1-36 (Sep. 1997).

The United States Pharmacopeia 23, National Formulary 18, pp. 1791-1799 (1995).

Center of Drug Evaluation and Research, Guidance for Industry: Statistical Approaches to Establishing Bioequivalence, pp. 1-45 (Jan. 2001).

Remington: Pharmaceutical Science, 15th Ed., pp. 1618, 1625-1626 (1975).

FDA Guidance for Industry: Specifications: Test Procedures and Acceptance Criteria for New Veterinary Drug Substances and New Medicinal Products: Chemical Substances, pp. 1-35 (Jun. 14, 2006).

Ansel et al. Pharmaceutical Dosage Forms and Drug Delivery Systems, 6$^{th}$ Ed. pp. 213-221. Williams & Watkins. Jan. 1, 1995.

Pelham et al. Once-a-Day Concerta Methylphenidate Verses Three-Times-Daily Methylphenidate in Laboratory and Natural Settings. Pediatrics. vol. 107(6):1-15. Jun. 1, 2001.

Greenhill et al. Double-Blind, Placebo-Controlled Study of Modified-Release Methylphenidate in Children With Attention-Deficit/Hyperactivity Disorder. Pediatrics. vol. 109(3):1-7. Mar. 1, 2002.

(56) References Cited

OTHER PUBLICATIONS

Swanson et al. Comparison of Once-Daily Extended-Release Methylphenidate Formulations in Children With Attention-Deficit/Hyperactivity Disorder in the Laboratory School (The Comacs Study). Pediatrics. vol. 113(3):206-216. Mar. 3, 2004.
Product Literature, Daytrana® (methylphenidate transdermal system), revised Dec. 2009.
CODEPREX®, Product Label, marketed by UCB, Inc., Jun. 21, 2004.
METHYLIN® Oral Solution, Product Label, marketed by Mallinckrodt Inc., May 2006.
METHYLIN® ER, Product Label, marketed by Mallinckrodt Inc., Oct. 2013.
Notice of Paragraph IV Certification from Par Pharmaceuticals, dated Jun. 17, 2015, and "Detailed Statement of the Factual and Legal Bases for Par's Opinion that U.S. Pat. No. 9,040,083 is Invalid, Unenforceable, and/or Will Not Be Infringed.".
Answer to Actavis Laboratories FL, Inc.'s Counterclaims, C.A. No. 14-1309-GMS, dated Dec. 29, 2014.
First Amended Complaint, C.A. No. 14-1309-GMS, dated May 22, 2015.
Defendants Par Pharmaceutical, Inc.'s and Par Pharmaceutical Companies, Inc.'s Answer to First Amended Complaint and Counterclaims, dated Jun. 12, 2015.
Complaint by Tris Pharma, Inc. against Actavis Laboratories FL, Inc., et al., C.A. No. 15-393-GMS, dated May 15, 2015.
Biederman, "New Generation Long-Acting Stimulants for the Treatment of Attention-Deficit/Hyperactivity Disorder", Medscape Psychiatry, vol. 8(2), Nov. 2003.
Cascade et al., "Short-Acting Versus Long-Acting Medications for the Treatment of ADHD", Psychiatry, vol. 5(8):24-27, Aug. 2008.
Chavez et al., "An Update on Central Nervous System Stimulant Formulations in Children and Adolescents with Attention-Deficit/Hyperactivity Disorder", The Annals of Pharmacotherapy, vol. 43(6):1084-1095, Jun. 2009.
CONCERTA®, Clinical Pharmacology and Biopharmaceutics Reviews, App. No. 21-121, Center for Drug Evaluation and Research, Jun. 2000.
CONCERTA®, Medical Reviews, App. No. 21-121, Center for Drug Evaluation and Research, Jul. 1999 (completed Mar. 2000).
Connors et al., Chemical Stability of Pharmaceuticals: A Handbook for Pharmacists (2$^{nd}$ Ed.), John Wiley & Sons, pp. 587-589., Jan. 1986.
Daughton et al., "Review of ADHD Pharmacotherapies: Advantages, Disadvantages, and Clinical Pearls", J. Am. Acad. Child and Adolescent Psychiatry, vol. 48(3):240-248, Mar. 2009.
DAYTRANA®, Clinical Pharamacology and Biopharmaceutics Reviews, App. No. 21-514, Center for Drug Evaluation and Research, Jun. 2005.
DAYTRANA®, Medical Reviews, App. No. 21-514, Center for Drug Evaluation and Research, Feb. 2006.
Ermer et al., "Pharmacokinetic Variability of Long-Acting Stimulants in the Treatment of Children and Adults with Attention-Deficit/Hyperactivity Disorder", CNS Drugs, vol. 24(12):1009-1025, Dec. 2010.
Flynn, "Buffers—pH Control within Pharmaceutical Systems", J. Parenteral Drug Association, vol. 34(2):139-162, Mar. 1980.
FOCALIN® XR, Clinical Pharamacology and Biopharmaceutics Reviews, App. No. 21-802, Center for Drug Evaluation and Research, Jul. 2004.
FOCALIN® XR, Medical Review, App. No. 21-802, Center for Drug Evaluation and Research, Jul. 2004.
Ghuman et al., "Psychopharmacological and Other Treatments in Preschool Children with Attention Deficit/Hyperactivity Disorder: Current Evidence and Practice", J. Child and Adolescent Psychopharmacology, vol. 18(5):413-447, Oct. 2008.
Gonzales et al., "Methylphenidate Bioavailability from Two Extended-Release Formulations", Int'l J. Clinical Pharmacology and Thereapeutics, vol. 40(4):175-184, Apr. 2002.

Kulshreshtha et al. (Eds.), Pharmaceutical Suspensions: From Formulation Development to Manufacturing, Springer Science & Business Media, Jan. 2009.
METADATE CD®, Clinical Pharmacology and Biopharmaceutics Reviews, App. No. 21-259, Center for Drug Evaluation and Research, Mar. 2001.
METADATE CD®, Medical Reviews, App. No. 21-259, Center for Drug Evaluation and Research, Mar. 2000.
METHYLIN® ER, Approval Letter and Reviews, App. No. 75-629, Center for Drug Evaluation and Research, May 2000.
METHYLIN® Oral Solution, Clinical Pharmacology and Biopharmaceutics Reviews, App. No. 21-419, Center for Drug Evaluation and Research, Jul. 2001.
METHYLIN® Oral Solution, Chemistry Reviews, App. No. 21-419, Center for Drug Evaluation Research, May 2002.
METHYLIN® Oral Solution, Medical Reviews, App. No. 21-419, Center for Drug Evaluation and Research, May 2002.
Patrick et al., "Evolution of Stimulants to Treat ADHD: Transdermal Methylphenidate", Human Psychopharmacology, vol. 24(1):1-17, Jan. 2009.
The Physicians' Desk Reference (60$^{th}$ ed.), "RITALIN® LA", pp. 3104-3106, Jan. 2010.
The Physicians' Desk Reference (60$^{th}$ ed.), "CONCERTA®", pp. 2598-04, Jan. 2010.
The Physicians' Desk Reference (60$^{th}$ ed.), "DAYTRANA®", pp. 3283-3289, Jan. 2010.
The Physicians' Desk Reference (60$^{th}$ ed.), "FOCALIN®" XR, pp. 2472-2477, Jan. 2010.
The Physicians' Desk Reference (60$^{th}$ ed.), "METADATE CD®", pp. 3439-3443, Jan. 2010.
The Physicians' Desk Reference (60$^{th}$ ed.), "TUSSIONEX®", pp. 3443-3444, Jan. 2010.
The Physicians' Desk Reference for Non-Prescription Drugs, Dietary Supplements, and Herbs (29$^{th}$ Ed.), "DELSYM®", pp. 602-603, Jan. 2008.
Greenhill et al., "Practice Parameter for the Use of Stimulant Medications in the Treatment of Children, Adolescents, and Adults", J. Am. Acad. Child and Adolescent Psychiatry, vol. 41(2):26S-49S (supplement), Feb. 2002.
Prince, "Pharmacotherapy of Attention-Deficit/Hyperactivity Disorder in Children and Adolescents: Update on New Stimulant Preparations, Atomoxetine, and Novel Treatments", Child and Adolescent Psychiatric Clin N. Am., vol. 15:13-50, Jan. 2006.
Remington, "The Science and Practice of Pharmacy (20$^{th}$ Ed)", pp. 986-994, Jan. 2000.
RITALIN LA®, Clinical Pharmacology and Biopharmaceutics Reviews, App. No. 21-284, Center for Drug Evaluation and Research, Dec. 2001.
RITALIN LA®, Medical Review(s), App. No. 21-284, Center for Drug Evaluation and Research, Nov. 2000.
Swanson et al., "Comparison of Once-Daily Extended Release methylphenidate Formulations in Children With Attention-Deficit/Hyperactivity Disorder in the Laboratory School (The Comacs Study)", Pediatrics, vol. 113(3):206-16, Mar. 2004.
The Pharmacopeia of the United States (25$^{th}$ revision), "Pharmaceutical Dosage Forms", pp. 2213-2225, Nov. 2001.
Wigal et al., "Selection of the Optimal Dose Ratio for a Controlled-Delivery Formulation of Methylphenidate", J. Appl. Research., vol. 3:46-63, Oct. 2003.
IndustrialSpec.com, Mesh & Micron Sizes: Mesh to Micron Conversion Chart, p. 1, Aug. 27, 2015.
METADATE CD®, Product Label, 2013.
METADATE CD® NDA Approval Letter from the Department of Health and Human Services, dated Feb. 2, 2001.
Quillivant® XR, Highlights of Prescribing Information, Label Revised Dec. 2013.
QUILLIVANT® XR NDA Approval Letter from the Department of Health and Human Services, dated Sep. 27, 2012.
FOCALIN® XR, Highlights of Prescribing Information, Label Revised Jan. 2012.
FOCALIN® XR NDA Approval Letter from the Department of Health and Human Services, dated May 26, 2005.

(56) References Cited

OTHER PUBLICATIONS

METHYLIN® ER NDA Approval Letter from the Department of Health and Human Services, dated May 9, 2000.
RITALIN-SR®, Product Label, Dec. 13, 2013.
RITALIN-SR® NDA Approval Letter from the Department of Health and Human Services, dated May 21, 2004.
RITALIN-LA®, Product Label, Dec. 13, 2013.
RITALIN-LA® NDA Approval Letter from the Department of Health and Human Services, dated Jun. 5, 2002.
Adjei et al., Single-dose pharmacokinetics of methylphenidate extended-release multiple layer beads administered as intact capsule or sprinkles versus methylphenidate immediate-release tablets (RITALIN(®)) in healthy adult volunteers, J Child Adolesc Psychopharmacol, vol. 24(10), Dec. 2014, pp. 570-578.
Biederman, J., New-Generation Long-Acting Stimulants for the Treatment of Attention-Deficit/Hyperactivity Disorder, Medscape Psychiatry, vol. 8(2), Nov. 2003, pp. 1-10.
Bright et al., ADHD Perspectives: Current Trends and the Rationale for Transdermal Therapy, Supplement to Pediatric News, Oct. 2013, pp. 1-12.
Cascade et al., Short-acting versus Long-acting Medications for the Treatment of ADHD, Psychiatry(Edgemont), vol. 5(8), Aug. 2008, pp. 24-27.
Childress et al., The use of methylphenidate hydrochloride extended-release oral suspension for the treatment of ADHD, Expert Rev Neurother, vol. 13(9), Sep. 2013, pp. 979-988.
Dahl, T.C., Handbook of Pharmaceutical Excipients ($6^{th}$ Ed.): Ethylcellulose, Pharmaceutical Press, London, Feb. 2009, pp. 262-267.
DAYTRANA® NDA Approval Letter from the Department of Health and Human Services dated Apr. 4, 2006, pp. 1-9.
Ebert et al., The Effects of Increasing Plasma Concentrations of Dexmedetomidine in Humans, Anesthesiology, vol. 93, Aug. 2000, pp. 382-394.
Faraone et al., The worldwide prevalence of ADHD: is it an American condition?, World Psychiatry, vol. 2(2), Jun. 2003, pp. 104-113.
fda.gov, Clinical Pharmacology and Biopharmaceutics Reviews: Concerta, retrieved from http://www.accessdata.fda.gov/drugsatfda_docs/nda/2000/21- 121_Concerta_biopharmr.pdf on Jul. 15, 2016. Jun. 2000, pp. 1-112.
fda.gov, Clinical Pharmacology and Biopharmaceutics Reviews: Methylin, retrieved from http://www.accessdata.fda.gov/drugsatfda_docs/nda/2002/21- 419_Methylin_BioPharmr.pdf on Jul. 14, 2016. Jul. 2001 pp. 1-54.
fda.gov, Drugs@FDA Frequently Asked Questions, retrieved at http://www.fda.gov/Drugs/InformationOnDrugs/ucm075234.htm on Jul. 18, 2016. Last updated Mar. 2015, pp. 1-7.
fda.gov, Methylin® Oral Solution—NDA Approval Letter, retrieved from http://www.accessdata.fda.gov/drugsatfda_docs/appletter/2002/214191tr.pdf on Jul. 15, 2016, Dec. 19, 2002, pp. 1-4.
fda.gov, Orange Book Listing: Metadate CD, retrieved from hftp://www.accessdata.fda.gov/scripts/cder/ob/docs/obdetail.cfm?Appl_No=021259&TABLE1=OB_Rx on Jul. 14, 2016. Apr. 2001, pp. 1-3.
fda.gov, Quillichew—NDA Approval Letter, retrieved from http://www.accessdata.fda.gov/drugsatfda_docs/appletter/2015/207960Orig1s0001tr.pdf on Jul. 8, 2016, Dec. 4, 2015, pp. 1-5.
Greenhill et al., Practice Parameter for the Use of Stimulant Medications in the Treatment of Children, Adolescents, and Adults, Child Adolesc. Psychiatry, vol. 41(2), Feb. 2002, pp. 26S-49S.
Kessler et al., The prevalence and correlates of adult ADHD in the United States: Results from the National Comorbidity Survey Replication, Am J Psychiatry, vol. 163(4), Apr. 2006, pp. 716-723.
Kooij et al., European consensus statement on diagnosis and treatment of adult ADHD: The European Network Adult ADHD, BMC Psychiatry, vol. 10(67), Sep. 2010, pp. 1-24.
Mallinckrodt Inc., Methylin® Oral Solution (product label), retrieved from http://www.accessdata.fda.gov/drugsatfda_docs/label/2013/021419s0071b1.pdf on Jul. 14, 2016. Dec. 2013, pp. 1-16.

Markowitz et al., Advances in the pharmacotherapy of attention-deficit-hyperactivity disorder: focus on methylphenidate formulations, Pharmacotherapy, vol. 23(10), Oct. 2003, pp. 1281-1299.
Nextwave Pharmaceuticals, Inc., "QuilliChew ER—Methylphenidate HC1: Highlights of Prescribing Information", retrieved from http://labeling.pfizer.com/ShowLabeling.aspx?id=2577 on Jul. 8, 2016, Dec. 2015, pp. 1-14.
Patrick et al., Evolution of stimulants to treat ADHD: transdermal methylphenidate, vol. 24(1), Hum Psychopharmacol, Jan. 2009, pp. 1-17.
Patrick et al., Influence of ethanol and gender on methylphenidate pharmacokinetics and pharmacodynamics, Clin Pharmacol Ther, vol. 81(3), Mar. 2007, pp. 346-353.
pdr.net, "FOCALIN® XR", Physician's Desk Reference, retrieved from http://www.pdr.net/drug-summary/Focalin-XR-dexcphenidate-hydrochloride-431.3616 on Jul. 14, 2016. Aug. 2010, pp. 2472-2477.
pdr.net, Ritalin LA, retrieved from http://www.pdr.net/drug-summary/Ritalin-LA-methylphenidate-hydrochloride-1003 on Jul. 14, 2016. Jan. 2006, pp. 1-3.
pdr.net, Tussionex, retrieved from http://www.pdr.net/drug-summary/Tussionex-chlorpheniramine-polistirex-hydrocodone-polistirex-579.2803 on Jul. 14, 2016. Jan. 2010, pp. 1-2.
Pliszka, Practice Parameter for the Assessment and Treatment of Children and Adolescents With Attention-Deficit/Hyperactivity Disorder, The AACAP Work Group on Quality Issues, J. Am. Acad. Child Adolesc. Psychiatry, vol. 46(7), Jul. 2007, pp. 894-921.
Rodriguez-Torres et al., Effect of ribavirin on intracellular and plasma pharmacokinetics of nucleoside reverse transcriptase inhibitors in patients with human immunodeficiency virus-hepatitis C virus coinfection: results of a randomized clinical study, Antimicrob Agents Chemother, vol. 49(10), Oct. 2005, pp. 3997-4008.
Rohm and Haas, Amberlite™ IRP69, Feb. 2006, pp. 1-5.
Schapperer et al., Bioequivalence of Sandoz methylphenidate osmotic-controlled release tablet with Concerta® (Janssen-Cilag), Pharmacol Res Perspect, vol. 3(1), Feb. 2015, pp. e00072.
Stearns et al., Active tamoxifen metabolite plasma concentrations after coadministration of tamoxifen and the selective serotonin reuptake inhibitor paroxetine, J Natl Cancer Inst, vol. 95(23), Dec. 2003, pp. 1758-1764.
Stier et al., Use of partial area under the curve metrics to assess bioequivalence of methylphenidate multiphasic modified release formulations, AAPS J, vol. 14(4), Dec. 2012, pp. 925-926.
Swanson et al., Development of a new once-a-day formulation of methylphenidate for the treatment of attention-deficit/hyperactivity disorder: proof-of-concept and proof-of-product studies, Arch Gen Psychiatry, vol. 60(2), Feb. 2003, pp. 204-211.
The Dow Chemical Company, Ethocel: Ethylcellulose Polymers Technical Handbook, Sep. 2005, pp. 1-28.
Tris Phamra, Inc., Tris Pharma Announces US Patent Grant Covering Platform Technology (OralXR Press Release), retrieved from http://www.trispharma.com/news_New-US-Patent-Grant_Jan2012.php on Jul. 14, 2016. Jan. 2012, p. 1.
Tris Pharma, Inc., LiquiXR™, retrieved from http://www.trispharma.com/technologies_liquiXR.php on Jul. 14, 2016, p. 1.
Tris Pharma, Inc., NextWave Pharmaceuticals Announces Launch of NEXICLON™ XR—First Extended-Release, Once-Daily Clonidine Oral Suspension and Tablet (Press Release), retrieved from http://www.trispharma.com/news_ Nexiclon06Jan2011.php on Jul. 14, 2016. Jan. 2011, pp. 1-2.
Lasser et al, Comparative Efficacy and Safety of Lisdexamfetamine Dimesylate and Mixed Amphetamine Salts Extended Release in Adults with Attention-Deficit/Hyperactivity Disorder, Primary Psychiatry (http://primarypsychiatry.com/authhor/primaryp/), May 21, 2013.
MK Chourasia and SK Jain, Pharmaceutical approaches to colon targeted drug delivery systems, J Pharm Pharmaceutic Sci (www.ualberta.ca/-csps) 6(1): 33-66, 2003.
"DrugFacts: Stimulant ADHD Medications—methylphenidate and Amphetamine", https://www.drugabuse.gov/publications/drugfacts/stimulant-adhd-medications-methylphenidate-amphetamines, revised Jan. 2014, accessed Sep. 1, 2016.

(56) References Cited

OTHER PUBLICATIONS

S M Outram, "The Use of methylphenidate among students: the future of enhancement?" J Med Ethics, 2010: 36: 198-2020, downloaded by http://jme.bmj.com on Sep. 1, 2016.
CJ Teter et al, "Illicit Methylphenidate Use in an Undergraduate student Sample: Prevalence and Risk Factors", Pharmacotherapy, 2003: 23(5): 609-617.
T Spencer et al, "Effiacy of a Mixed Amphetamine Salts of Compound in Adults with Attention-Deficit/Hyperactivity Disorder", Arch Gen Psychiatry, 2001, 58: 775-782.
AS Gehris et al, "Controlled Release of an Opiate Drug Using Ion Exchange Resin", AAPS 2014 Poster Submission downloaded from http:/abstracts.aaps.org/Verify/AAPS2014/PosterSubmssions/W4037. pdf, Sep. 30, 2015.
JS Markowitz et al, "Ethylphenidate Formation in Human Subjects After Administration of a Single Dose of Methylphenidate and Ethanol", Drug Metabolism and Disposiiton, 28: 620-624 (2000).
JS Markowitz et al, "Pharmacokinetics of Methylphenidate After Oral Administration of Two Modified-Release Formulations in Healthy Adults", Clin Pharmacol., 42(4): 393-401 (2003).
HC Kimiko, Pharmacokinetcs and clinical effectiveness of methylphenidate, Clin Pharmacokinet, Dec. 1999; 37 (6): 457-70, Abstract.
NDA20100, Clinical Pharmacology and Biopharmaceutics Review(s), Applicatoin No. 20100Origls000, Center for Drug Evaluation and Research, revised Mar. 21, 2011, http://www.accessdata.fda.gov/drugsatfda_docs/nda/2012/202100Orig1s000ClinPharmR. pdf.
RJ Meyer and AS Hussaain, "FDA's ACPS Meeting, Oct. 2005 Awareness Topic: Mitigating the Risks of Ethanol Induced Dose Dumping from Oral Sustained/Controlled Release Dosage Forms", Oct. 2005, http://www.fda.gov/ohrms/dockets/ac/05/briefing/2005-4187B1_01_08-Alcohol-Induced.pdf.
DYANAVEL™XR product literature, revised Nov. 2015, (accessed at http://www.accessdata.fda.gov/drugsatfda_docs/label/2015/208147s0001b1.pdf) on Sep. 1, 2016.
Chavez et al., An Update on Central Nervous System Stimulant Formulations in Children and Adolescents with Attention-Deficit/Hyperactivity Disorder, The Annals of Pharmacotherapy, vol. 43, Jun. 2009, pp. 1084-1095.
Childress et al., The single-dose pharmacokinetics of NWP06, a novel extended-release methylphenidate oral suspension, Postgrad Med, vol. 122(5), Sep. 2010, pp. 35-41.
Flynn, Buffers-pH Control within Pharmaceutical Systems, Parental Fundamentals, vol. 34(2), Mar. 1980, pp. 139-162.
International Search Report and Written Opinion dated Oct. 1, 2007 and issued in International Patent Application No. PCT/US2007/006572, pp. 1-4.
International Search Report and Written Opinion dated Feb. 22, 2012 and issued in International Patent Application No. PCT/US2011/024873, pp. 1-4.
International Search Report and Written Opinion dated Oct. 21, 2013 and issued in International Patent Application No. PCT/US2013/054930, pp. 1-4.
European Search Report dated Jan. 20, 2012 and issued in European Patent Application No. 11192711.7, pp. 1-4.
Examination Report dated Feb. 1, 2012 issued in European Patent Application No. 11192711.7, pp. 1-5.
Applicant's Response to Feb. 1, 2012 Examination Report filed for European Patent Application No. 11192711.7, dated Mar. 29, 2012, pp. 1-6.
Intention to Grant dated May 23, 2012 issued in European Patent Application No. 11192711.7, pp. 1-78.
Examination Report dated Nov. 26, 2008 issued in European Patent Application No. 07753217.4, pp. 1-2.
Applicant's Response to Nov. 26, 2008 Examination Report (Rules 161 and 162) filed for European Patent Application No. 07753217.4, dated Dec. 17, 2008, pp. 1-16.
Examination Report (Rules 161 and 162) dated Nov. 22, 2010 issued in European Patent Application No. 07753217.4, pp. 1-4.
Applicant's Response to Nov. 22, 2010 Examination Report issued in European Patent Application No. 07753217.4, dated Mar. 25, 2011, pp. 1-21.
Intention to Grant dated Jul. 1, 2011 issued in European Patent Application No. 07753217.4, pp. 1-74.
Examination Report dated Sep. 24, 2013 issued in European Patent Application No. 11705137.5, pp. 1-2.
Applicant's Response to Sep. 24, 2013 Examination Report filed for European Patent Application No. 11705137.5, dated Mar. 10, 2014, pp. 1-17.
Observations by Third Parties dated Sep. 15, 2014 issued in European Patent Application No. 11705137.5, pp. 1-10.
Communication dated Sep. 22, 2014 issued in European Patent Application No. 11705137.5, pp. 1-36.
Applicant's Response to the Sep. 22, 2014 Communication filed for European Patent Application No. 11705137.5, dated Nov. 10, 2014, pp. 1-12.
Examination Report dated Jul. 21, 2015 issued in European Patent Application No. 11705137.5, pp. 1-5.
Applicant's Response to the Jul. 21, 2015 Examination Report filed for European Patent Application No. 11705137.5, dated Oct. 27, 2015, pp. 1-39.
English translation of an Office Action dated Aug. 21, 2012 issued in Japanese Patent Application No. 2009-500494, pp. 1-9.
English translation of an Office Action dated Oct. 8, 2013 issued in Japanese Patent Application No. 2009-500494, pp. 1-2.
Correspondence from the agent regarding an Office Action dated Oct. 20, 2010 issued in Israeli Patent Application No. 194042, pp. 1-8.
Applicant's Response and English translation thereof to the Oct. 20, 2010 Office Action issued in Israeli Patent Application No. 194042, dated Apr. 5, 2011, pp. 1-7.
Office Action dated Mar. 18, 2013 issued Canadian Patent Application No. 2,645,855, pp. 1-3.
Applicant's Response to Mar. 18, 2013 Office Action filed for Canadian Patent Application No. 2,645,855, dated Sep. 18, 2013, pp. 1-54.
Office Action dated Dec. 9, 2013 issued Canadian Patent Application No. 2,645,855, pp. 1-12.
Response to Dec. 9, 2013 Office Action filed for Canadian Patent Application No. 2,645,855, dated Jun. 9, 2014, pp. 1-41.
Examination Report dated Mar. 11, 2014 issued in Indian Patent Application No. 8703/DELNP/2008, pp. 1-6.
Response to Mar. 11, 2014 Examination Report filed for Indian Patent Application No. 8703/DELNP/2008, dated Dec. 30, 2014, pp. 1-14.
First Examiner's Report dated Nov. 28, 2011 issued in Australian Patent Application No. 2007227569, pp. 1-3.
Applicant's Response to the Nov. 28, 2011 First Examiner's Report filed for Australian Patent Application No. 2007227569, dated Aug. 5, 2013, pp. 1-30.
Office Action and English translation thereof dated Jan. 28, 2011 issued in Russian Federation Patent Application No. 2008140944, pp. 1-9.
English translation of a First Office Action dated Feb. 6, 2013 issued in Chinese Patent Application No. 201110371263.X, pp. 1-9.
English translation of a Second Office Action dated Oct. 24, 2013 issued in Chinese Patent Application No. 201110371263.X, pp. 1-9.
English translation of a First Office Action dated Apr. 30, 2010 issued in Chinese Patent Application No. 200780009208.8, pp. 1-4.
English translation of a Notification of Grounds of Refusal dated Aug. 25, 2013 issued in Korean Patent Application No. 10-2008-7024357, pp. 1-8.
English translation of a Notification of Grounds of Refusal dated Apr. 4, 2014 issued in Korean Patent Application No. 10-2008-7024357, pp. 1-6.
Amendment filed for Australian Patent Application No. 2011359405, dated Nov. 25, 2015, pp. 1-30.
Examination Report dated May 19, 2016 issued on Australian Patent Application No. 2011359405.
Communication Pursuant to Rules 161(1) & 162 EPC, dated Apr. 21, 2015, issued on counterpart European Patent Application No. 13752782.6, pp. 1-6.

(56) References Cited

OTHER PUBLICATIONS

Applicant's Response to Apr. 21, 2015 Communication issued on European Patent Application No. 13752782.6, dated Oct. 23, 2015, pp. 1-24.
Office Action dated Nov. 12, 2009 issued in U.S. Appl. No. 11/724,966, pp. 1-24.
Applicant's Response to the Office Action dated Nov. 12, 2009 issued in U.S. Appl. No. 11/724,966, pp. 1-26.
Interview Summary dated Mar. 17, 2010 issued in U.S. Appl. No. 11/724,966, pp. 1-3.
Applicant's Response to Interview Summary dated Mar. 17, 2010 issued in U.S. Appl. No. 11/724,966, pp. 1-9.
Office Action dated Jun. 23, 2010 issued in U.S. Appl. No. 11/724,966, pp. 1-14.
Applicant's Response to the Office Action dated Jun. 23, 2010 issued in U.S. Appl. No. 11/724,966, pp. 1-79.
Office Action dated Nov. 26, 2010 issued in U.S. Appl. No. 11/724,966, pp. 1-15.
Applicant's Response to the Office Action dated Nov. 26, 2010 issued in U.S. Appl. No. 11/724,966, pp. 1-91.
Rule 131 Declaration executed by Drs. Mehta and Tu filed Sep. 23, 2010 in U.S. Appl. No. 11/724,966, pp. 1-54.
Rule 132 Declaration executed by Dr. Tu filed May 25, 2011 in U.S. Appl. No. 11/724,966, pp. 1-35.
Rule 132 Declaration executed by Dr. Kibbe filed May 25, 2011 in U.S. Appl. No. 11/724,966, pp. 1-29.
Notice of Allowance dated Aug. 19, 2011 issued in U.S. Appl. No. 11/724,966, pp. 1-10.
Office Action dated Dec. 9, 2011 issued in U.S. Appl. No. 12/722,857, pp. 1-18.
Applicant's Response to the Office Action dated Dec. 9, 2011 issued in U.S. Appl. No. 12/722,857, pp. 1-19.
Notice of Allowance dated Aug. 30, 2012 issued in U.S. Appl. No. 12/722,857, pp. 1-8.
Office Action dated Dec. 9, 2011 issued in U.S. Appl. No. 13/244,748, pp. 1-65.
Applicant's Response to the Office Action dated Dec. 9, 2011 issued in U.S. Appl. No. 13/244,748, pp. 1-38.
Notice of Allowance dated Apr. 27, 2012 issued in U.S. Appl. No. 13/244,748, pp. 1-16.
Office Action dated Jan. 18, 2013 issued in U.S. Appl. No. 13/666,424, pp. 1-27.
Applicant's Response to the Office Action dated Jan. 18, 2013 issued in U.S. Appl. No. 13/666,424, pp. 1-15.
Notice of Allowance dated May 17, 2013 issued in U.S. Appl. No. 13/666,424, pp. 1-10.
Office Action dated Mar. 21, 2013 issued in U.S. Appl. No. 13/746,654, pp. 1-22.
Applicant's Response to the Office Action dated Mar. 21, 2013 issued in U.S. Appl. No. 13/746,654, pp. 1-139.
Notice of Allowance dated Jul. 31, 2013 issued in U.S. Appl. No. 13/746,654, pp. 1-10.
Office Action dated Nov. 21, 2013 issued in U.S. Appl. No. 14/044,105, pp. 1-15.
Applicant's Response to the Office Action dated Nov. 21, 2013 issued in U.S. Appl. No. 14/044,105, pp. 1-15.
Applicant Initiated Interview Summary dated May 13, 2014 issued in U.S. Appl. No. 14/044,105, p. 1.
Notice of Allowance dated May 13, 2014 issued in U.S. Appl. No. 14/044,105, pp. 1-10.
Office Action dated Dec. 5, 2013 issued in U.S. Appl. No. 14/065,842, pp. 1-18.
Applicant's Response to the Office Action dated Dec. 5, 2013 issued in U.S. Appl. No. 14/065,842, pp. 1-10.
Notice of Allowance dated Apr. 9, 2014 issued in U.S. Appl. No. 14/065,842, pp. 1-10.
Office Action dated Feb. 26, 2014 issued in U.S. Appl. No. 14/155,410, pp. 1-16.
Applicant's Response to the Office Action dated Feb. 26, 2014 issued in U.S. Appl. No. 14/155,410, pp. 1-10.
Notice of Allowance issued on U.S. Appl. No. 14/155,410, dated Jul. 21, 2014, pp. 1-12.
Office Action dated Dec. 23, 2011 issued in U.S. Appl. No. 13/244,706, pp. 1-27.
Applicant's Response Office Action dated Dec. 23, 2011 issued in U.S. Appl. No. 13/244,706, pp. 1 -127.
Office Action dated Jun. 15, 2012 issued in U.S. Appl. No. 13/244,706, pp. 1-19.
Applicant's Response to the Office Action dated Jun. 15, 2012 issued in U.S. Appl. No. 13/244,706, pp. 1-18.
Notice of Allowance dated Aug. 13, 2012 issued in U.S. Appl. No. 13/244,706, pp. 1-11.
Office Action dated Nov. 9, 2012 issued in U.S. Appl. No. 13/611,183, pp. 1-10.
Applicant's Response to the Office Action dated Nov. 9, 2012 issued in U.S. Appl. No. 13/611,183, dated Jan. 10, 2013, pp. 1-26.
Rule 132 Declaration executed by Dr. Tu filed Jan. 10, 2013 in U.S. Appl. No. 13/611,183, pp. 1-10.
Notice of Allowance dated May 10, 2013 issued in U.S. Appl. No. 13/611,183, pp. 1-13.
Notice of Allowance dated Aug. 2, 2013 issued in U.S. Appl. No. 13/905,808, pp. 1-16.
Office Action dated Nov. 21, 2013 issued in U.S. Appl. No. 14/016,384, pp. 1-12.
Applicant's Response to the Office Action dated Nov. 21, 2013 issued in U.S. Appl. No. 14/016,384, pp. 1-15.
Notice of Allowance issued on U.S. Appl. No. 14/016,384, dated May 9, 2014, pp. 1-8.
Non-Final Office Action dated Aug. 1, 2014 issued on U.S. Appl. No. 14/300,580, pp. 1-7.
Response to Aug. 1, 2014 Office Action filed for U.S. Appl. No. 14/300,580, dated Oct. 17, 2014, pp. 1-14.
Notice of Allowance dated Feb. 11, 2015 issued on U.S. Appl. No. 14/300,580, pp. 1-7.
Non-Final Office Action dated Apr. 1, 2015 issued on U.S. Appl. No. 14/624,998, pp. 1-10.
Response to Apr. 1, 2015 Office Action filed for U.S. Appl. No. 14/624,998, dated Jun. 26, 2015, pp. 1-14.
Notice of Allowance dated Sep. 3, 2015 issued on U.S. Appl. No. 14/624,998, pp. 1-8.
Non-Final Office Action dated Nov. 10, 2015 issued on U.S. Appl. No. 14/872,226, pp. 1-6.
Response to Nov. 10, 2015 Office Action filed for U.S. Appl. No. 14/872,226, dated Nov. 24, 2015, pp. 1-8.
Notice of Allowance dated Jan. 12, 2016 issued on U.S. Appl. No. 14/872,226, pp. 1-5.
Report on the Filing or Determination of an Action Regarding a Patent or Trademark dated Oct. 15, 2014, p. 1.
English abstract for Japanese Patent Publication No. 02-172912 dated Jul. 4, 1990, p. 1.
English abstract for Japanese Patent Publication No. 5-279247 dated Dec. 26, 1993, pp. 1-3.
English abstract for Japanese Patent Publication No. 2005-306778 dated Nov. 4, 2005, pp. 1-3.
English abstract for Japanese Patent Publication No. 2003-528910 dated Sep. 30, 2003, p. 1.
Set of claims filed on Mar. 18, 2014 in U.S. Appl. No. 13/844,555, pp. 1-3.
Set of claims filed on May 2, 2014 in U.S. Appl. No. 13/844,537, pp. 1-5.
Set of claims filed on Mar. 18, 2014 in U.S. Appl. No. 13/844,510, pp. 1-3.
Mehta et al., U.S. Appl. No. 14/679,438, filed Apr. 6, 2015.
Nelson et al., U.S. Appl. No. 14/677,073, filed Apr. 2, 2015.
Nelson et al., U.S. Appl. No. 14/830,040, filed Aug. 19, 2015.
Nelson et al., U.S. Appl. No. 14/829,952, filed Aug. 19, 2015.
Nelson et al., U.S. Appl. No. 14/829,971, filed Aug. 19, 2015.
Mehta et al., U.S. Appl. No. 15/200,617, filed Jul. 1, 2016.
Mehta et al., U.S. Appl. No. 15/200,748, filed Jul. 1, 2016.
Mehta et al., U.S. Appl. No. 14/679,427, filed Apr. 6, 2015.
Mehta, U.S. Appl. No. 15/244,430 for "Orally Effective Extended Release :Powder and Aqueous Suspension Product", filed Aug. 23, 2016.

(56) References Cited

OTHER PUBLICATIONS

Mehta, U.S. Appl. No. 15/215,276, for "Orally Effective Extended Release :Powder and Aqueous Suspension Product", filed Jul. 20, 2016.
Kathala, U.S. Appl. No. 15/200,625 for "Methylphenidate Extended Release Chewable Tablet", filed Jul. 1, 2016.
Notice of Paragraph IV Certification from Actavis, dated Sep. 3, 2014 and "Detailed Factual and Legal Bases for Actavis's Paragraph IV Certification that U.S. Pat. Nos. 8,062,667; 8,287,903; 8,465,765; 8,563,033; and 8,778,390 are Invalid, Unenforceable, and/or Not Infringed", pp. 1-23.
Notice of Paragraph IV Certification from Par Pharmaceuticals, dated Dec. 22, 2014, and "Detailed Statement of the Factual and Legal Bases for Par's Opinion that U.S. Pat. Nos. 8,062,667; 8,287,903; 8,465,765; 8,563,033; and 8,778,390 are Invalid, Unenforceable, and/or Not Infringed", pp. 1-69.
Notice of Paragraph IV Certification from Par Pharmaceuticals, dated Apr. 2, 2015, and "Detailed Statement of the Factual and Legal Bases for Par's Opinion that U.S. Pat. No. 8,956,649 is Invalid, Unenforceable, and/or Will Not Be Infringed", pp. 1-28.
Notice of Paragraph IV Certification from Par Pharmaceuticals, dated Jun. 17, 2015, and "Detailed Statement of the Factual and Legal Bases for Par's Opinion that U.S. Pat. No. 9,040,083 is Invalid, Unenforceable, and/or Will Not Be Infringed", pp. 1-24.
Notice of Paragraph IV Certification from Actavis, dated Sep. 9, 2015, and "Detailed Factual and Legal Bases for Actavis's Paragraph IV Certification that U.S. Pat. No. 9,040,083 Is Invalid, Unenforceable and/or Not Infringed", pp. 1-19.
Notification of Certification for U.S. Pat. No. 9,545,399 Pursuant to § 505(j)(2)(B)(iv) of the Federal Food, Drug, and Cosmetic Act with Actavis' Detailed Factual and Legal Basis for Its Paragraph IV Certification that U.S. Pat. No. 9,545,399 Is Invalid, Unenforceable and/or Not Infringed by the Methylphenidate Hydrochloride Products Described in Actavis' ANDA No. 209134, dated Mar. 10, 2017.
Complaint by Tris Pharma, Inc. against Actavis Laboratories FL, Inc. et al., C.A. No. 14-1309-GMS, dated Oct. 15, 2014, pp. 1-17.
Defendant Actavis Laboratories FL, Inc.'s Answer, Defenses, and Counterclaims, C.A. No. 14-1309-GMS, dated Dec. 5, 2014, pp. 1-24.
Answer to Actavis Laboratories FL, Inc.'s Counterclaims, C.A. No. 14-1309-GMS, dated Dec. 29, 2014, pp. 1-7.
First Amended Complaint, C.A. No. 14-1309-GMS, dated May 22, 2015, pp. 1-22.
Defendant Actavis Laboratories FL, Inc.'s Initial Invalidity Contentions, C.A. No. 14-1309-GMS, dated May 27, 2015, pp. 1-152.
Defendants Par Pharmaceutical, Inc.'s and Par Pharmaceutical Companies, Inc.'s Initial Invalidity Contentions, C.A. No. 14-1309-GMS, dated Jun. 10, 2015, pp. 1-199.
Defendants Par Pharmaceutical, Inc.'s and Par Pharmaceutical Companies, Inc.'s Answer to First Amended Complaint and Counterclaims, dated Jun. 12, 2015, pp. 1-49.
Defendant's Par Pharmaceutical, Inc.'s and Par Pharmaceutical Companies, Inc.'s Answer to Second Amended Complaint and Counterclaims, C.A. No. 14-1309-GMS, dated Aug. 24, 2015, pp. 1-57.
Joint Claim Construction Statement and Chart, C.A. No. 14-1309-GMS, dated Sep. 30, 2015, pp. 1-13.
Defendant's Opening Claim Construction Brief, C.A. No. 14-1309-GMS, dated Oct. 30, 2015, pp. 1-15.
Supplemental Joint Claim Construction Brief, C.A. No. 14-1309-GMS, dated Oct. 30, 2015, pp. 1-2.
Tris's Opening Claim Construction Brief, C.A. No. 14-1309-GMS, dated Oct. 30, 2015, pp. 1-21.
Defendant Actavis Laboratories FL, Inc.'s Amended Initial Invalidity Contentions, C.A. No. 14-1309-GMS, dated Jan. 22, 2016, pp. 1-198.
Defendant Actavis Laboratories FL, Inc.'s Final Invalidity Contentions, C.A. No. 14-1309-GMS, dated Feb. 8, 2016, pp. 1-203.
List of Exhibits in Responding Expert Report by Dr. C. Lindsay DeVane, C.A. No. 14-1309-GMS, dated Jun. 21, 2016, pp. 1-5.
List of Exhibits in Responding Expert Report by James John McGough, M.D., M.S., C.A. No. 14-1309-GMS, dated Jun. 21, 2016, pp. 1-5.
List of Exhibits in Responding Expert Report by Dr. Irwin Jacobs, C.A. No. 14-1309-GMS, dated Jun. 21, 2016, pp. 1-6.
Defendant's Post-Trial Proposed Findings of Fact and Conclusions of Law, C.A. No. 14-1309-GMS, dated Mar. 24, 2017, pp. 1-51.
Tris's Proposed Post-Trial Findings of Fact and Conclusions of Law, C.A. No. 14-1309-GMS, dated Mar. 24, 2017, pp. 1-47.
Complaint by Tris Pharma, Inc. against Actavis Laboratories FL, Inc., et al., C.A. No. 15-393-GMS, dated May 15, 2015, pp. 1-10.
Defendant Actavis Laboratories FL, Inc.'s Answer, Affirmative Defenses, and Counterclaims, C.A. No. 15-393-GMS, dated Jun. 12, 2015, pp. 1-15.
Complaint by Tris Pharma, Inc. against Par Pharmaceutical, Inc. et al., C.A. No. 15-0068-GMS, dated Jan. 21, 2015, pp. 1-21.
Defendants Par Pharmaceutical, Inc.'s and Par Pharmaceutical Companies, Inc.'s Answer to Complaint and Counterclaims, C.A. No. 15-0068-GMS, dated Feb. 12, 2015, pp. 1-38.
Answer to Par Pharmaceutical, Inc.'s and Par Pharmaceutical Companies, Inc.'s Counterclaims, C.A. No. 15-0068-GMS, dated Feb. 26, 2015, pp. 1-10.
Complaint by Tris Pharma, Inc. against Actavis Elisabeth LLC and Actavis, Inc., dated Jul. 12, 2016.
Defendants Actavis Elizabeth LLC and Actavis Inc.'s Answer, Defenses, and Counterclaims, C.A. No. 16-603-GMS, dated Sep. 2, 2016.
Tris Answer to Defendants Actavis Elizabeth LLC and Actavis Inc.'s Counterclaims, C.A. No. 16-603-GMS, dated Sep. 26, 2016, p. 1-15.
Defendants Actavis Elizabeth LLC, Teva Pharmaceuticals USA, Inc. and Teva Pharmaceutical Industries, Ltd.'s Answer and Defenses, and Actavis Elizabeth LLC's Counterclaims to Plaintiff's First Amended Complaint, C.A. No. 16-603-GMS, dated Apr. 25, 2017, pp. 1-15.
First Amended Complaint, C.A. No. 16-603-GMS, dated Apr. 25, 2017, pp. 1-11.
Tris' Answer to Defendant Actavis Elizabeth LLC's Counterclaims, C.A. No. 16-603-GMS, filed May 9, 2017, pp. 1-8.
Defendant Actavis Elizabeth LLC's Initial Invalidity Contentions, C.A. No. 16-603-GMS, dated May 17, 2017, pp. 1-111.
Second Amended Complaint for Patent Infringement against Actavis Elizabeth LLC—filed by Tris Pharma Inc., C.A. No. 16-cv-603-GMS Document 120, entered Mar. 20, 2018.
Defendant Actavis Elizabeth LLC's Answer, Affirmative Defenses, and Counterclaims to Plaintiff's Second Amended Complaint, C.A. No. 16-cv-603-GMS, Document 124, entered Mar. 28, 2018.
Tris Answer to Defendant Actavis Elizabeth LLC's Counterclaims, C.A. No. 16-cv-00603-KAJ, Document 125, entered Apr. 4, 2018.
US Court of Appeals for the Federal Circuit, *Tris Pharma, Inc.*, v. *Actavis Laboratories FL, Inc.*, Brief for Plaintiff-Appellant, Document 25, Dec. 4, 2017.
US Court of Appeals for the Federal Circuit, *Tris Pharma, Inc.*, v. *Actavis Laboratories FL, Inc.*, Document 26 for Brief for Plaintiff-Appellant, Dec. 4, 2017.
US Court of Appeals for the Federal Circuit, *Tris Pharma, Inc.*, v. *Actavis Laboratories FL, Inc.*, Document 32, Response Brief for the Defendant-Appellee, Feb. 15, 2018.
US Court of Appeals for the Federal Circuit, *Tris Pharma, Inc.*, v. *Actavis Laboratories FL, Inc.*, Document 36 for Reply Brief for Plaintiff-Appellant, Mar. 15, 2018.

\* cited by examiner

MODIFIED RELEASE FORMULATIONS CONTAINING DRUG-ION EXCHANGE RESIN COMPLEXES

BACKGROUND OF THE INVENTION

The present invention relates to pharmaceutical preparations having a drug-ion exchange resin complex that is treated to provide programmable release characteristics in the gastrointestinal tract.

One important aspect of drug therapy is the effect of a drug for an extended time and in many cases, the longer the time, the more substantial the benefit.

Use of ion-exchange resins to form a drug-ion exchange resin complex is well known and is described, for example, in U.S. Pat. No. 2,990,332. In this patent, the use of an ion-exchange resin to form a complex with ionic drugs and thereby delay the drug release from such complexes is described. Such delay in drug release was deemed to be of relatively short duration. Since then there have been additional publications and patents (e.g., U.S. Pat. Nos. 3,138,525; 3,499,960; 3,594,470; Belgian Patent No. 729,827; German Patent No. 2,246,037) that describe use of such ion-exchange resin complexes with water-permeable diffusion barrier coatings of the drug-ion exchange resin complex coated to alter the release of drugs from the drug-ion exchange resin complex.

Sustained or prolonged release dosage forms of various drugs are known and commercially available. However, there are only a few products available that provide sustained release of the drug from the very fine particles of coated drug-ion exchange complexes. A recent US Published Patent Application No. US 2005/0181050 A1, published Aug. 18, 2005, mentions that few modified release liquids containing drug-loaded ion exchange resin particles are commercially available. It further states that such products require several time consuming steps and require the use of a potentially hazardous step of coating from a solvent based solution. The regulatory authorities require that such solvents are thoroughly removed from the pharmaceutical products before ingestion.

Raghunathan in U.S. Pat. Nos. 4,221,778; 4,847,077 and Raghunathan et al. in *J. Pharm. Sci., Vol* 70, pp 379-384, April 1981, describe treating drug-ion exchange resin complexes with water soluble, hydrophilic impregnating (solvating) agents such as polyethylene glycol and others so as to enable the coating of drug-ion exchange resin complexes with a water-permeable diffusion barrier. These publications indicate that the drug-ion exchange resin tended to swell when in contact with water, causing the coating layer to fracture and prematurely release the drug thereby adversely impacting the purpose of the coating (i.e., control release). Attempts to minimize such rupture of the coating layer were made using impregnating (solvating) agents to control the swelling of the drug-ion exchange resin complex. Other patents describing variations of this type of product are referenced in US Published Patent Application No. 2003/0099711 A1, section 0006.

Further, Kelleher et al. in U.S. Pat. No. 4,996,047 describe using a drug content above a specified value in the drug-ion exchange resin complex to avoid the swelling of the drug-ion exchange resin complex and thereby minimizing the rupture of the coating. Umemoto et al., describe in U.S. Pat. No. 5,368,852 that despite the use of impregnating agents, certain preservatives used in the liquid preparation tend to cause the rupture of the diffusion barrier coating of the drug-ion exchange resin complex. Umemoto et al. reported overcoming the rupture of the coating membrane by use of a preservative that did not cause the rupture.

Another patent, U.S. Pat. No. 6,001,392 granted Dec. 14, 1999 describes certain acrylate based (e.g., EUDRAGIT polymer system) and ethyl cellulose (e.g., SURELEASE, AQUACOAT) polymers for coating a drug-ion exchange resin complex using either a solvent or aqueous based coating to achieve sustained release of the drug from the drug-ion exchange resin complex. No meaningful data is disclosed regarding the integrity of the coating film. Further, there is no reported data or evidence of prolonged release of the drug from the coated drug-ion exchange resin complex beyond about 12 hours. A more recently Published Patent Application No. US 2003/0099711 A1, describes using an ethyl cellulose polymer in an aqueous based coating system. This publication further describes use of an enteric coating as an optional added coating to delay the drug release. There have been literature-reported drawbacks of using ethyl cellulose based aqueous dispersions as coatings for drug-ion exchange resin complexes.

Similarly, there have been drawbacks associated with previously used polymers of acrylate and methacrylate-based aqueous dispersion coating systems for coating drug-ion exchange resin complex. Amongst these shortcomings observed is significant tackiness upon application of the coating and during curing, which complicates the coating process of drug-ion exchange resin complexes and/or requires the addition of further components such as an anti-tacking material to counteract this undesirable property.

SUMMARY OF THE INVENTION

The invention provides pharmaceutical preparations comprising drug(s) bound to an ion-exchange resin to provide a drug-ion exchange resin complex, admixing of such complex with a release retardant water-insoluble polymer, and coating of such admixture with a highly flexible, substantially tack-free, non-ionic, water-insoluble, water-permeable diffusion membrane which is preferably aqueous-based and provides a coating membrane that maintains its film integrity, and further provides controllable modified release of the active pharmaceutical(s) in the gastrointestinal tract for a duration of up to about 24 hours.

In one aspect, the present invention provides ingestible pharmaceutical compositions comprising substantially tack free, non-ionic, water-permeable diffusion barrier coatings for drug-ion exchange resin complexes that need not be based upon the use of organic solvents to dissolve the coating composition, do not use either ethyl cellulose or acrylate based polymers compositions or other standard coatings heretofore used for coating ion exchange drug resin complexes, do not require the use of impregnating (solvating) agents, provide excellent integral film coatings, and can provide prolonged, programmable release of drugs from the drug-ion exchange resin complexes of up to about 24 hours.

In another aspect, the present invention provides pharmaceutical compositions comprising water-permeable diffusion barrier coatings for a drug-ion exchange resin complex that are water based, provide highly flexible coatings that are applied in substantially non-tacky form, which facilitates processing of such coatings, in the presence of acceptable plasticizer levels and maintain the coating film integrity and minimize fracturing of the coating layer even after being subjected to severe physical stress, including the compression step of a tableting operation.

In still another aspect, the present invention provides a highly flexible coating that has the potential benefit of reducing the drug-abuse of narcotics or control drug substances. The flexible coating can reduce the ability of the subjects to get instant "high" by making it more difficult to break the barrier coating by chewing or other mechanical means due to the increased resistance of such flexible coating to easy rupture.

In a further aspect, the present invention provides oral pharmaceutical compositions comprising a drug-ion exchange resin complex that does not need an enteric coating to provide prolonged release up to about 24 hours.

In yet another aspect, the present invention provides oral pharmaceutical compositions comprising a drug-ion exchange resin complex that can be formulated to give customizable, programmable release of the one or more drugs from such complexes by combining the application of a release retardant in combination with a water-permeable diffusion barrier coating that is aqueous-based and which are not believed heretofore to have been used for coating films for drug-ion exchange resin complexes.

A further desirable advantage, previously reported when using ion exchange resins, is to provide a reduction of undesirable tastes sometimes associated with an orally ingestible formulation, where unbearable or bad taste of the active drug may be a drawback to the recommended drug ingestion regimen.

Another aspect of the present invention is to provide a method of manufacture of drug-ion exchange resin complexes that provide flexibility, higher drug binding efficiency, and drug loading and processing benefits to produce such complexes.

It has been observed by the inventors that use of heretofore known film coatings of an acrylate-based EUDRAGIT polymer system may lead to agglomeration of the particles during application and/or curing, particularly high-temperature curing. Further, such acrylate-based polymer systems have been observed by the inventors to cause agglomeration and color migration in the presence of colorants in an orally ingestible liquid suspension, upon storage thereof for over about one month. Further, the inventors have observed that ethyl cellulose-based coating systems cause flocculation when in liquid suspension, thereby creating a defective coating system.

Thus, the present invention addresses both art-recognized and what the inventors previously believe are unreported problems associated with prior art drug-ion exchange resin complexes. These and other advantages of the present invention will be apparent from the following detailed description of the invention.

DETAILED DESCRIPTION OF THE INVENTION

The present invention provides a coated drug-ion exchange resin composition for further use in formulation with conventional pharmaceutically acceptable components to provide ingestible compositions. The finished dose compositions may take the form of liquid preparations such as suspensions or solid preparations such as tablets, capsules, liquigels, powders, wafers, strips, etc. In one preferred embodiment, the coating is an aqueous based coating. However, the invention may utilize a non-aqueous, solvent-based system alone (as long as excess solvent is removed), or in conjunction with an aqueous based coating.

Controlled release particles containing pharmaceutically active drug can be manufactured that are coated with an aqueous based system and provide safe products. The use of the water based coatings, the use of a release retardant, and methods of manufacture are disclosed.

The inventors have found that by using a drug-ion exchange resin having a water-permeable diffusion barrier coating as described herein, a prolonged release of drug from the drug-ion exchange resin complex is obtained without the necessary use of water soluble impregnating (solvating) agents as these terms are defined in U.S. Pat. No. 4,221,778.

The drug release pattern from the compositions of the present invention may be further controlled or modified by combining the drug and resin to form the drug-ion exchange resin complex matrix prior to the application of the water-permeable diffusion barrier coating. Water-insoluble polymers useful in the barrier coating include a single polymer or mixtures thereof, such as may be selected from polymers of ethyl cellulose, polyvinyl acetate, cellulose acetate, polymers such as cellulose phthalate, acrylic based polymers and copolymers (such as, for example, those available under EUDRAGIT brand name) or any combination of such insoluble polymers or polymer systems herein defined as a "release retardant". The water-permeable diffusion barrier coating system with or without a "release retardant" may be formulated to achieve the desired length of time of drug release rate from such drug-ion exchange resin complexes. Such coating systems could be further customized by the incorporation of individual or a combination of hydrophilic or lipophilic plasticizers with a dispersion or suspension containing the barrier coating polymer. Such plasticizers include, e.g., propylene glycol, polyethylene glycol, triacetin, triethyl citrate, dibutyl sebacate, vegetable oil, lipids, etc.

Polyvinyl acetate, due to its high tensile strength in the presence of a plasticizer(s), provides a flexible coating film for use as the water-permeable diffusion barrier coating that maintains its film integrity even when subjected to severe physical force and stress such as during a compression step in a tabletting machine or the grinding action of a coffee beans grinder, mill, etc. These coatings even with the addition of a plasticizer remain substantially non-tacky and process-friendly during the coating operation in a Wurster fluid bed or other coating operation and do not cause agglomeration during the coating of very fine particles of drug-ion exchange resins. Agglomeration (sometimes termed "caking" or "brick formation") during a coating operation may otherwise impede the air flow, destroy flow pattern, and/or clog the spray nozzle, thereby increasing the possibility of an imperfect and uneven coating of the drug-ion exchange resin particles.

It has been found that, by employing the compositions described above, it is possible to obtain controlled release compositions that are highly flexible and use a substantially tack-free coating system during coating application and curing. Further, the compositions of the invention do not require the use of an impregnating (solvating) agent to control the swelling or otherwise impede the rupture of the coating membrane. Thus, the compositions of the present invention can provide programmable and prolonged release of drugs from drug-ion exchange resin complexes using the herein described water-based diffusion barrier coating systems.

The term "programmable release" is used to describe a pre-determined release profile of drug from the drug-ion exchange resin complex for up to about 24 hours.

Due to the prolongation of the drug release of up to about 24 hours, the compositions of the present invention have concomitant advantages: instead of taking two or three dosages per day, one may take a once-a-day dose that would provide more consistent supply (release) of the drug that otherwise may have to be taken multiple times a day. This is especially beneficial in the case of small children, elderly people, or others, who have difficulty swallowing larger solid dosage forms such as tablets or capsules.

The coated drug-ion exchange resins of the present invention are formulated into finished ingestible dosage forms such as a liquid suspension or a fast disintegrating tablet that need not be swallowed. It has also been observed that for use in liquid compositions, the film forming coating of the present invention for the drug-ion exchange resin complex when formulated into a liquid suspension does not produce undesirable agglomerations and color migration of the suspended particles in the liquid in the presence of a colorant which is desirably used in medicines to be taken by children. Therefore, such prolonged release compositions may enhance compliance.

As used herein, the term "modified release" refers to compositions of the invention which are characterized by having a drug release from a drug-ion exchange complex of the invention over a period of at least about 8 hours, and preferably up to about 24 hours. For a 24 hour release product, in one aspect, less than 50% of the drug is released from the drug-ion exchange resin complex of the invention at about 12 hours from administration. In another aspect, less than 60% of the drug is released from the drug-ion exchange resin complex of the invention at about 12 hours from administration. In still another aspect, less than 70% of the drug is released from the drug-ion exchange resin complex at about 12 hours. In still other embodiments, less than about 80% or more of the drug is released from the drug-ion exchange resin at about 12 hours. The term "modified release" may include, e.g., compositions which extended release formulations, sustained release formulations, or delay release formulations.

As used herein in reference to numeric values provided herein, the term "about" may indicate a variability of as much as 10%.

A detailed description of the components of the compositions of the present invention follows:

Ion-Exchange Resin

Contemplated within the scope of the invention are pharmaceutically active compounds safe for ingestion, which form a complex with an ion-exchange resin and are manufactured in accordance with Good Manufacturing Practices (GMP) for bulk pharmaceutical chemicals. Typically, these compounds are designed for oral administration and administration via a nasogastric tube.

Ion-exchange resins suitable for use in these preparations are water-insoluble and comprise a preferably pharmacologically inert organic and/or inorganic matrix containing functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are suitable for use in the controlled release of drug preparations. Such ion-exchangers are described by H. F. Walton in "Principles of Ion Exchange" (pp: 312-343) and "Techniques and Applications of Ion-Exchange Chromatography" (pp: 344-361) in Chromatography. (E. Heftmann, editor), van Nostrand Reinhold Company, New York (1975). Ion exchange resins that can be used in the present invention have exchange capacities of about 6 milliequivalents (meq)/gram and preferably about 5.5 meq/gram or below.

Typically the size of the ion-exchange particles is from about 5 microns to about 750 microns, preferably the particle size is within the range of about 40 microns to about 250 microns for liquid dosage forms although particles up to about 1,000 micron can be used for solid dosage forms, e.g., tables and capsules. Particle sizes substantially below the lower limit are generally difficult to handle in all steps of the processing. Generally, uncoated drug-ion exchange resin particles of the invention will tend to be at the lower end of this range, whereas coated drug-ion exchange resin particles of the invention will tend to be at the higher end of this range. However, both uncoated and coated drug-ion exchange resin particles may be designed within this size range.

Commercially available ion-exchange resins having a spherical shape and diameters up to about 1,000 microns are gritty in liquid dosage forms and have a greater tendency to fracture when subjected to drying-hydrating cycles. Moreover, it is believed that the increased distance that a displacing ion must travel in its diffusion into these large particles, and the increased distance the displaced drug must travel in its diffusion out of these large particles, cause a measurable but not readily controlled prolongation of release even when the drug-ion exchange resin complexes are uncoated. Release of drug from uncoated drug-ion exchange resin complexes with particle sizes in the approximate range of 40 microns to 250 microns is relatively rapid. Satisfactory control of the drug release from such complexes is achieved by the applied diffusion barrier coating and can be modified by the inclusion of a release retardant as described herein.

Both regularly and irregularly shaped particles may be used as resins. Regularly shaped particles are those particles that substantially conform to geometric shapes such as spherical, elliptical, cylindrical and the like, which are exemplified by Dow XYS-40010.00 and Dow XYS-40013.00 (The Dow Chemical Company).

Irregularly shaped particles are all particles not considered to be regularly shaped, such as particles with amorphous shapes and particles with increased surface areas due to surface channels or distortions. Irregularly shaped ion-exchange resins of this type are exemplified by Amberlite IRP-69 (Rohm and Haas). Two of the preferred resins of this invention are Amberlite IRP-69 and Dow XYS-40010.00. Both are sulfonated polymers composed of polystyrene cross-linked with about 8% of divinylbenzene, with an ion-exchange capacity of about 4.5 to 5.5 meq/g of dry resin ($H^+$-form). Their essential difference is in physical form. Amberlite IRP-69 consists of irregularly shaped particles with a size range of about 5 microns to about 149 microns produced by milling the parent large size spheres of Amberlite IRP-120. The Dow XYS-40010.00 product consists of spherical particles with a size range of 45 microns to 150 microns.

Other suitable ion-exchange resins include anion exchange resins, such as have been described in the art and are commercially available. These resins are particularly well suited for use with acidic drugs including, e.g., nicotinic acid, mefanimic acid, indomethacin, diclofenac, repaglinide, ketoprofen, ibuprofen, valproic acid, lansoprazole, ambroxol, omeprazole, acetominophen, topiramate, and carbemazepine, pentobarbital, warfarin, triametrene, and prednisolone, as well as prodrugs, salts, isomers, polymorphs, and solvates thereof, as well as other drugs identified herein and/or known in the art.

An example of an anion exchange resin is a cholestyramine resin, a strong base type 1 anion exchange resin powder with a polystyrene matrix and quartemary ammonium functional groups. The exchangeable anion is generally chloride which can be exchanged for, or replaced by, virtually any anionic species. A commercially available Cholestyramine resins is PUROLITE™ A430MR resin. As described by its manufacturer, this resin has an average particle size range of less than 150 microns, a pH in the range of 4-6, and an exchange capacity of 1.8-2.2 eq/dry gm. Another pharmaceutical grade cholestyramine resin is available as DUOLITE™ AP143/1094 [Rohm and Haas], described by the manufacturer as having a particle size in the range of 95%, less than 100 microns and 40%, less than 50 microns. The commercial literature from the suppliers of these and other resin is incorporated herein by reference (PUROLITE A-430 MR; DOW Cholestryramine USP, Form No. 177-01877-204, Dow Chemical Company; DUOLITE AP143/1083, Rohm and Haas Company, IE-566EDS—February 06).

Cation exchange resins, e.g., AMBERLITE IRP-69, are particularly well suited for use with drugs and other molecules having a cationic functionality, including, e.g., acycloguanosine, tinidazole, deferiprone, cimetidine, oxycodone, remacemide, nicotine, morphine, hydrocodone, rivastigmine, dextromethorphan, propanolol, betaxolol, 4-aminopyridine, chlorpheniramine, paroxetine, duloxetine HCl, atomoxetine HCl, risperidone, atovaquone, esmolol, naloxone, phenylpropranolamine, gemifloxacin, oxymorphone, hydromorphone, nalbupherin, and O-desmethylvenlafaxine, as well as prodrugs, salts, isomers, polymorphs, and solvates thereof, as well as other drugs identified herein and/or known in the art. Cationic exchange resins are readily selected for use of these basic drugs or other drugs identified herein and/or are those which are known to those of skill in the art.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfate, and so on by incorporating them at any stage of preparation either before complexation or during complexation or thereafter. These impurities along with their chelating agent to which they have bound may be removed before further treatment of the ion exchange resin with a release retardant and diffusion barrier coating.

Drugs

The drugs that are suitable for use in these preparations in terms of chemical nature are acidic, basic, amphoteric, or zwitterionic molecules. Such drugs include small molecules, and selected larger molecules as well, including chemical moieties and biologicals, such as, e.g., a protein or a fragment thereof (e.g., a peptide, polypeptide, etc), enzyme, antibody or antibody fragment.

The drugs that are suitable for use in these preparations include drugs for the treatment of respiratory tract disorders such as, for example, antitussive expectorants such as dihydrocodeine phosphate, codeine phosphate, noscapine hydrochloride, phenylpropanolamine hydrochloride, potassium guaiacolsulfonate, cloperastine fendizoate, dextromethorphan hydrobromide and cloperastine hydrochloride; bronchodilators such as dl-methylephedrine hydrochloride and dl-methylephedrine saccharinate; and antihistamines such as fexofenadine HCl- or dl-chlorpheniramine maleate. Other drugs useful for the invention include drugs for the treatment of digestive tract disorders such as, for example, digestive tract antispasmodics, including scopolamine hydrobromide, metixene hydrocloride and dicyclomine hydrochloride, drugs for the treatment of central nervous system disorders such as, for example, antipsychotic drugs including phenothiazine derivatives (chlorpromazine hydrochloride, eth.) and phenothiazine-like compounds (chlorprothexene hydrochloride, eth.) antianxiety drugs such as benzodiazepine derivatives (chlordiazepoxide hydrochloride, diazepam, etc.), alprazolam, etc., antidepressants such as imipramine compounds (imipramine hydrochloride, etc.), respiradone, SSRIs like sertraline HCl, paroxitene HCl, venlafaxine HCl, etc., antipyretic analgesics such as sodium salicylate, and hypnotics such as phenobarbital sodium; opioid analgesics drugs such as alfentanil, allyprodine, alphaprodine, anileridne, benzylmorphine, bezitramide, buprenorphine, butorphanol, clonitazene, codeine, cyclazocine, desmorphine, dextromoramide, dexocine, diampromide, dihydrocodeine, dihydromorphine, dimexoxadol, dimepheptanol, dimethylthiambutene, dioxaphetly butyrate, dipipanone, eptazocine, ethoheptazine, ethylmethylthiambutene, ethylmorphine, etonitazene fentanyl, heroin, hydrocodone, hydromorphone, hydroxpethidine, isomethadone, ketobermidone, levallorphan, levorphanol, levophenacylmorphan, lofentanil, meperidine, meptazinol metazocine, methadone, metopon, morphine, morphine sulfate, myrophine, nalbuphine, narceine, cicomorphine, norlevorphanol, nomethadonel nalorphine, normophine, norpipanone, opium, oxycodone, ixmymorphone, papavretum, pentazocine, phenadoxone, phenmorphan, phenazocine, phenoperidine, iminodine, piritamide, propheptazine, promedol, properidine, propiram, proposyphene, sufenanil, tramadol, tiline, salts thereof, mixtures of any of the foregoing, mixed mu-agonists/antagonists, mu-antagonist combinations, and the like; and drugs for the treatment of respiratory system disorders such as, for example, coronary dilators including etafenone hydrochloride, calcium antagonists such as verapamil hydrochloride, hypotensive drugs such as hydrazine hydrochloride, propranolol hydrochloride and clonidine hydrochloride, a peripheral vasodilators/vasoconstrictors such as tolazoline hydrochloride, respiradone, other respiratory agents such as predinisolone, prednisolone sodium phosphate, albuterol, albuterol sulfate, terbutaline, etc. Antibiotics may also be useful including macrolides such as, oleandomycin phosphate, tetracyclines such as tetracycline hydrochloride, streptomycins such as fradiomycin, sulfate, and penicillin drugs such as amoxicillin, dicloxacillin sodium, pivmecillinam hydrochloride and carbenicillinindanly sodium. Chemotherapeutic drugs may also be used including sulfa drugs such as sulfisomidine sodium, antituberculosis drugs such as kanamycin sulfate, and antiprotozoan drugs such as amodiaquine hydrochloride. An excellent sustained releasing effect is obtained in basic drugs for the respiratory tract such as dihydrocodeine phosphate, dl-methylephedrine hydrochloride and phenylpropanolamine hydrochloride. Acidic drugs that can be used in the present invention include, for example, dehydrocholic acid, diflunisal, ethacrynic acid, fenoprofen, furosemide, gemfibrozil, ibuprofen, naproxen, phenytoin, progencid, sulindac, theophylline, salicylic acid and acetylsalicylic acid. Basic drugs that can be used in the present invention include, for example, acetophenazine, amitriptyline, amphetamine, benztropine, biperiden, bromodiphenhydramine, brompheniramine, carbinoxamine, chloperastine, chlorcyclizine, chorpheniramine, chlorphenoxamine, chlorpromazine, clemastine, clomiphene, clonidine, codeine, cyclizine, cyclobenzaprine, cyproheptadine, desipramine, dexbrompheniramine, dexchlorpheniramine, dextroamphetamine, dextromethorphan, dicyclomine, diphemanil, diphenhydramine, doxepin, doxylamine, ergotamine, fluphenazine, haloperidol, hydrocodone, hydroxychloroquine, hydroxyzine, hyoscyamine, imipramine, levopropoxyphene, maprotiline, meclizine, mepenzolate, meperidine, mephentermine, mesoridazine, metformin, methadone, methylepherdine, methdilazine, methscopolamine, methysergide, metoprolol, nortriptylene, noscapine, nylindrin, oxybutynin, oxycodone, oxymorphone, orphenadrine, papaverine, pentazocine, phendimetrazine, phentermine, phenylephrine, phenylpropanolamine, pyrilamine, tripelennamine, triprolidine, promazine, propoxyphene, propanolol, pseudoephedrine, pyrilamine, quinidine, scopolamine, dextromethorphan, chlorpheniramine and codeine. Amphoteric drugs that can be used in the present invention include for example, aminocaproic acid, aminosalicylic acid, hydromorphone, isoxurprine, levorphanol, melphalan, morphine, nalidixic acid, and paraaminosaliclic acid.

Other drugs that are contemplated include methylphenidate, dexmethylphenidate, oxymorphone, codeine, hydrocodone, chlorpheniramine, niacin, aspirin, salts thereof, and combinations thereof. Salts include, but are not limited to, methylphenidate HCl, dexmethylphenidate HCl, oxymorphone HCl, codeine phosphate, hydrocodone bitartrate, albuterol sulfate, albuterol phosphate, chlorpheniramine maleate, dexchlorpheniramine maleate, metformin HCl, oxybutynin HCl, albuterol sulfate, saligenine hydrochloride, cetrizine hydrochloride, ranitidine HCl, all individually or in combinations.

Representative of other suitable classes of drugs and specific drugs that may not have been mentioned here may be found in U.S. Pat. No. 5,980,882 (columns 7 through 11), the disclosure of which is incorporated herein by reference. Further, pharmaceutically acceptable prodrugs, salts, isomers, polymorphs, and solvates of the drugs identified above, are useful in the present invention. In addition, the free base of the salts specifically listed may be substituted with other pharmaceutically acceptable salts, or use as the free base, or a prodrug form.

Drug-Ion Exchange Resin Complexes

Binding of the selected drug or combination of drugs to the ion exchange resin can be accomplished using methods known in the art. One of ordinary skill in the art with little or no experimentation can easily determine the appropriate method depending upon the drug. Typically four general reactions are used for binding of a basic drug, these are (a) resin ($Na^+$-form) plus drug (salt form); (b) resin ($Na^+$-form) plus drug (as free base); (c) resin ($H^+$-form) plus drug (salt form); and (d) resin ($H^+$-form) plus drug (as free base). All of these reactions except (d) have cationic by-products and these by-products, by competing with the cationic drug for binding sites on the resin, reduce the amount of drug bound at equilibrium. For basic drugs, stoichiometric binding of drug to resin is accomplished only through reaction (d).

Four analogous binding reactions can be carried out for binding an acidic drug to an anion exchange resin. These are (a) resin ($Cl^-$-form) plus drug (salt form); (b) resin ($Cl^-$-form) plus drug (as free acid); (c) resin ($OH^-$-form) plus drug (salt form); (d) resin ($OH^-$-form) plus drug (as free acid). All of these reactions except (d) have ionic by-products and the anions generated when the reactions occur compete with the anionic drug for binding sites on the resin with the result that reduced levels of drug are bound at equilibrium. For acidic drugs, stoichiometric binding of drug to resin is accomplished only through reaction (d). The binding may be performed, for example as a batch or column process, as is known in the art.

Typically the drug-ion exchange resin complex thus formed is collected by filtration and washed with appropriate solvents to remove any unbound drug or by-products. The complexes can be air-dried in trays, in a fluid bed dryer, or other suitable dryer, at room temperature or at elevated temperature.

For preparing the complexes, the batch equilibration is the preferred practice when loading a drug into finely divided ion exchange resin powders. Due to its fine particle size, ion exchange resin does not lend itself to conventional columnar operations used with ion exchange resins. The total ion exchange capacity represents the maximum achievable capacity for exchanging cations or anions measured under ideal laboratory conditions. The capacity which will be realized when loading a drug onto ion exchange resin will be influenced by such factors as the inherent selectivity of the ion exchange resin for the drug, the drug's concentration in the loading solution and the concentration of competing ions also present in the loading solution. The rate of loading will be affected by the activity of the drug and its molecular dimensions as well as the extent to which the polymer phase is swollen during loading.

When utilizing a batch or equilibrium process for loading a drug onto an ion exchange resin, it is usually desirable to load as much as possible of the substance of value onto the ion exchange resin. Complete transfer of the drug from the loading solution is not likely in a single equilibrium stage. Accordingly, more than one equilibration may be required in order to achieve the desired loading onto the ion exchange resin. The use of two or more loading stages, separating the resin from the liquid phase between stages, is a means of achieving maximum loading of the drug onto the ion exchange resin although loss of drug from the liquid phase of the final stage occurs.

Although carefully controlled laboratory experiments are required to establish precise loading and elution conditions, a few general principles can be used. High loading capacity will be favored by high charge density in the drug, A high loading rate is favored by lower molecular weight. Higher drug concentrations in the loading solution, with a minimum of competing ions, will also favor higher adsorption capacity.

The amount of drug that can be loaded onto a resin will typically range from about 1% to about 75% by weight of the drug-ion exchange resin particles. A skilled artisan with limited experimentation can determine the optimum loading for any drug resin complex. In one embodiment, loading of about 10% to about 40% by weight, more desirably, about 15% to about 30% by weight, of the drug-ion exchange resin particles can be employed. Typical loadings of about 25% by weight of the drug-ion exchange resin particles can be advantageously employed.

Thus, in one aspect, the invention provides drug-ion exchange resin complexes comprising a drug loaded in an ion exchange resin as described herein. The drugs and ion exchange resins may be readily selected from amongst those drugs and resins described herein. The invention further provides drug-ion exchange resin matrixes defined as follows.

Release Retardants

The drug release rate from the compositions of the present invention may be further prolonged or modified by treating the drug-ion exchange resin complex prior to the application of the water-permeable diffusion barrier coating described herein, with a release retardant which is a water-insoluble polymer or a combination of a water-insoluble polymers.

Advantageously, the release retardant does not form a separate layer on the drug-ion exchange resin complex, but forms a matrix therewith. Examples of suitable release retardants include, for example, a polyvinyl acetate polymer or a mixture of polymers containing same (e.g., KOLLICOAT SR 30D), cellulose acetates, ethylcellulose polymers (e.g., AQUACOAT™ ECD-30 or SURELEASE™) acrylic based polymers or copolymers (e.g., represented by the EUDRAGIT family of acrylic resins), cellulose phthalate, or any combination of such water-insoluble polymers or polymer systems, all herein defined as "release retardants". These retardants when used, may further prolong or alter the release of the drug from the coated drug-ion exchange resin complex and maximize attaining the desired release profile. Further, use of a release retardant permits in some cases lowering the amount of coating thickness needed to attain a prolonged drug release of up to 24 hours. These retardants can be used in either substantially pure form or as a commercial preparation obtained from a vendor. The preferred release retardant is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; although less desirable, certain pH-dependent members of the EUDRAGIT polymer family, e.g., the L, S, and E, polymers may be selected.

The quantity of polymer that is added as a release retardant typically ranges from about 3% to about 30% or more by weight of the uncoated drug-ion exchange resin particles. More preferably the release retardant, if used, is in the range from about 5% to about 20% and most preferably in the range of about 10% to about 15% by weight of the uncoated drug-ion exchange resin particles, depending on the nature of the drug-ion exchange resin complex and the desired release profile of the medicinal agent(s).

These release retardants can be added during the formation of the drug-ion exchange resin complex either in the beginning, during the middle, or after substantial amount of complex formation has taken place. In the more preferred embodiment, the retardant is added after the formation of drug-ion exchange resin complex. Upon admixing, the drug-ion exchange resin complex particles with the release retardant, the mixture is dried and milled appropriately. In some cases, the milling may be carried out before the complete drying of the complex and then again further drying followed by milling to obtain the desired complex characteristics.

Another embodiment is the use of an impregnating (solvating) agent as a release retardant incorporated into the pharmaceutically acceptable drug ion-exchange resin complex prior to addition of the aqueous based coating. This impregnating (solvating) agent is a hydrophilic (water soluble) agent exemplified by those materials described for example in U.S. Pat. No. 4,221,778 and published US Patent Application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON™ K30) mannitol, methyl cellulose, hydroxypropyl methylcellulose, hydroxypropyl cellulose, and sorbitol.

Coating System

The coating system used in the present invention provides several advantages in preparation of the coated drug-ion exchange resin complex. More particularly, the polymers used in the coating of the invention are water-insoluble and generally non-ionic in nature. The coating polymers avoid problems associated with relatively high tackiness which are encountered with application and curing of prior art coating systems (including, e.g., ionic polymers and those of the EUDRAGIT™ brand polymer system). These problems with tackiness of prior art systems have been found by the present inventors to result in undesirable clumping of the coated particles and to require additional processing to separate particles coated with these polymers. Attempts to solve this problem have been made previously in the art, including, e.g., the addition of anti-tacking agents to prior art coating systems. However, such agents do not satisfactorily solve these problems. Further, the well-known prior art coating systems based upon use of many of the EUDRAGIT™ brand polymer (and ionic polymers) have been found by the present inventors to have additional drawbacks for other reasons, as they cause physical stability problems, including agglomeration and migration of color when a colorant is used for liquid suspension formulations.

The coating system of the present invention can be applied as a substantially tack-free dispersion, without the clumping problems associated with certain prior art coating systems during the coating process and during high temperature curing. Further, the coating system of the invention provides a high tensile strength barrier coating.

In one embodiment, the barrier coating layer is about 5% to about 200%, by weight, of the uncoated drug-ion exchange resin complex. In another embodiment, the barrier coating layer is about 25% to about 50% by weight of the uncoated drug-ion exchange resin complex, about 30% to about 45% by weight of the uncoated complex, or about 35 to about 40% by weight of the uncoated drug-ion exchange resin complex.

Suitably, the present invention provides a barrier coating comprising a water insoluble polymer comprising a polyvinyl acetate polymer, or a blend of polymers comprising a polyvinyl acetate polymer. In one embodiment, the barrier coating further contains a plasticizer, which can facilitate uniform coating of the drug-ion exchange resin complex and enhances the tensile strength of the barrier coating layer. The aqueous based coating dispersions of the present invention that are used to provide a diffusion barrier coating are characterized by having a relatively low tackiness in either the absence or presence of plasticizer(s) and provide a high percent elongation of the polymer film (elasticity) at break in the presence or absence of plasticizer(s). More specifically, the polymer film coating is characterized by exhibiting a tackiness as measured by the Hössel method described by P. Hössel, Cosmetics and Toiletries, 111(8):73 (1996) at 20° C./80% RH and 30° C./75% RH of about 2 or less in the presence or absence of a plasticizer and preferably about 0.5 or less.

Use of a relatively low tack film barrier of the present invention using a polyvinyl acetate (PVA) polymer facilitates more rapid and easier processing of the coating composition and permits use of lower quantities of plasticizer. This provides for enhanced elongation (elasticity) and flexibility of the film coating, a desirable property of the polymer film without significantly increasing film tackiness to undesirable levels due to use of a plasticizer.

A coating system useful in the invention, preferably containing a polyvinyl acetate polymer, is characterized by having film-forming ability at a relatively low temperature, i.e., about 20° C. or less, without a plasticizer. The combination of a plasticizer with a polyvinyl acetate polymer system may further lower the film-forming temperature of the polyvinyl acetate system.

Thus, the selection criteria for the plasticizer incorporated into the aqueous based polymer dispersion composition is to enhance high flexibility or elongation (elasticity) of the film coating at break measured by the texture analyzer TA-XT2 HiR (Stable Microsystems) and by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF], of at least about 100%, of at least about 125% and preferably in a range between about 150% to about 400% while not substantially increasing the tackiness of the polymer film greater than about 2 (wherein the film is measured by the Hossel method referenced above independent of any composition on which it has been deposited). The higher elasticity ranges are usually achieved with coatings of the present invention through the use of a relatively small amount of plasticizer. By using relatively small amount of plasticizer, the plasticizer does not achieve high enough levels to negatively affect the properties of the coating. It has been found that these objectives are achieved by using a relatively lower percent by weight of the selected plasticizer(s) based on the percent by weight of the solids in the aqueous based film forming polymer composition.

Generally, a plasticizer is used in the percent range, or a mixture of plasticizers combine to total, about 2 to about 50% by weight of the coating layer, more preferably about 2.5% to about 20% by weight of the coating layer on the coated drug-ion exchange resin complex. Preferably a plasticizer in range of about 5% to about 10% by weight of the coating layer based on the coated complex provides the most desirable properties.

Suitable plasticizers are water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor P, and mixtures thereof. Other plasticizers are described in Patent Application Publication No. US 2003/0099711 A1, May 29, 2003, page 4 (0041) the disclosure of which is incorporated herein by reference.

The coating composition of the present invention is preferably applied in the form of a polyvinyl acetate (PVA) polymer based aqueous coating dispersion. The PVA is insoluble in water at room temperature. The PVA may be used in either substantially pure form or as a blend. A commercial blend contains primarily a polyvinyl acetate polymer, a stabilizer, and minor amounts of a surfactant such as sodium lauryl sulfate. More specifically, the preferred aqueous based coating solution is KOLLICOAT SR 30 D (BASF Corporation) and whose composition is about 27% PVA polymer, about 2.7% polyvinylpyrrolidone (PVP), about 0.3% sodium lauryl sulfate (solids content 30% w/w). The PVP and surfactant help stabilize the aqueous dispersion of the PVA. Generally, such stabilizing components are present in an amount totaling less than about 10% w/w, and preferably less than about 5% w/w. In one embodiment, if a substantially pure form of PVA is used, it can be dissolved in a suitable non-aqueous solvent to provide a coating solution for the drug ion-exchange resin complex.

In a particularly desirable embodiment, the inventors have found that optimal modified release is obtained when the KOLLICOAT SR-30D aqueous dispersion is cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C.

Where the barrier coating comprises a PVA polymer, the PVA polymer is present in an amount of about 70% to about 90% w/w of the final barrier coating layer, at least about 75%, at least about 80%, about 85% w/w of the final barrier coating layer.

Where the barrier coating also comprises PVP as a stabilizer component (e.g., as is present in KOLLICOAT™ SR 30D), the final barrier coating layer generally contains about 5 to about 10% w/w of polyvinyl pyrrolidone.

The release rate of the present aqueous based polymer coatings of the invention which are designed to provide finished dosage orally ingestible pharmaceutical compositions such as liquid suspension, tablets, etc. are tailored to provide the desired drug release profile over a period of about 8 to 24 hours, and preferably 12 to 24 hours. This programmable release rate may be controlled principally by two variables, i.e., the diffusion barrier coating thickness of the polymeric film coating and optionally, but preferred use of "a release retardant" component as described above added to the drug-ion exchange resin complex to form a fine particulate matrix prior to the polymer film coating step. The release retardant is preferably a water insoluble polymer as previously described such as a PVA dispersion which has the same or similar composition of solids as the preferred aqueous based film forming coating polymer dispersion described herein used in the coating step or an acrylic based polymer available commercially under the EUDRAGIT™ brand name, manufactured by Rohm Pharma Polymers. The properties of different EUDRAGIT™ compositions commercially available are described in literature from Rohm Pharma and are also described in U.S. Pat. No. 6,419,960 (column 10-11), the disclosure of which is incorporated herein by reference. Other water insoluble polymers include those listed in column 10, lines 41-53 of U.S. Pat. No. 6,419,960 the disclosure of which is incorporated herein by reference.

Finished Dose Formulations

The drug-ion exchange resin complexes of the present invention, can readily be formulated with pharmaceutically acceptable excipients according to methods well known to those of skill in the art. In one embodiment, these formulations contain a substantially coated drug-ion exchange resin complex of the invention, optionally with a release retardant. In another embodiment, such formulations may also contain a selected amount of uncoated drug-ion exchange resin complex, optionally with a release retardant as described herein. In certain formulations, mixtures of coated drug-ion exchange resin complexes and uncoated drug-ion exchange resin complexes are present. These formulations may contain any suitable ratio of coated to uncoated product.

For example, a formulation of the invention containing the active component dextromethorphan desirably contains a mixture of a coated drug-ion exchange resin complex of the invention and an uncoated drug-ion exchange resin complex of the invention, in order to achieve the optimal release profile. The uncoated dextromethorphan-ion exchange resin complex and the coated dextromethorphan-ion exchange resin complex may be present in a ratio of 100:1 to 1:100 by weight. In certain embodiments, the ratio may be in about 30:70, about 10:1 to about 1:10, or about 2:1 to about 1:2, by weight.

In yet another embodiment, the formulations of the invention may contain more than one active component. For example, the formulation may contain more than one drug loaded into an ion exchange resin to form a complex of the invention. As another example, the formulation may contain a first drug-ion exchange resin complex of the invention in combination with another active component (drug) which may be in a second drug-ion exchange resin complex of the invention. In still another example, the formulation may contain a drug-ion exchange resin complex of the invention in combination with one or more active components which are not in a drug-ion exchange resin complex.

The coated drug-ion exchange resin complex of the invention may be formulated for delivery by any suitable route including, e.g., orally, topically, intraperitoneally, transdermally, sublingually, intramuscularly, rectally, transbuccally, intranasally, liposomally, via inhalation, vaginally, intraoccularly, via local delivery (for example, by catheter or stent), subcutaneously, intraadiposally, intraarticularly, or intrathecally. Preferably, the complex is formulated for oral delivery.

The drug-ion exchange resin composition thus prepared may be stored for future use or promptly formulated with conventional pharmaceutically acceptable carriers to prepare finished ingestible compositions for delivery orally, nasogastric tube, or via other means. The compositions according to this invention may, for example, take the form of liquid preparations such as suspensions, or solid preparations such as capsules, tablets, caplets, sublinguals, powders, wafers, strips, gels, including liquigels, etc. In one embodiment, a tablet of the invention is formulated as an orally disintegrating tablet. Such orally dissolving tablets may disintegrate in the mouth in less than about 60 seconds.

The drug-ion exchange resin coated compositions may be formulated using conventional pharmaceutically acceptable carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

Suitable thickeners include, e.g., tragacanth; xanthan gum; bentonite; starch; acacia and lower alkyl ethers of cellulose (including the hydroxy and carboxy derivatives of the cellulose ethers). Examples of cellulose include, e.g., hydroxypropyl cellulose, hydroxypropyl methyl cellulose, sodium carboxy methylcellulose, microcrystalline cellulose (MCC), and MCC with sodium carboxyl methyl cellulose. In one embodiment, tragacanth is used and incorporated in an amount of from about 0.1 to about 1.0% weight per volume (w/v) of the composition, and more preferably about 0.5% w/v of the composition. Xanthan gum is used in the amount of from about 0.025 to about 0.5% w/v and preferably about 0.25% w/v.

The sustained-release ion exchange resin compositions may include a humectant composition to give the liquid greater viscosity and stability. Suitable humectants useful in the finished formulations include glycerin, polyethylene glycol, propylene glycol and mixtures thereof.

The oral liquid compositions of the present invention may also comprise one or more surfactants in amounts of up to about 5.0% w/v and preferably from about 0.02 to about 3.0% w/v of the total formulation. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20) sorbitan monooleate and sorbitan monooleate. These are commercially known as TWEENS and SPANS and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added functions to keep any flavors and sweeteners homogeneously dissolved and dispersed in solution.

Suitable polysorbates include polysorbate 20, polysorbate 40, polysorbate 80 and mixtures thereof. Most preferably, polysorbate 80 is employed. The surfactant component will comprise from about 0.01 to about 2.0% w/v of the total composition and preferably will comprise about 0.1% w/v of the total weight of the composition.

A second emulsifer/surfactant useful in combination with polysorbates may be employed and is preferably a poloxamer such as Poloxamer 407. Poloxamer 407 has an HLB (hydrophilic/lipophilic balance) of about 22 and is sold under the tradename Pluoronic-127 (BASF-NJ). The two surfactants can be employed in substantially equivalent amounts. For example, the Poloxamer 407 and polysorbate 80 may each be employed together at levels of approximately from about 0.02 to about 4.0% w/v of the total weight of the formulation.

Aqueous suspensions may be obtained by dispersing the drug-ion exchange resin compositions in a suitable aqueous vehicle, optionally with the addition of suitable viscosity enhancing agent(s) (e.g., cellulose derivatives, xanthan gum, etc). Non-aqueous suspensions may be obtained by dispersing the foregoing compositions in a suitable non-aqueous based vehicle, optionally with the addition of suitable viscosity enhancing agent(s) (e.g., hydrogenated edible fats, aluminum state, etc.). Suitable non-aqueous vehicles include, for example, almond oil, arachis oil, soybean oil or soybean oil or fractionated vegetable oils such as fractionated coconut oil.

Useful preservatives include, but are not limited to, sodium benzoate, benzoic acid, potassium sorbate, salts of edetate (also known as salts of ethylenediaminetetraacetic acid, or EDTA, such as disodium EDTA), parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetracetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis[ethyliminodi(acetic acid)] (EGTA); 1,10-bis(2-pyridylmethyl)-1,4,7,10-tetraazadecane (BPTETA); ethylenediamine (EDAMINE); Trans-1,2-diaminocyclohexane-N, N, N',N'-tetraacetic acid (CDTA); ethylenediamine-N, N'-diacetate (EDDA); phenazine methosulphate (PMS); 2, 6-Dichloro-indophenol (DCPIP); Bis(carboxymethyl)diaza-18-crown-6 (CROWN); porphine; chlorophyll; dimercaprol (2, 3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative. Methods for evaluating the efficacy of preservatives in pharmaceutical formulations are known to those skilled in the art. Preferred preservatives are the paraben preservatives include methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 16:1, preferably 9:1.

In the instance where auxiliary sweeteners are utilized, the present invention contemplates the inclusion of those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, high fructose corn syrup, dextrose, sucrose, sugar, maltose, partially hydrolyzed starch, or corn syrup solids and sugar alcohols such as sorbitol, xylitol, mannitol and mixtures thereof;

In general, the amount of sweetener will vary with the desired amount of sweeteners selected for a particular liquid formulation. This amount will normally be 0.001 to about 90% by weight, per volume of the final liquid composition, when using an easily extractable sweetener. The water-soluble sweeteners described above, are preferably used in amounts of about 5 to about 70% by weight per volume, and most preferably from about 10 to about 50% by weight per volume of the final liquid composition. In contrast, the artificial sweeteners [e.g., sucralose, acesulfame K, and dipeptide based sweeteners] are used in amounts of about 0.005 to about 5.0% and most preferably about 0.01 to about 2.5% by weight per volume of the final liquid composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e. thymol, eculyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

The colorants useful in the present invention include the pigments such as titanium dioxide that may be incorporated in amounts of up to about 1% by weight per volume, and preferably up to about 0.6% by weight per volume. Also, the colorants may include dyes suitable for food, drug and cosmetic applications, and known as D&C and F.D. & C. dyes and the like. The materials acceptable for the foregoing spectrum of use are preferably water-soluble. Illustrative examples include indigoid dye, known as F.D. & C. Blue No. 2, which is the disodium salt of 5,5'indigotindisulfonic acid. Similarly, the dye known as F.D. & C. Green No. 1 comprises a triphenylmethane dye and is the monosodium salt of 4-[4-N-ethyl p-sulfobenzylamino)diphenylmethylene]-[1-(N-ethyl-N-p-sulfoniumbenzyl)-2,5-cyclohexadien-imine]. A full recitation of all F.D. & C. and D. & C. and their corresponding chemical structures may be found in the Kirk-Othmer Encyclopedia of Chemical Technology, in Volume 5, at Pages 857-884, which text is accordingly incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a suspension, to flocculate. Those skilled in the art are well versed in suitable empirical methods to determine the appropriate wetting agents and concentrations to achieve optimum dispersion and avoid flocculation. Suitable wetting agents are listed in the US Pharmacoepia 29.

In another aspect, the invention provides a product containing a coated drug-ion exchange resin complex of the invention.

In some embodiments, the coated drug-ion exchange resin complexes of the invention are in packs in a form ready for administration, e.g., a blister pack, a bottle, syringes, foil packs, pouches, or other suitable container. In other embodiments, the compositions of the invention are in concentrated form in packs, optionally with the diluent required to make a final solution for administration. In still other embodiments, the product contains a compound useful in the invention in solid form and, optionally, a separate container with a suitable suspension base or other carrier for the drug-ion exchange resin complex useful in the invention.

In still other embodiments, the above packs/kits include other components, e.g., a meter dose apparatus/device, instructions for dilution, mixing and/or administration of the product, other containers, nasogastric tubes, etc. Other such pack/kit components will be readily apparent to one of ordinary skill in the art.

Devices have been described, and many are commercially available, which provide for metered drug administration, including controlled infusion devices (e.g., for patient-controlled analgesia), metered-dose inhalers and implantable pumps. For example, various liquid metering devices for squeezable bottles have been described [U.S. Pat. No. 6,997, 358, U.S. Pat. No. 3,146,919, filed in 1960, U.S. Pat. No. 3,567,079, filed in 1968, and in GB 2201395, filed in 1986.] A device for dispensing multiple compositions is provided in U.S. Pat. No. 6,997,219.

Methods and apparatus for delivery of drugs through nasogastric tubes are well known to those of ordinary skill in the art. See, e.g., E. Bryson, "Drug Administration via Nasogastric Tube", *Nurs Times,* 2001, Apr. 19-25 97(16):51. The present invention can be readily delivered using such devices. Suitable nasogastric tubes are available commercially and/or have been described. See, e.g., U.S. Pat. No. 5,334,166; U.S. Pat. No. 5,322,073; U.S. Pat. No. 4,619,673; U.S. Pat. No. 4,363,323.

The following examples are provided to more specifically illustrate the modified release compositions of the present invention and not intended to be limiting. They are for illustrative purposes only and it is realized that changes and variations can be made without departing from the spirit and scope of the invention.

Examples 1 to 17 are illustrative of the preparation of typical coated drug-ion exchange resins complexes of the present invention. Some samples from the compositions described in these examples were further processed into finish dosage forms and others were stored for future formulation and on-going stability testing under accelerated and room temperature conditions.

Example 18 illustrates the compositions of an orally disintegrating tablet using the compositions of the current invention.

Example 19 and 20 provide the compositions containing EUDRAGIT and AQUACOAT as coating compositions that resulted in color migration and caused flocculation/agglomeration.

Example 21 and 22 illustrate formulations of the invention that reduce the abuse potential of the drugs using the coated drug-ion exchange resins of the present invention.

Preparation of Coated Drug Resin Complex

Example 1

Preparation of Coated Morphine Resin Complex

| Ingredient | Quantity |
| --- | --- |
| Morphine Resin Complex | |
| Morphine Sulfate | 450 g |
| Purified Water | 5 L |
| AMBERLITE IRP-69 RESIN | 807 g |
| KOLLICOAT SR-30D polymer system | 501 g |
| Coated Morphine Resin Complex | |
| KOLLICOAT SR-30D polymer system | 952 g |
| Triacetin | 14 g |
| Purified Water | 533 g |
| Morphine Resin Complex | 600 g |

The morphine resin complex was prepared by first dissolving 450 g of morphine sulfate in 5 L of purified water, and then slowly adding 807 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 25%. KOLLICOAT™ SR-30D of 501 g was then slowly added to the wet resin complex in a Hobart type mixer (Kitchen Aid) to form a uniform mass. The wet mass was again dried at 50° C. in a VWR™ convection oven to the moisture content around 20%. The semi-dried granules were then milled through a 40 mesh screen using a CO-MIL™ brand mill and continued drying under 50° C. until the moisture content was between 4-6%. The dried granules were then milled through a 40 mesh screen using CO-MIL™ brand mill [QUADRO].

The coating solution was prepared by dispersing 952 g of KOLLICOAT™ SR-30D, 14 g of triacetin in 533 g of purified water and mixing for 1 hour. The coating process was performed in a VECTOR™ FLM-1 fluid bed processor by applying 1,350 g of the coating solution to 600 g of Morphine Resin Complex using WURSTER process that resulted in 45% weight gain. The coating conditions were controlled at an inlet temperature of 77-82° C., product temperature of 26-33° C., air flow of 17-18 cfm, nozzle pressure of 2.5 kg/cm$^2$, accelerator air pressure of 1.0 kg/cm$^2$ and spray rate of 5-8 g/min so that uniform coating was achieved. The Coated Morphine Resin Complex was then placed at 60° C. for 5 hours for curing.

Example 2

Preparation of Coated Oxycodone Resin Complex

| Ingredient | Quantity |
| --- | --- |
| Oxycodone Resin Complex | |
| Oxycodone HCl | 450 g |
| Purified Water | 8 L |
| AMBERLITE IRP-69 resin | 1,427 g |
| KOLLICOAT SR-30D polymer system | 500 g |
| Coated Oxycodone Resin Complex | |
| KOLLICOAT SR-30D polymer system | 825 g |
| Triacetin | 12 g |
| Purified Water | 462 g |
| Oxycodone Resin Complex | 600 g |

The Oxycodone Resin Complex was prepared by first dissolving 450 g of oxycodone HCl in 8 L of purified water, and then slowly adding 1,427 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 15%. KOLLICOAT™ SR-30D of 500 g was then slowly added to the wet resin complex in a Hobart type mixer (Kitchen Aid) to form a uniform mass. The wet mass was again dried at 50° C. VWR™ convection oven to the moisture content around 12%. The semi-dried granules were then milled through 40 mesh screen using CO-MIL™ brand mill and continued drying under 50° C. until the moisture content was between 4-6%. The dried granules were then milled through 40 mesh screen using CO-MIL™ brand mill.

The coating solution was prepared by dispersing 825 g of KOLLICOAT™ SR-30D, 12 g of triacetin in 462 g of purified water and mixed for 1 hour. The coating process was performed in a VECTOR™ FLM-1 fluid bed processor by applying 1,200 g of the coating solution to 600 g of Oxycodone Resin Complex using WURSTER process that resulted in 40% weight gain. The coating conditions were controlled at an inlet temperature of 70-80° C., product temperature of 25-31° C., air flow of 16-17 cfm, nozzle pressure of 2.5-3.0 kg/cm$^2$, accelerator air pressure of 1.0 kg/cm$^2$ and spray rate of 3-5 g/min so that uniform coating was achieved. The Coated Oxycodone Resin Complex was then placed at 60° C. for 5 hours for curing.

Example 3

Preparation of Coated Albuterol Resin Complex

| Ingredient | Quantity |
| --- | --- |
| Albuterol Resin Complex | |
| Albuterol Sulfate | 286 g |
| Purified Water | 8 L |
| AMBERLITE IRP-69 resin | 1837 g |
| KOLLICOAT SR-30D polymer system | 640 g |
| Coated Albuterol Resin Complex | |
| KOLLICOAT SR-30D polymer system | 952 g |
| Triacetin | 14 g |
| Purified Water | 533 g |
| Albuterol Resin Complex | 600 g |

The Albuterol Resin Complex was prepared by first dissolving 286 g of albuterol sulfate in 8 L of purified water, and then slowly adding 1837 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 30%. KOLLICOAT™ SR-30D of 640 g was then slowly added to the wet resin complex in a Hobart type mixer (Kitchen Aid) to form a uniform mass. The wet mass was again dried at 50° C. in a VWR™ convection oven to the moisture content around 25%. The semi-dried granules were then milled through a 40 mesh screen using CO-MIL™ brand mill and continued drying under 50° C. until the moisture content was between 4-6%. The dried granules were then milled through a 40 mesh screen using CO-MIL™ brand mill.

The coating solution was prepared by dispersing 952 g of KOLLICOAT™ SR-30D, 14 g of triacetin in 533 g of purified water and mixing for 1 hour. The coating process was performed in a VECTOR™ FLM-1 fluid bed processor by applying 1,350 g of the coating solution to 600 g of Albuterol Resin Complex using WURSTER process that resulted in 45% weight gain. The coating conditions were controlled at an inlet temperature of about 60° C., product temperature of 31-34° C., air flow of 18-19 cfm, nozzle pressure of 2.5 kg/cm$^2$, accelerator air pressure of 1.0 kg/cm$^2$ and spray rate of 3-6 g/min so that uniform coating was achieved. The Coated Albuterol Resin Complex was then placed at 60° C. for 5 hours for curing.

Example 4

Preparation of Coated Methylphenidate Resin Complex

| Ingredient | Quantity |
| --- | --- |
| Methylphenidate Resin Complex | |
| Methylphenidate HCl | 500 g |
| Purified Water | 8 L |
| AMBERLITE IRP-69 resin | 1,306 g |
| EUDRAGIT NE-30D polymer system | 467 g |
| Coated Methylphenidate Resin Complex | |
| KOLLICOAT SR-30D polymer system | 635 g |
| Triacetin | 9.5 g |
| Purified Water | 356 g |
| Methylphenidate Resin Complex | 600 g |

The Methylphenidate Resin Complex was prepared by first dissolving 500 g of methylphenidate HCl in 8 L of purified water, and then slowly adding 1,306 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 20-30%. EUDRAGIT™NE-30D of 467 g was then slowly added to the wet resin complex in a Hobart type mixer (Kitchen Aid) to form a uniform mass. The wet mass was then passed through a 10 mesh screen and again dried at 50° C. in a VWR™ convection oven to the moisture content around 4-6%. The dried granules were then milled through a 40 mesh screen using CO-MIL™ brand mill.

The coating solution was prepared by dispersing 635 g of KOLLICOAT™ SR-30D, 9.5 g of triacetin in 356 g of purified water and mixing for 1 hour. The coating process was performed in a VECTOR™ FLM-1 fluid bed processor by applying 900 g of the coating solution to 600 g of Methylphenidate Resin Complex using Wurster process that resulted in 30% weight gain. The coating conditions were controlled at an inlet temperature of 55-62° C., product temperature of 29-31° C., air flow of 20-24 cfm, nozzle pressure of 2.5 kg/cm$^2$, accelerator air pressure of 1.0 kg/cm$^2$ and spray rate of 4-6 g/min so that uniform coating was achieved. The Coated Methylphenidate Resin Complex was then placed at 60° C. for 5 hours for curing.

Example 5

Preparation of Coated Dextromethorphan Resin Complex

| Ingredient | Quantity |
| --- | --- |
| Dextromethorphan Resin Complex | |
| Dextromethorphan HBr | 954 g |
| Purified Water | 8 L |
| AMBERLITE IRP-69 resin | 1,758 g |
| KOLLIDON K-30 polymer | 116 g |
| Purified Water | 1,150 g |
| Coated Dextromethorphan Resin Complex | |
| KOLLICOAT SR-30D polymer system | 762 g |
| Triacetin | 11 g |
| Purified Water | 427 g |
| Dextromethorphan Resin Complex | 600 g |

The Dextromethorphan Resin Complex was prepared by first dissolving 954 g of dextromethorphan HBr in 8 L of purified water heated to 75-80° C., and then slowly adding 1,758 g of AMBERLITE™ IRP-69 resin with continuous mixing while cooling down to room temperature. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 20-25%. In a separate container, KOLLIDON K-30 polymer (116 g) was dissolved in 1,150 g of purified water and slowly applied to the wet resin complex in a Hobart type mixer (Kitchen Aid) to form a uniform mass. The wet mass was then dried at 50° C. in a VWR™ convection oven to the moisture content was around 4-6%. The dried granules were then milled through a 40 mesh screen using CO-MIL™ brand mill.

The coating solution was prepared by dispersing 762 g of KOLLICOAT™ SR-30D polymer, 11 g of triacetin in 427 g of purified water and mixing for 1 hour. The coating process was performed in a VECTOR™ FLM-1 fluid bed processor by applying 1,050 g of the coating solution to 600 g of Dextromethorphan Resin Complex using Wurster process that resulted in 35% weight gain. The coating conditions were controlled at inlet temperature of 64-71° C., product temperature of 27-35° C., air flow of 15-20 cfm, nozzle pressure of 2.5 kg/cm$^2$, accelerator air pressure of 1.0 kg/cm$^2$ and spray rate of 4-6 g/min so that uniform coating was achieved. The Coated Dextromethorphan Resin Complex was then placed at 60° C. for 5 hours for curing.

Example 6

Preparation of Coated Codeine Resin Complex

| Ingredient | Quantity |
| --- | --- |
| Codeine Resin Complex | |
| Codeine Phosphate | 500 g |
| Purified Water | 5 kg |
| AMBERLITE IRP-69 resin | 1,856 g |
| EUDRAGIT NE-30D polymer system | 668 g |
| Purified Water | 1,150 g |
| Coated Codeine Resin Complex | |
| KOLLICOAT SR-30D polymer | 635 g |
| Triacetin | 9.5 g |
| Purified Water | 356 g |
| Codeine Resin Complex | 600 g |

The Codeine Resin Complex was prepared by first dissolving 500 g of codeine phosphate in 5 kg of purified water, and then slowly adding 1,856 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried at VWR™ convection oven maintained at 50° C. until moisture content was about 20-30%. EUDRAGITTMNE-30D polymer system (668 g) was mixed with 1,150 g of purified water and then slowly added to the wet resin complex in a Hobart type mixer (Kitchen Aid) to form a uniform mass. The wet mass was dried at 50° C. in a VWR™ convection oven to the moisture content around 3-7%. The dried granules were then milled through 40 mesh screen using CO-MIL™ brand mill.

The coating solution was prepared by dispersing 635 g of KOLLICOAT™ SR-30D polymer, 9.5 g of triacetin in 356 g of purified water and mixing for 1 hour. The coating process was performed in a VECTOR™ FLM-1 fluid bed processor by applying 900 g of the coating solution to 600 g of Codeine Resin Complex using Wurster process that resulted in 30% weight gain. The coating conditions were controlled at an inlet temperature of 54-68° C., product temperature of 30-35° C., air flow of 19-23 cfm, nozzle pressure of 2.5 kg/cm$^2$, accelerator air pressure of 1.0 kg/cm$^2$ and spray rate of 4-6 g/min so that uniform coating was achieved. The Coated Codeine Resin Complex was then placed at 60° C. for 5 hours for curing.

Example 7

Preparation of Coated Tramadol Resin Complex

| Ingredient | Quantity |
| --- | --- |
| Tramadol Resin Complex | |
| Tramadol HCl | 500 g |
| Purified Water | 8 L |
| AMBERLITE IRP-69 resin | 1,345 g |
| KOLLICOAT SR-30D polymer | 467 g |
| Coated Tramadol Resin Complex | |
| KOLLICOAT SR-30D polymer | 762 g |
| Triacetin | 11 g |
| Purified Water | 427 g |
| Tramadol Resin Complex | 600 g |

The Tramadol Resin Complex was prepared by first dissolving 500 g of tramadol HCl in 8 L of purified water, and then slowly adding 1,345 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 25%. KOLLICOAT™ SR-30D polymer (467 g) was then slowly added to the wet resin complex in a Hobart type mixer (Kitchen Aid) to form a uniform mass. The wet mass was again dried in a 50° C. VWR™ convection oven to the moisture content around 20%. The semi-dried granules were then milled through a 40 mesh screen using CO-MIL™ brand mill and continued drying under 50° C. until the moisture content was between 4-6%. The dried granules were then milled through a 40 mesh screen using CO-MIL™ brand mill.

The coating solution was prepared by dispersing 762 g of KOLLICOAT™ SR-30D polymer, 11 g of triacetin in 427 g of purified water and mixing for 1 hour. The coating process was performed in a VECTOR™ FLM-1 fluid bed processor by applying 1,050 g of the coating solution to 600 g of Tramadol Resin Complex using Wurster process that resulted in 35% weight gain. The coating conditions were controlled at an inlet temperature of about 60-66° C., product temperature of 25-33° C., air flow of 16-19 cfm, nozzle pressure of 2.5 kg/cm$^2$, accelerator air pressure of 1.0 kg/cm$^2$ and spray rate of 4-5 g/min so that uniform coating was achieved. The Coated Tramadol Resin Complex was then placed at 60° C. for 5 hours for curing.

Example 8

Preparation of Coated Pseudoephedrine Resin Complex

| Ingredient | Quantity |
| --- | --- |
| Pseudoephedrine Resin Complex | |
| Pseudoephedrine HCl | 857 g |
| Purified Water | 5 L |
| AMBERLITE IRP-69 resin | 1,589 g |
| KOLLICOAT SR-30D polymer system | 668 g |
| Coated Pseudoephedrine Resin Complex | |
| KOLLICOAT SR-30D polymer system | 825 g |
| Triacetin | 12 g |
| Purified Water | 462 g |
| Pseudoephedrine Resin Complex | 600 g |

The Pseudoephedrine Resin Complex was prepared by first dissolving 857 g of pseudoephedrine HCl in 5 L of purified water, and then slowly adding 1,589 g of AMBERLITE™ IRP-69 resin with continuous mixing. The dispersion was mixed for 4 hours and upon completion, allowed to settle before decanting the supernatant. The slurry was filtered and rinsed 3 times with sufficient amounts of purified water. The wet resin complex was then dried in a VWR™ convection oven maintained at 50° C. until moisture content was about 25%. KOLLICOAT™ SR-30D polymer (668 g) was then slowly added to the wet resin complex in a Hobart type mixer (Kitchen Aid) to form a uniform mass. The wet mass was again dried at 50° C. in a VWR™ convection oven to the moisture content around 30%. The semi-dried granules were then milled through a 40 mesh screen using CO-MIL™ brand mill and continued drying under 50° C. until the moisture content was between 4-6%. The dried granules were then milled through a 40 mesh screen using CO-MIL™ brand mill.

The coating solution was prepared by dispersing 825 g of KOLLICOAT™ SR-30D polymer, 12 g of triacetin in 462 g of purified water and mixing for 1 hour. The coating process was performed in a VECTOR™ FLM-1 fluid bed processor by applying 1,200 g of the coating solution to 600 g of Pseudoephedrine Resin Complex using Wuster process that resulted in 40% weight gain. The coating conditions were controlled at an inlet temperature of about 68-72° C., product temperature of 26-32° C., air flow of 16-19 cfm, nozzle pressure of 2.5 kg/cm², accelerator air pressure of 1.0 kg/cm² and spray rate of 4-6 g/min so that uniform coating was achieved. The Coated Pseudoephedrine Resin Complex was then placed at 60° C. for 5 hours for curing.

Example 9

Preparation of Coated Phenylephrine Resin Complex

| Ingredient | Quantity |
| --- | --- |
| Phenylephrine Resin Complex | |
| Phenylephrine HCl | 400 g |
| Purified Water | 8 L |
| AMBERLITE IRP-69 resin | 1,165 g |
| KOLLICOAT SR-30D polymer system | 467 g |
| Coated Phenylephrine Resin Complex | |
| KOLLICOAT SR-30D polymer system | 825 g |
| Triacetin | 12 g |
| Purified Water | 462 g |
| Phenylephrine Resin Complex | 600 g |

The Phenylephrine Resin Complex was prepared by first dissolving 400 g of phenylephrine HCl in 8 L of purified water, and then slowly adding 1,165 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 25%. KOLLICOAT™ SR-30D polymer system (467 g) was then slowly added to the wet resin complex in a Hobart type mixer (Kitchen Aid) to form a uniform mass. The wet mass was again dried at 50° C. in a VWR™ convection oven to the moisture content around 30%. The semi-dried granules were then milled through a 40 mesh screen using CO-MIL™ brand mill and continued drying under 50° C. until the moisture content was between 4-6%. The dried granules were then milled through a 40 mesh screen using CO-MIL™ brand mill.

The coating solution was prepared by dispersing 825 g of KOLLICOAT™ SR-30D polymer system, 12 g of triacetin in 462 g of purified water and mixing for 1 hour. The coating process was performed in a VECTOR™ FLM-1 fluid bed processor by applying 1,200 g of the coating solution to 600 g of Phenylephrine Resin Complex using Wurster process that resulted in 40% weight gain. The coating conditions were controlled at an inlet temperature of about 60-72° C., product temperature of 25-34° C., air flow of 16-19 cfm, nozzle pressure of 2.5 kg/cm², accelerator air pressure of 1.0 kg/cm² and spray rate of 4-6 g/min so that uniform coating was achieved. The Coated Phenylephrine Resin Complex was then placed at 60° C. for 5 hours for curing.

Example 10

Preparation of Coated Hydrocodone Resin Complex

| Ingredient | Quantity |
| --- | --- |
| Hydrocodone Resin Complex | |
| Hydrocodone Bitartrate | 450 g |
| Purified Water | 8 kg |
| AMBERLITE IRP-69 resin | 1,407 g |
| KOLLICOAT SR-30D polymer system | 500 g |
| Coated Hydrocodone Resin Complex | |
| KOLLICOAT SR-30D polymer system | 952 g |
| Triacetin | 14 g |
| Purified Water | 533 g |
| Hydrocodone Resin Complex | 600 g |

The Hydrocodone Resin Complex was prepared by first dissolving 450 g of hydrocodone Bitartrate in 8 kg of purified water, and then slowly adding 1,407 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 20-25%. KOLLICOAT™ SR-30D polymer (500 g) was then slowly added to the wet resin complex in a Hobart type mixer (Kitchen Aid) to form a uniform mass. The wet mass was again dried in a 50° C. VWR™ convection oven to the moisture content around 15-20%. The semi-dried granules were then milled through a 40 mesh screen using CO-MIL™ brand mill and continued drying under 50° C. until the moisture content was between 3-7%. The dried granules were then milled through a 40 mesh screen using CO-MIL™ brand mill.

The coating solution was prepared by dispersing 952 g of KOLLICOAT™ SR-30D polymer, 14 g of triacetin in 533 g of purified water and mixed for 1 hour. The coating process was performed in a VECTOR™ FLM-1 fluid bed processor by applying 1,050 g of the coating solution to 600 g of Hydrocodone Resin Complex using Wurster process that resulted in 35% weight gain. The coating conditions were controlled at an inlet temperature of about 55-66° C., product temperature of 26-32° C., air flow of 16-20 cfm, nozzle pressure of 2.5 kg/cm$^2$, accelerator air pressure of 1.0 kg/cm$^2$ and spray rate of 4-5 g/min so that uniform coating was achieved. The Coated Hydrocodone Resin Complex was then placed at 60° C. for 5 hours for curing.

Example 11

Preparation of Coated Venlafaxine Resin Complex

| Ingredient | Quantity |
| --- | --- |
| Venlafaxine Resin Complex | |
| Venlafaxine HCl | 500 g |
| Purified Water | 5 L |
| AMBERLITE IRP-69 resin | 1,000 g |
| EUDRAGIT NE-30D polymer system | 467 g |
| Coated Venlafaxine Resin Complex | |
| KOLLICOAT SR-30D polymer system | 635 g |
| Triacetin | 9.5 g |
| Purified Water | 356 g |
| Venlafaxine Resin Complex | 600 g |

The Venlafaxine Resin Complex was prepared by first dissolving 500 g of venlafaxine HCl in 5 L of purified water, and then slowly adding 1,000 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 25%. EUDRAGIT™ NE-30D polymer of 467 g was then slowly added to the wet resin complex in a Hobart type mixer (Kitchen Aid) to form a uniform mass. The wet mass was dried in a 50° C. VWR™ convection oven to the moisture content around 4-6%. The dried granules were then milled through a 40 mesh screen using CO-MIL™ brand mill.

The coating solution was prepared by dispersing 635 g of KOLLICOAT™ SR-30D polymer system, 9.5 g of triacetin in 356 g of purified water and mixing for 1 hour. The coating process was performed in a VECTOR™ FLM-1 fluid bed processor by applying 900 g of the coating solution to 600 g of Venlafaxine Resin Complex using Wurster process that resulted in 30% weight gain. The coating conditions were controlled at an inlet temperature of 40-45° C., product temperature of 29-33° C., air flow of 40 cfm and nozzle pressure of 2.5 kg/cm$^2$, accelerator air pressure of 1.0 kg/cm$^2$ and spray rate of 4-7 g/min so that uniform coating was achieved. The Coated Venlafaxine Resin Complex was then placed at 60° C. for 5 hours for curing.

Example 12

Preparation of Coated Oxybutynin Resin Complex

| Ingredient | Quantity |
| --- | --- |
| Oxybutynin Resin Complex | |
| Oxybutynin Hydrochloride | 300 g |
| Purified Water | 8 L |
| AMBERLITE IRP-69 Resin (anhydrous) | 1586 g |
| KOLLICOAT SR-30D polymer system | 540 g |
| Coated Oxybutynin Resin Complex | |
| KOLLICOAT SR-30D polymer system | 761.9 g |
| Triacetin | 11.4 g |
| Purified Water | 426.7 g |
| Oxybutynin Resin Complex | 600 g |

The Oxybutynin Resin Complex was prepared by first dissolving 300 g of oxybutynin hydrochloride in 8 L of purified water, and then slowly adding 1586 g of AMBERLITE™ IRP-69 resin with continuous mixing. The pH was adjusted to 3.9. The dispersion was mixed for 4 hours, and upon completion, allowed to settle before decanting the supernatant. The slurring/decanting process was repeated twice with sufficient amounts of purified water. The wet resin complex was then dried in a VWR™ convention oven maintained at 50° C. until moisture content was about 25%. KOLLICOAT™ SR-30D polymer system (540 g) was then slowly added to the wet resin complex in a Hobart type mixer (Kitchen Aid) to form a uniform mass. The wet mass was again dried in a 50° C. VWR™ convention oven to the moisture content about 25%. The semi-dried granules were then milled through a 40 mesh screen using CO-MIL™ and continued drying at 50° C. until the moisture content was between 3-7%. The dried granules were then milled through a 40 mesh screen using CO-MIL™.

The coating solution was prepared by dispersing 761.9 g of KOLLICOAT™ SR-30D polymer, 11.4 g triacetin in 426.7 g of purified water and mixing for 1 hour. The coating process was performed in a VECTOR™ FLM-1 fluid bed processor by applying 1050 g of the coating solution to 600 g of Oxybutynin Resin Complex using Wurster process, resulting in a 35% weight gain. The coating conditions were controlled at an inlet temperature of about 58-72° C., product temperature of 26-32° C., air flow of 16-20 cfm, nozzle pressure of 2.5 kg/cm$^2$, accelerator air pressure of 1.0 kg/cm$^2$ and a spray rate of 4-6 g/min, so that a uniform coating was achieved. The Coated Oxybutynin Resin Complex was then placed at 60° C. for 5 hours for curing.

Example 13

Preparation of Coated Metformin Resin Complex

| Ingredient | Quantity |
| --- | --- |
| Metformin Resin Complex | |
| Metformin HCl | 225 g |
| Purified Water | 4 L |
| AMBERLITE IRP-69 Resin (anhydrous) | 735 g |
| KOLLICOAT SR-30D polymer system | 250 g |
| Purified Water | 150 g |
| Coated Metformin Resin Complex | |
| KOLLICOAT SR-30D polymer system | 761.9 g |
| Triacetin | 11.4 g |
| Purified Water | 426.7 g |
| Metformin Resin Complex | 600 g |

The Metformin Resin Complex was prepared by first dissolving 225 g of metformin HCl in 4 L of purified water, and then slowly adding 735 g of AMBERLITE™ IRP-69 resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until moisture content was about 25%. KOLLICOAT™ SR-30D (250 g) was first mixed with 150 g of purified water and the mixture was then slowly added to the wet resin complex in a Hobart type mixer (Kitchen Aid) to form a uniform mass. The wet mass was again dried in a 50° C. VWR™ convection oven to the moisture content about 20%. The semi-dried granules were then milled through a 40 mesh screen using CO-MIL™ brand mill and drying continued at 50° C. until the moisture content was between 3-7%. The dried granules were then milled through a 40 mesh screen using CO-MIL™ brand mill.

The coating solution was prepared by dispersing 761.9 g of KOLLICOAT™ SR-30D polymer, 11.4 g triacetin in 426.7 g of purified water and mixing for 1 hour. The coating process was performed in a VECTOR™ FLM-1 fluid bed processor by applying 1050 g of the coating solution to 600 g of Metformin Resin Complex using WURSTER process, resulting in a 35% weight gain. The coating conditions were controlled at an inlet temperature of about 68-72° C., product temperature of 28-38° C., air flow of 16-24 cfm, nozzle pressure of 2.5 kg/cm², accelerator air pressure of 1.0 kg/cm² and a spray rate of 5-7 g/min, so that a uniform coating was achieved. The Coated Metformin Resin Complex was then placed at 60° C. for 5 hours for curing.

Example 14

Preparation of Coated Ibuprofen Resin Complex

| Ingredient | Quantity |
| --- | --- |
| Ibuprofen Resin Complex | |
| Ibuprofen | 400 g |
| Purified Water | 8 L |
| PUROLITE A430MR Resin | 800 g |
| KOLLICOAT SR-30D polymer system | 250 g |
| Coated Ibuprofen Resin Complex | |
| KOLLICOAT SR-30D polymer system | 761.9 g |
| Triacetin | 11.4 g |
| Purified Water | 426.7 g |
| Ibuprofen Resin Complex | 600 g |

The Ibuprofen Resin Complex was prepared by first dissolving 400 g of Ibuprofen in 8 L of purified water (adjusted to pH >8 with 10N NaOH), and then slowly adding 800 g of PUROLITE™ A430MR resin with continuous mixing. The dispersion was mixed for 4 hours and upon completion, allowed to settle before decanting the supernatant. The slurring/decanting process was repeated twice with sufficient amounts of purified water. The wet resin complex was then dried in a VWR™ convection oven maintained at 50° C. until the moisture content was about 25%. KOLLICOAT™ SR-30D (250 g) was then slowly added to the wet resin complex in a Hobart type mixer (Kitchen Aid) to form a uniform mass. The wet mass was again dried in a 50° C. VWR™ convection oven to the moisture content of about 20%. The semi-dried granules were then milled through a 40 mesh screen using CO-MIL™ brand mill and drying was continued at 50° C. until the moisture content was between 4-6%. The dried granules were again milled through a 40 mesh screen using CO-MIL™.

The coating solution was prepared by dispersing 761.9 g of KOLLICOAT™ SR-30D polymer, 11.4 g triacetin in 426.7 g of purified water and mixing for 1 hour. The coating process was performed in a VECTOR™ FLM-1 fluid bed processor by applying 1050 g of the coating solution to 600 g of Ibuprofen Resin Complex using Wurster process, resulting in a 35% weight gain. The coating conditions were controlled at an inlet temperature of about 55-70° C., product temperature of 28-33° C., air flow of 16-21 cfm, nozzle pressure of 2.5 kg/cm², accelerator air pressure of 1.0 kg/cm² and a spray rate of 4-7 g/min, so that a uniform coating was achieved. The Coated Ibuprofen Resin Complex was then placed at 60° C. for 5 hours for curing.

Preparation of Suspension

Example 15

Preparation of Albuterol Suspension

| Ingredient | Quantity |
| --- | --- |
| Placebo Suspension Base | |
| Purified Water | 500 g |
| Citric Acid, anhydrous | 4 g |
| FD&C Yellow #6 | 0.032 g |
| FD&C Red #40 | 0.072 g |
| High Fructose Corn Syrup 42 | 600 g |
| Methylparaben | 3.6 g |
| Propylparaben | 0.4 g |
| Glycerin | 200 g |
| Sucrose | 300 g |
| Starch | 50.13 g |
| Xanthan Gum | 4.35 g |
| Strawberry/Banana flavor | 22.44 g |
| QS Purified Water | 1,742.45 g |

| Ingredient | Quantity |
|---|---|
| Albuterol ER Suspension | |
| Purified Water | 100 g |
| Polysorbate 80 | 0.55 g |
| Coated Albuterol Resin Complex (from Example 3) | 5.54 g |
| Placebo Suspension Base | 435.6 g |
| Purified Water | QS 500 mL |

Placebo Suspension Base was prepared by first dissolving 4 g of citric acid in 500 g of purified water in the main container, followed by adding 600 g of high fructose corn syrup and 300 g of sucrose to achieve complete solution. In a separate container, 0.032 g of FD&C Yellow #6 and 0.072 g of g of FD&C Red #40 were dissolved in sufficient amount of purified water and then transferred to the main container. The starch (50.13 g) was then slowly introduced to the main container under high speed/shear mixing condition to achieve uniform dispersion. In another container, 200 g of glycerin was added and heated to 45-50° C. before additions of 3.6 g of methylparaben and 0.4 g of propylparaben. After both parabens were dissolved, the solution was then cooled to room temperature and 4.35 g of xanthan gum was slowly introduced to the solution to form a uniform dispersion. The gum dispersion was then transferred to the main container under high speed/shear mixing condition to achieve uniform suspension. The 22.44 g of strawberry/banana flavor was added and the Placebo Suspension Base was achieved by adjusting to final weight of 1,742.45 g with purified water and mixed until uniform. To prepare the final suspension, 0.55 g of polysorbate 80 was dissolved in 100 g of purified water followed by addition of 435.6 g of Placebo Suspension Base. The Coated Albuterol Resin Complex prepared as described in Example 3 (5.54 g) was then slowly introduced to the above dispersion under gentle mixing condition. The final suspension was obtained by adjusting the volume to 500 mL with appropriate amount of purified water and mixed until uniform.

Example 16

Preparation Morphine Suspension

| Ingredient | Quantity |
|---|---|
| Placebo Suspension Base | |
| Tartaric Acid | 8 g |
| FD&C Red #40 | 0.144 g |
| Cherry Flavor | 2.06 g |
| High Fructose Corn Syrup 42 | 1,200 g |
| Methylparaben | 7.2 g |
| Propylparaben | 0.8 g |
| Glycerin | 400 g |
| Sucrose | 600 g |
| AVICEL RC-591 microcrystalline cellulose | 48 g |
| Xanthan Gum | 7.68 g |
| Purified Water | QS 3,484.91 g |
| Morphine ER Suspension | |
| Purified Water | 20 g |
| Sodium Metabisulfite | 0.1 g |
| Polysorbate 80 surfactant | 0.11 g |
| Coated Morphine Resin Complex (from Example 1) | 3.2 g |
| Placebo Suspension Base | 87.12 g |
| Purified Water | QS 100 mL |

Placebo Suspension Base was prepared by first dissolving 8 g of tartaric acid in appropriate amount of purified water in the main container, followed by adding 1,200 g of high fructose corn syrup and 600 g of sucrose to achieve a complete solution. In a separate container, 0.144 g of FD&C Red #40 was dissolved in a sufficient amount of purified water and then transferred to the main container. The AVICEL RC-591 microcrystalline cellulose (48 g) was then slowly introduced to the main container under high shear mixing condition to achieve uniform dispersion. In another container, 400 g of glycerin was added and heated to 45-50° C. before additions of 7.2 g of methylparaben and 0.8 g of propylparaben. After both parabens were dissolved, the solution was then cooled to room temperature and 7.68 g of xanthan gum was slowly introduced to the solution to form a uniform dispersion. The gum dispersion was then transferred to the main container under high speed/shear mixing condition to achieve uniform suspension. The 2.06 g of cherry flavor was added and the Placebo Suspension Base was achieved by adjusting to final weight of 3,484.91 g with purified water and mixed until uniform. To prepare the final suspension, 0.1 g of sodium metabisulfite and 0.11 g of Polysorbate 80 surfactant were dissolved in 20 g of purified water followed by addition of 87.12 g of Placebo Suspension base. The Coated Morphine Resin Complex prepared according to Example 1 of 3.2 g was then slowly introduced to the above dispersion under gentle mixing condition. The final suspension was obtained by adjusting the volume to 100 mL with appropriate amount of purified water and mixed until uniform.

Example 17

Preparation Oxycodone Suspension

| Ingredient | Quantity |
|---|---|
| Placebo Suspension Base | |
| Tartaric Acid | 8 g |
| FD&C Red #40 | 0.144 g |
| Strawberry Flavor | 2.06 g |
| High Fructose Corn Syrup 42 | 1,200 g |
| Methylparaben | 7.2 g |
| Propylparaben | 0.8 g |
| Glycerin | 400 g |
| Sucrose | 600 g |
| Avicel RC-591 microcrystalline cellulose | 48 g |
| Xanthan Gum | 7.68 g |
| Purified Water | QS 3,484.91 g |
| Oxycodone ER Suspension | |
| Purified Water | 100 g |
| Sodium Metabisulfite | 0.5 g |
| Polysorbate 80 surfactant | 0.55 g |
| Coated Oxycodone Resin Complex (from Example 2) | 5.66 g |
| Placebo Suspension Base | 435.6 g |
| Purified Water | QS 500 mL |

Placebo Suspension Base was prepared by first dissolving 8 g of tartaric acid in appropriate amount of purified water in the main container, followed by adding 1,200 g of high fructose corn syrup and 600 g of sucrose to achieve complete solution. In a separate container, 0.144 g of FD&C Red #40 was dissolved in sufficient amount of purified water and then transferred to the main container. The AVICEL RC-591 microcrystalline cellulose (48 g) was then slowly introduced to the main container under high shear mixing condition to achieve uniform dispersion. In another container, 400 g of glycerin was added and heated to 45-50° C. before additions of 7.2 g of methylparaben and 0.8 g of propylparaben. After both parabens were dissolved, the solution was then cooled to room temperature and 7.68 g of xanthan gum was slowly introduced to the solution to form a uniform dispersion. The gum dispersion was then transferred to the main container under high speed/shear mixing condition to achieve uniform suspension. The 2.06 g of strawberry flavor was added and the Placebo Suspension Base was achieved by adjusting to final weight of 3484.91 g with purified water and mixed until uniform. To prepare the final suspension, 0.5 g of sodium metabisulfite and 0.55 g of polysorbate 80 surfactant were dissolved in 100 g of purified water followed by addition of 435.6 g of Placebo Suspension Base. The Coated Oxycodone Resin Complex prepared according to Example 2 (5.66 g) was then slowly introduced to the above dispersion under gentle mixing condition. The final suspension was obtained by adjusting the volume to 500 mL with appropriate amount of purified water and mixed until uniform.

Example 18

Orally Disintegrating Tablet Formulation

Preparation of Coated Dextromethorphan Resin Complex

| Ingredient | Quantity |
| --- | --- |
| Dextromethorphan Resin Complex | |
| Dextromethorphan HBr USP | 954 g |
| Purified Water | 8 L |
| AMBERLITE IRP-69 resin (anhydrous) | 1,758 g |
| KOLLIDON K-30 brand PVP | 116 g |
| Purified Water | 1,151 g |
| Coated Dextromethorphan Resin Complex | |
| KOLLICOAT SR-30D polymer system | 635 g |
| Triacetin | 9.5 g |
| Purified Water | 356 g |
| Dextromethorphan Resin Complex | 600 g |

The Dextromethorphan Resin Complex was prepared by first dissolving 954 g of dextromethorphan HBr in 8 L of purified water heated to 75-80° C., followed by the addition of 1,758 g of AMBERLITE™ IRP-69 resin under gentle mixing for 4 hours. At the completion, the suspension was allowed to settle, decanted and rinsed with purified water twice and dried in an oven maintained at 50° C. until moisture was around 5%. The PVP solution was prepared by dissolving 116 g of KOLLIDON K-30 brand PVP in 1,151 g of purified water and the solution was slowly added to the Dextromethorphan Resin Complex in a Hobart type mixer (Kitchen Aid) to form a uniform mass and dried at 50° C. until moisture is between 3-7%. The dried granules were then milled through a 40 mesh screen using Co-Mil™ brand mill.

The coating solution was prepared by first gently mixing 635 g of KOLLICOAT™ SR-30D polymer system, 9.5 g of triacetin and 356 g of purified water for 1 hour. The coating process was performed in VECTOR™ FLM-1 fluid bed processor by applying 900 g of the coating solution to 600 g of Dextromethorphan Resin Complex using Wurster process that resulted in 30% weight gain. The coating conditions were controlled at an inlet temperature of 62-76° C., product temperature of 28-35° C., air flow of 16-20 cfm, nozzle pressure of 2.5 kg/cm$^2$, accelerator air pressure of 1.0 kg/cm$^2$ and spray rate of 4-6 g/min so that uniform coating was achieved. The Coated Dextromethorphan Resin Complex was then placed at 60° C. for 5 hours for curing.

Preparation of Uncoated Dextromethorphan Resin Complex

An Uncoated Dextromethorphan Resin Complex was prepared as follows.

| Ingredient | Quantity |
| --- | --- |
| Uncoated Dextromethorphan Resin Complex | |
| Dextromethorphan HBr USP | 119.28 g |
| Purified Water | 1 L |
| AMBERLITE IRP-69 RESIN (anhydrous) | 223.01 g |

Uncoated Dextromethorphan Resin Complex was prepared by first dissolving 119.28 g of dextromethorphan HBr in 1 L of purified water heated to 75-80° C., followed by the addition of 223.01 g AMBERLITE IRP-69 resin under gentle mixing for 4 hours. At the completion, the suspension was allowed to settle, and was then decanted and rinsed with purified water twice and dried in an oven maintained at 50° C. until the moisture content is around 5%. The dried resin complex was hand sieved through 40 mesh screen.

Tablet Preparation

The Coated Dextromethorphan Resin and Uncoated Dextromethorphan Resin of this example were utilized in tablet preparation as follows.

| Ingredient | Quantity per tablet | Quantity |
| --- | --- | --- |
| Uncoated Dextromethorphan Resin | 23.78 mg | 4.76 g |
| Coated Dextromethorphan Resin | 72.70 mg | 14.54 g |
| Calcium Silicate | 49 mg | 9.8 g |
| Zeopharm | 3.5 mg | 0.7 g |
| Silicon Dioxide | 5.0 mg | 1.0 g |
| Microcrystalline Cellulose | 24 mg | 4.8 g |
| Acesulfame K sugar substitute | 2 mg | 0.4 g |
| Aspartame | 5 mg | 1.0 g |
| Peppermint | 2.5 mg | 0.5 g |
| Crospovidone | 15 mg | 3.0 g |
| Mannitol | 124 mg | 24.8 g |
| Mg Stearate | 5 mg | 1.0 g |
| Total | 331.48 mg | 66.30 g |

A small batch of tablets were prepared by first adding quantities of the Uncoated and Coated Dextromethorphan Resin, calcium silicate, zeopharm, silicon dioxide, microcrystalline cellulose, crospovidone, Acesulfame-K sugar substitute, Aspartame and mannitol in the amounts as specified in the above formulation to a blender and mixing for 10 minutes. Magnesium stearate (1.0 g) was added to the powder blend and mixed for an additional 3 minutes. The final blend was discharged into a RIMEK™ tablet press equipped with ⅜" standard concave tooling and tablets of moderate hardness (3-6 Kp tested by VANDERKAMP™ tablet hardness tester) were compressed.

Dissolution release rate of the oral disintegrating dextromethorphan extended release tablets of the invention was conducted in 900 mL 0.4M KH$_2$PO$_4$ at paddle, 50 rpm and the results of the tablets showed comparable results to the ER suspension.

Example 19

Color Migration of Water Soluble Dyes in Finished Formulations Having Drug-Ion Exchange Resin Complexes Coated with EUDRAGIT Brand Polymer Coating—Comparative Example Dextromethorphan suspension prepared with uncoated and EUDRAGIT coated Dextromethorphan Resin Complex was observed to have color migration; this color migration was more pronounced at 40° C./75% RH as compared to 25° C./60% RH.

Preparation of Uncoated and Coated Dextromethorphan Resin Complex

| Ingredient | Quantity |
|---|---|
| Uncoated Dextromethorphan Resin Complex | |
| Dextromethorphan HBr USP | 119.28 g |
| Purified Water | 1 L |
| AMBERLITE IRP-69 RESIN (anhydrous) | 223.01 g |

Uncoated Dextromethorphan Resin Complex was prepared by first dissolving 119.28 g of dextromethorphan HBr in 1 L of purified water heated to 75-80° C., followed by the addition of 223.01 g AMBERLITE IRP-69 resin under gentle mixing for 4 hours. At the completion, the suspension was allowed to settle, and was then decanted and rinsed with purified water twice and dried in an oven maintained at 50° C. until the moisture content was around 5%. The dried resin complex was hand sieved through a 40 mesh screen.

| Ingredient | Quantity |
|---|---|
| Dextromethorphan Resin Complex | |
| Dextromethorphan HBr USP | 954.2 g |
| Purified Water | 8 L |
| AMBERLITE IRP-69 RESIN (anhydrous) | 1784.0 g |
| KOLLIDON K-30 polyvinyl pyrrolidone | 116 g |
| Purified Water | 528.4 g |
| Coated Dextromethorphan Resin Complex | |
| Eudragit RS-30D polymer system | 334.89 g |
| Triethyl Citrate | 20.25 g |
| Talc | 50.19 g |
| Polysorbate 80 surfactant | 0.29 g |
| Purified Water | 292.2 g |
| Dextromethorphan Resin Complex | 600 g |

The Dextromethorphan Resin Complex was prepared by first dissolving 954.2 g of dextromethorphan HBr in 8 L of purified water heated to 75-80° C., followed by the addition of 1784 g of AMBERLITE IRP-69 resin under gentle mixing for 4 hours. At the completion, the suspension was allowed to settle, decanted and rinsed with purified water twice and dried in an oven maintained at 50° C. until moisture was around 5%. The PVP solution prepared by dissolving 116 g of KOLLIDON K-30 in 528.4 g of purified water was slowly added to the Dextromethorphan Resin Complex in a Hobart type mixer (Kitchen Aid) to form a uniform mass and dried at 50° C. until moisture was between 3-7%. The dried granules were then milled through a 40 mesh screen using Co-Mil.

Coating solution was prepared by gently mixing 334.89 g of Eudragit RS-30D polymer system, 0.29 g of polysorbate 80 surfactant, 20.25 g of triethyl citrate and 292.2 g of purified water for 45 minutes, followed by addition of 50.19 g of talc and continued mixing for 1 hour. The coating process was performed in Glatt GPCG-1 fluid bed processor by applying 698 g of the coating solution to 600 g of Dextromethorphan Resin Complex using WURSTER Process that resulted in 28.5% weight gain. The coated Dextromethorphan Resin Complex was placed at 60° C. for 5-hour curing.

Preparation Dextromethorphan Suspension

| Ingredient | Quantity |
|---|---|
| Placebo Suspension Base | |
| Citric Acid | 6 g |
| FD&C Yellow #6 | 0.03278 g |
| Orange Flavor | 2.01 g |
| High Fructose Corn Syrup 42 | 600 g |
| Methylparaben | 3.6 g |
| Propylparaben | 0.6 g |
| Propylene Glycol | 100 g |
| Sucrose | 300 g |
| Tragacanth Gum | 10.51 g |
| Xanthan Gum | 3.59 g |
| Purified Water | 1,015 g |
| Dextromethorphan Suspension | |
| Purified Water | 10 g |
| Polysorbate 80 surfactant | 0.22 g |
| Uncoated Dextromethorphan Resin Complex | 2.68 g |
| Coated Dextromethorphan Resin Complex | 1.00 g |
| Placebo Suspension Base | 203.15 g |
| Purified Water | QS 200 mL |

Placebo Suspension Base was prepared by first dissolving 6 g of citric acid in an appropriate amount of purified water from the total 1,015 g in the main container, followed by adding 300 g of sucrose and 600 g of high fructose corn syrup to achieve complete solution. In a separate container, 0.03278 g of FD&C Yellow #6 was dissolved in sufficient amount of purified water and then transferred to the main container. In another container, 100 g of propylene glycol was added and heated to 45-50° C. before additions of 3.6 g of methylparaben and 0.6 g of propylparaben. After both parabens were dissolved, the solution was then cooled to room temperature and 10.51 g of tragacanth gum and 3.59 g of xanthan gum were slowly introduced to the solution to form a uniform dispersion. The gum dispersion was then transferred to the main container under high speed/shear mixing condition to achieve uniform suspension. The 2.01 g of orange flavor was added and the Placebo Suspension Base was achieved by addition of the remaining purified water and mixed until uniform. To prepare the final suspension, 0.22 g of Polysorbate 80 surfactant were dissolved in 10 g of purified water followed by addition of 203.15 g of Placebo Suspension Base. The Uncoated Dextromethorphan Resin complex of 2.68 g and Coated Dextromethorphan Resin Complex of 1 g were then slowly introduced to the above dispersion under gentle mixing condition. The final suspension was obtained by adjusting the volume to 200 mL with appropriate amount of purified water and mixed until uniform.

When a drug-ion-exchange resin complexes prepared according to the invention and coated methacrylic acid copolymers such as a EUDRAGIT brand polymer coat, was mixed with a dye in the liquid suspension, the dye tended to migrate onto the surface of the polymer and resulted in non-uniform color distribution in the liquid. The use of a EUDRAGIT brand polymer in the finished liquid suspension containing water soluble dyes creates issued of non-uniform color distribution due to the color migration. Furthermore, the nature of the EUDRAGIT brand polymer, the polymer also caused flocculation of the resin resulting in flaky agglomerates in the liquid suspension.

Example 20

Ethylcellulose-Coated Drug—Ion Exchange Resin in a Liquid Suspension Formulation—Comparative Example

Dextromethorphan suspension prepared with uncoated and AQUACOAT™ coated dextromethorphan resin complex was observed to have loose and chunky flakes in the suspension. This was more pronounced at 40° C./75% RH than at 25° C./60% RH.

Preparation of Coated Dextromethorphan Resin Complex

| Ingredient | Quantity |
|---|---|
| Coated Dextromethorphan Resin Complex | |
| AQUACOAT ECD-30 polymer system | 460.08 g |
| Dibutyl Sebacate | 33.56 g |
| Purified Water | 115.97 g |
| Dextromethorphan Resin Complex (from Example 18) | 600 g |

Coating solution was prepared by first gently mixing 460.08 g of AQUACOAT ECD-30 and 33.56 g of dibutyl sebacate for 45 minutes, followed by addition of 115.97 g of purified water and continued mixing for 30 minutes. The coating process was performed in Glatt GPCG-1 fluid bed processor by applying 615 g of the coating solution to 600 g of Dextromethorphan Resin Complex using WURSTER process that resulted in 28.9% weight gain. The coated Dextromethophan Resin Complex was placed at 60° C. for 5-hour curing.

Preparation of Dextromethorphan Suspension

| Ingredient | Quantity |
|---|---|
| Dextromethorphan ER Suspension | |
| Purified Water | 10 g |
| Polysorbate 80 surfactant | 0.22 g |
| Uncoated Dextromethorphan Resin Complex (from Example 18) | 1.50 g |
| Coated Dextromethorphan Resin Complex | 2.68 g |
| Placebo Suspension Base (from Example 18) | 203.14 g |
| Purified Water | QS 200 mL |

To prepare the final suspension, 0.22 g of Polysorbate 80 were dissolved in 10 g of purified water followed by addition of 203.14 g of Placebo Suspension Base. The Uncoated Dextromethorphan Resin complex of 1.50 g and Coated Dextromethorphan Resin Complex of 2.68 g were then slowly introduced to the above dispersion under gentle mixing condition. The final suspension was obtained by adjusting the volume to 200 mL with appropriate amount of purified water and mixed until uniform.

When the ethylcellulose-coated particles were made into a liquid suspension, the coated particles showed as flaky, swollen and chunky, an indication of loose adhesion of the ethylcellulose coating to the particle surface. These ethylcellulose-coated particles exhibited in little or no significant reductions in the release rate of the drug.

Abuse Resistant Characteristics of Products of Invention

Example 21

Preparation of Uncoated and Coated Dextromethorphan Resin Complex

| Ingredient | Quantity |
|---|---|
| Uncoated Dextromethorphan Resin Complex | |
| Dextromethorphan HBr USP | 95.42 g |
| Purified Water | 0.8 L |
| AMBERLITE IRP-69 resin (anhydrous) | 175.82 g |

The Uncoated Dextromethorphan Resin Complex was prepared by first dissolving 95.42 g of dextromethorphan HBr in 0.8 L of purified water heated to 75-80° C., followed by the addition of 175.82 g AMBERLITE IRP-69 resin (anhydrous) under gentle mixing for 4 hours. At the completion, the suspension was allowed to settle, decanted and rinsed with purified water twice and dried in an oven maintained at 50° C. until moisture is around 5%. The dried resin complex was hand sieved through a 40 mesh screen.

| Ingredient | Quantity |
|---|---|
| Dextromethorphan Resin Complex | |
| Dextromethorphan HBr USP | 954 g |
| Purified Water | 8 L |
| AMBERLITE IRP-69 resin (anhydrous) | 1,758 g |
| KOLLIDON K-30 polyvinylpyrrolidone | 116 g |
| Purified Water | 1,151 g |
| Coated Dextromethorphan Resin Complex | |
| KOLLICOAT SR-30D polymer system | 761 g |
| Triacetin | 11.4 g |
| Purified Water | 427 g |
| Dextromethophan Resin Complex | 1,200 g |

The Dextromethorphan Resin Complex was prepared by first dissolving 954 g of dextromethorphan HBr in 8 L of purified water heated to 75-80° C., followed by the addition of 1,758 g of AMBERLITE IRP-69 resin under gentle mixing for 4 hours. At the completion, the suspension was allowed to settle, decanted and rinsed with purified water twice and dried in an oven maintained at 50° C. until moisture is around 5%. The polyvinyl pyrrolidone (PVP) solution was prepared by dissolving 116 g of KOLLIDON K-30 PVP in 1,151 g of purified water and the solution was slowly added to the Dextromethorphan Resin Complex in a Hobart type mixer (KitchenAid) to form a uniform mass and dried at 50° C. until moisture is between 3-7%. The dried granules were then milled through a 40 mesh screen using CO-MIL brand mill.

Coating solution was prepared by first gently mixing 761 g of KOLLICOAT SR-30D polymer system, 11.4 g of triacetin and 427 g of purified water for 1 hour. The coating process was performed in VECTOR™ FLM-1 fluid bed processor by applying 1050 g of the coating solution to 600 g of Dextromethorphan Resin Complex using Wurster process that resulted in 35% weight gain. The coating conditions were controlled at am inlet temperature of 59-75° C., product temperature of 27-35° C., air flow of 15-20 cfm, nozzle pressure of 2.5 kg/cm$^2$, accelerator air pressure of 1.0 kg/cm$^2$ and spray rate of 4-6 g/min so that uniform coating was achieved. The Coated Dextromethorphan Resin Complex was then placed at 60° C. for 5 hours for curing.

Preparation Dextromethorphan ER Suspension

| Ingredient | Quantity |
|---|---|
| Dextromethorphan ER Suspension | |
| Purified Water | 20 g |
| Polysorbate 80 | 0.11 g |
| Uncoated Dextromethorphan Resin Complex | 0.476 g |
| Coated Dextromethorphan Resin Complex | 1.596 g |
| Sodium Metabisulfite | 0.1 g |
| Placebo Suspension Base (from Example 18) | 87.12 g |
| Purified Water | QS 100 mL |

To prepare the Dextromethorphan ER Suspension, the resin blend was prepared by mixing 0.476 g of uncoated dextromethorphan resin and 1.596 g of coated dextromethorphan resin. The blend was subsequently passed through CO-MIL™ brand mill equipped with 40 mesh screen. Dextromethorphan Suspension was prepared by dissolving 0.11 g of Polysorbate 80 surfactant and 0.1 g of sodium metabisulfite in 20 g of purified water followed by addition of 87.12 g of placebo suspension base. The resin blend of uncoated and coated Dextromethorphan Resin Complex was then slowly introduced to the above dispersion under gentle mixing condition. The final suspension was obtained by adjusting the volume to 100 mL with appropriate amount of purified water and mixed until uniform.

Another suspension was prepared with the same ingredients and procedures with the exception that the resin blend was not milled through CO-MIL™ brand mill.

Dissolution of both suspensions in 500 mL 0.1N HCl for 1 hour followed by 900 mL of pH 6.8 buffer until 24 hours under paddle, 50 rpm were compared and results indicated no statistically significant differences. The strong external milling forces applied to the uncoated and coated resin complex did not change the dissolution behavior of its suspension when compared to the suspension prepared with un-milled resin blend, indicating that the flexible film is not disrupted.

The drug resin complex coated with polymer film showed enhanced resistance to abuse potential. The coated particles subjected to grinding mechanical forces as described above did not change its dissolution behaviors indicating that the combined complexation and highly flexible film make it extremely difficult to remove the drug from the coated particles with ordinary mechanical means.

Example 22

Preparation of Pseudoephedrine Suspension

| Ingredient | Quantity |
|---|---|
| Placebo Suspension Base | |
| Citric Acid | 8 g |
| FD&C Yellow #6 | 0.064 g |
| FD&C Red #40 | 0.144 g |
| Strawberry/Banana Flavor | 44.88 g |
| High Fructose Corn Syrup 42 | 1,200 g |
| Methylparaben | 7.2 g |
| Propylparaben | 0.8 g |
| Glycerin | 400 g |
| Sucrose | 600 g |
| Starch | 100.26 g |
| Xanthan Gum | 8.7 g |
| Purified Water | QS 3484.91 g |
| Pseudoephedrine ER Suspension | |
| Purified Water | 20 g |
| Polysorbate 80 surfactant | 0.11 g |
| Coated Pseudoephedrine Resin Complex (from Example 8) | 3.11 g |
| Placebo Suspension Base | 87.12 g |
| Purified Water | QS 100 mL |

Placebo Suspension Base was prepared by first dissolving 8 g of citric acid in an appropriate amount of purified water, followed by adding 600 g of sucrose and 1200 g of high fructose corn syrup to achieve complete solution. In a separate container, 0.064 g of FD&C Yellow #6 and 0.144 g of FD&C Red #40 were dissolved in a sufficient amount of purified water and then transferred to the main container. The starch (100.26 g) was then slowly introduced to the main container under high shear mixing condition to achieve uniform dispersion. In another container, 400 g of glycerin was added and heated to 45-50° C. before additions of 7.2 g of methylparaben and 0.8 g of propylparaben. After both parabens were dissolved, the solution was then cooled to room temperature and 8.7 g of xanthan gum were slowly introduced to the solution to form a uniform dispersion. The gum dispersion was then transferred to the main container under high speed/shear mixing condition to achieve uniform suspension. The 44.88 g of strawberry/banana flavor was added and the Placebo Suspension Base was achieved by addition of the remaining purified water and mixed until uniform.

To prepare the Pseudoephedrine ER Suspension, the Coated Pseudoephedrine Resin Complex of 3.11 g was passed through CO-MIL™ equipped with a 40 mesh screen. Pseudoephedrine Suspension was prepared by dissolving 0.11 g of Polysorbate 80 surfactant in 20 g of purified water followed by addition of 87.12 g of Placebo Suspension base. The Coated Pseudoephedrine Resin Complex was then slowly introduced to the above dispersion under gentle mixing condition. The final suspension was obtained by adjusting the volume to 100 mL with appropriate amount of purified water and mixed until uniform.

Another suspension was prepared with the same ingredients and procedures with the exception that the Coated Pseudoephedrine Resin Complex was not milled through CO-MIL™.

Dissolution of both suspensions in 500 mL 0.1N HCl for 1 hour followed by 900 mL of pH 6.8 buffer until 24 hours under paddle, 50 rpm were compared and results indicated no significant differences. The strong external milling forces applied to the milled coated resin complex did not change the dissolution behavior of its suspension when compared to the suspension prepared with un-milled coated resin.

All patents, patent publications, and other publications listed in this specification, as well as priority documents U.S. patent application Ser. No. 15/200,786, filed Oct. 27, 2016, U.S. patent application Ser. No. 15/047,388, filed Feb. 18, 2016, which is a continuation of U.S. patent application Ser. No. 14/508,613, filed Oct. 7, 2014, which is a continuation of U.S. patent application Ser. No. 14/155,410, filed Jan. 15, 2014, now U.S. Pat. No. 8,883,217; U.S. patent application Ser. No. 14/065,842, filed Oct. 29, 2013, now U.S. Pat. No. 8,747,902, issued Jun. 10, 2014; U.S. patent application Ser. No. 14/044,105, filed Oct. 2, 2013, now U.S. Pat. No.

8,790,700, issued Jul. 29, 2014; U.S. patent application Ser. No. 13/746,654, filed Jan. 22, 2013, now U.S. Pat. No. 8,597,684, issued Dec. 3, 2013; U.S. patent application Ser. No. 13/666,424, filed Nov. 1, 2012, now U.S. Pat. No. 8,491,935, issued Jul. 23, 2013; U.S. patent application Ser. No. 12/722,857, filed Mar. 12, 2010, now U.S. Pat. No. 8,337,890, issued Dec. 25, 2012; U.S. patent application Ser. No. 11/724,966, filed Mar. 15, 2007, now U.S. Pat. No. 8,062,667, issued Nov. 22, 2011; and U.S. Provisional Patent Application No. 60/783,181, filed Mar. 16, 2006, now expired, are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. An orally ingestible aqueous liquid suspension comprising:
 (A) modified release, barrier coated particulates which do not need an enteric coating to provide prolonged release which comprise:
  (i) a particulate drug-cation exchange resin complex comprising at least one drug bound to a pharmaceutically acceptable water insoluble cation exchange resin, wherein said particulate drug-cation exchange resin complex is of a size capable of passing through a number 40 mesh screen and wherein said at least one drug is amphetamine or dextro-amphetamine and
  (ii) about 20% w/w to about 50% w/w of a water permeable, water insoluble, non-ionic, modified release diffusion barrier coating based on the weight of the barrier coated particulates, said barrier coating having an elongation factor of about 125% to about 400% and which provides a modified release profile to the drug in said drug-cation exchange resin complex and which comprises: (a) a water-insoluble polymer, and (b) about 2.5% w/w to about 20% w/w of a plasticizer based on the weight of the barrier coating;
 (B) at least one of (iiia) and/or (iiib):
  (iiia) an uncoated particulate dextro-amphetamine-cation exchange resin complex of a size capable of passing through a number 40 mesh screen, wherein said uncoated dextro-amphetamine-cation exchange resin complex comprises dextro-amphetamine bound to a pharmaceutically acceptable water insoluble cation exchange resin,
  (iiib) an uncoated particulate amphetamine-cation exchange resin complex of a size capable of passing through a number 40 mesh screen, wherein said uncoated amphetamine-cation exchange resin complex comprises amphetamine bound to a pharmaceutically acceptable water insoluble cation exchange resin,
 and optionally at least one of (iiic) and/or (iiid):
  (iiic) amphetamine or a pharmaceutically acceptable salt thereof which is not complexed with an ion exchange resin, or
  (iiid) dextroamphetamine or a pharmaceutically acceptable salt thereof which is not complexed with an ion exchange resin; and/or
 (C) a pharmaceutically acceptable aqueous suspension base, wherein said barrier coated drug-cation exchange resin complex as defined in (A) and said at least one additional component as defined in (B) are suspended in said base,
 wherein the water insoluble polymer in said diffusion barrier coating comprises polyvinyl acetate.

2. The orally ingestible aqueous liquid suspension according to claim 1, wherein said diffusion barrier coating is cured.

3. The orally ingestible aqueous liquid suspension according to claim 1, wherein the plasticizer is selected from dibutyl sebacate, propylene glycol, polyethylene glycol, polyvinyl alcohol, triethyl citrate, acetyl triethyl citrate, acetyl tributyl citrate, tributyl citrate, or triacetin, or mixtures thereof.

4. The orally ingestible aqueous liquid suspension according to claim 1, wherein said diffusion barrier coating further comprises a stabilizer.

5. The orally ingestible aqueous liquid suspension according to claim 1, wherein the modified release, barrier coated particulates as defined in (A) comprise about 30% w/w to about 50% w/w of said diffusion barrier coating.

6. The orally ingestible aqueous liquid suspension according to claim 1, wherein the modified release, barrier coated particulates as defined in (A) comprise about 30% w/w to about 45% w/w by weight of said diffusion barrier coating.

7. The orally ingestible aqueous liquid suspension according to claim 1 which comprises said uncoated particulate dextro-amphetamine—cation exchange resin as defined in (B)(iiia).

8. The orally ingestible aqueous liquid suspension according to claim 1 which comprises said uncoated particulate amphetamine—cation exchange resin as defined in (B)(iiib).

9. The orally ingestible aqueous liquid suspension according to claim 1 which comprises at least one of said amphetamine or pharmaceutically acceptable salt as defined in (B)(iiic) and/or said dextro-amphetamine as defined in (B)(iiid).

10. The orally ingestible aqueous liquid suspension according to claim 1, wherein said cation exchange resin used to form the complex as defined in (A), (B)(iiia), and/or (B)(iiib) is a sulfonated copolymer comprising styrene and a divinylbenzene.

11. The orally ingestible aqueous liquid suspension according to claim 1, wherein the plasticizer is present in an amount of about 5% to about 10% by weight of the coating layer.

12. An orally ingestible aqueous liquid suspension comprising:
 (A) modified release, barrier coated particulates which do not need an enteric coating to provide prolonged release which comprise:
  (i) a particulate drug-cation exchange resin complex comprising at least one drug bound to a pharmaceutically acceptable water insoluble cation exchange resin, wherein said particulate drug-cation exchange resin complex is of a size capable of passing through a number 40 mesh screen and wherein said at least one drug is amphetamine or dextro-amphetamine and
  (ii) about 20% w/w to about 50% w/w of a water permeable, water insoluble, non-ionic, modified release diffusion barrier coating based on the weight of the barrier coated particulates, said barrier coating having an elongation factor of about 125% to about 400% and which provides a modified release profile to the drug in said drug-cation exchange resin complex and which comprises: (a) a water-insoluble polymer, and (b) about 2.5% w/w to about 20% w/w of a plasticizer based on the weight of the barrier coating;

(B) at least one of (iiia) and/or (iiib):
- (iiia) an uncoated particulate dextro-amphetamine-cation exchange resin complex of a size capable of passing through a number 40 mesh screen, wherein said uncoated dextro-amphetamine-cation exchange resin complex comprises dextro-amphetamine bound to a pharmaceutically acceptable water insoluble cation exchange resin,
- (iiib) an uncoated particulate amphetamine-cation exchange resin complex of a size capable of passing through a number 40 mesh screen, wherein said uncoated amphetamine-cation exchange resin complex comprises amphetamine bound to a pharmaceutically acceptable water insoluble cation exchange resin, and optionally at least one of (iiic) and/or (iiid):
- (iiic) amphetamine or a pharmaceutically acceptable salt thereof which is not complexed with an ion exchange resin, or
- (iiid) dextroamphetamine or a pharmaceutically acceptable salt thereof which is not complexed with an ion exchange resin; and/or (C) a pharmaceutically acceptable aqueous suspension base, wherein said barrier coated drug-cation exchange resin complex as defined in (A) and said at least one additional component as defined in (B) are suspended in said base,
wherein the drug ion exchange resin as defined in (A) further comprises a water insoluble polymer or copolymer, or hydrophilic polymer which forms a matrix with the drug—cation exchange resin complex which particulate drug-cation exchange resin complex-(water insoluble polymer or copolymer or a hydrophilic polymer) matrix is capable of passing through a number 40 mesh screen.

13. The orally ingestible aqueous liquid suspension according to claim 12, wherein the hydrophilic polymer as defined in (A) is present to form the drug—cation exchange resin complex—matrix and comprises a polyvinylpyrrolidone.

14. The orally ingestible aqueous liquid suspension according to claim 12, wherein the modified release, barrier coated particulates as defined in (A) comprise about 30% w/w to about 50% w/w of said diffusion barrier coating.

15. The orally ingestible aqueous liquid suspension according to claim 12, wherein the modified release, barrier coated particulates as defined in (A) comprise about 30% w/w to about 45% w/w by weight of said diffusion barrier coating.

16. The orally ingestible aqueous liquid suspension according to claim 12 which comprises said uncoated particulate dextro-amphetamine—cation exchange resin as defined in (B)(iiia).

17. The orally ingestible aqueous liquid suspension according to claim 12 which comprises said uncoated particulate amphetamine—cation exchange resin as defined in (B)(iiib).

18. The orally ingestible aqueous liquid suspension according to claim 12 which comprises at least one of said amphetamine or pharmaceutically acceptable salt as defined in (B)(iiic) and/or said dextro-amphetamine as defined in (B)(iiid).

19. The orally ingestible aqueous liquid suspension according to claim 12, wherein said cation exchange resin used to form the complex as defined in (A), (B)(iiia), and/or (B)(iiib) is a sulfonated copolymer comprising styrene and a divinylbenzene.

20. The orally ingestible aqueous liquid suspension according to claim 12, wherein the plasticizer is selected from dibutyl sebacate, propylene glycol, polyethylene glycol, polyvinyl alcohol, triethyl citrate, acetyl triethyl citrate, acetyl tributyl citrate, tributyl citrate, or triacetin, or mixtures thereof.

21. The orally ingestible aqueous liquid suspension according to claim 12, wherein the water insoluble polymer in said diffusion barrier coating comprises polyvinyl acetate.

22. The orally ingestible aqueous liquid suspension according to claim 21, wherein said diffusion barrier coating is cured.

* * * * *